(12) United States Patent
Campbell et al.

(10) Patent No.: US 11,613,590 B2
(45) Date of Patent: *Mar. 28, 2023

(54) BINDING PROTEINS 1

(71) Applicants: Nucleus Therapeutics Pty. Ltd., South Melbourne (AU); Yale University, New Haven, CT (US)

(72) Inventors: James Campbell, Melbourne (AU); Valentina Dubljevic, Melbourne (AU); James Hansen, Guilford, CT (US); Zahra Rattray, New Haven, CT (US); Jiangbing Zhou, Cheshire, CT (US)

(73) Assignees: Nucleus Therapeutics Pty. Ltd, South Melbourne (AU); Yale University, New Haven, CT (US)

( * ) Notice: Subject to any disclaimer, the term of this patent is extended or adjusted under 35 U.S.C. 154(b) by 421 days.

This patent is subject to a terminal disclaimer.

(21) Appl. No.: 16/631,418

(22) PCT Filed: Jul. 17, 2018

(86) PCT No.: PCT/US2018/042532
§ 371 (c)(1),
(2) Date: Jan. 15, 2020

(87) PCT Pub. No.: WO2019/018426
PCT Pub. Date: Jan. 24, 2019

(65) Prior Publication Data
US 2020/0216567 A1    Jul. 9, 2020

Related U.S. Application Data

(60) Provisional application No. 62/596,694, filed on Dec. 8, 2017, provisional application No. 62/533,546, filed on Jul. 17, 2017.

(51) Int. Cl.
C07K 16/00    (2006.01)
A61K 39/395   (2006.01)
C07K 16/44    (2006.01)
A61P 35/00    (2006.01)
A61K 39/00    (2006.01)
A61K 31/502   (2006.01)

(52) U.S. Cl.
CPC .............. *C07K 16/44* (2013.01); *A61P 35/00* (2018.01); *A61K 31/502* (2013.01); *A61K 2039/505* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/626* (2013.01); *C07K 2317/77* (2013.01); *C07K 2317/82* (2013.01)

(58) Field of Classification Search
CPC ................ A61P 35/00; C07K 2317/56; C07K 2317/565

See application file for complete search history.

(56) References Cited

U.S. PATENT DOCUMENTS

| | | |
|---|---|---|
| 2008/0085241 A1 | 4/2008 | Stassar et al. |
| 2013/0266570 A1 | 10/2013 | Weisbart et al. |
| 2015/0064181 A1 | 3/2015 | Armstrong |
| 2016/0235859 A1 | 8/2016 | Weisbart et al. |
| 2017/0073429 A1 | 3/2017 | Hansen et al. |
| 2017/0130216 A1 | 5/2017 | Armstrong |

FOREIGN PATENT DOCUMENTS

| | | |
|---|---|---|
| WO | WO 2016033321 | 3/2016 |
| WO | WO 2016033324 | 3/2016 |

OTHER PUBLICATIONS

U.S. Appl. No. 16/631,421, filed Jan. 15, 2020, Campbell et al.

*Primary Examiner* — Mark Halvorson
(74) *Attorney, Agent, or Firm* — Bozicevic, Field & Francis LLP; Shweta Chandra

(57) ABSTRACT

The present disclosure relates to cell penetrating anti-DNA binding proteins. Compositions comprising these binding proteins may be may be useful for delivering agents to cells and treating diseases such as cancer.

20 Claims, 18 Drawing Sheets

Figure 3:
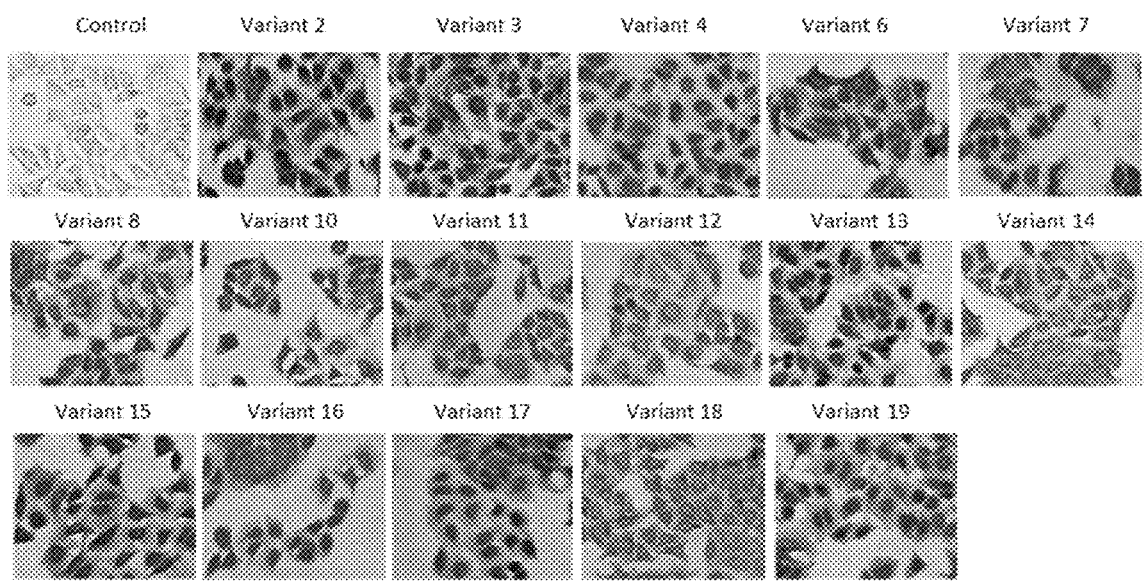

Specification includes a Sequence Listing.

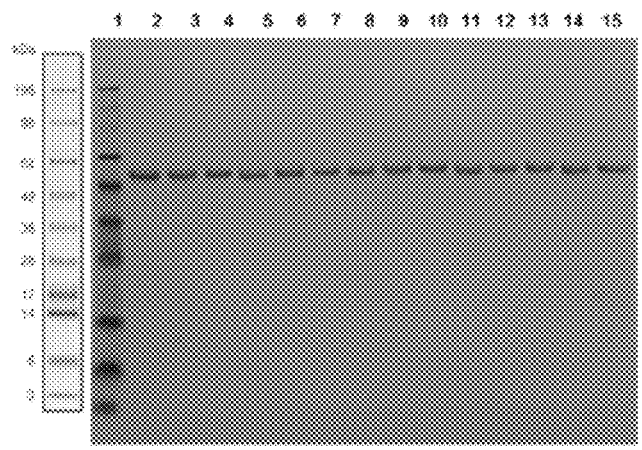
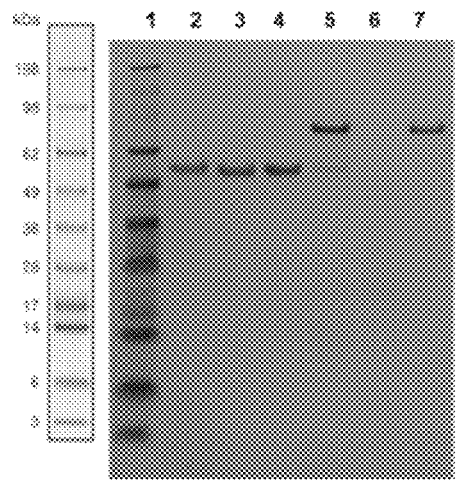
FIGURE 1

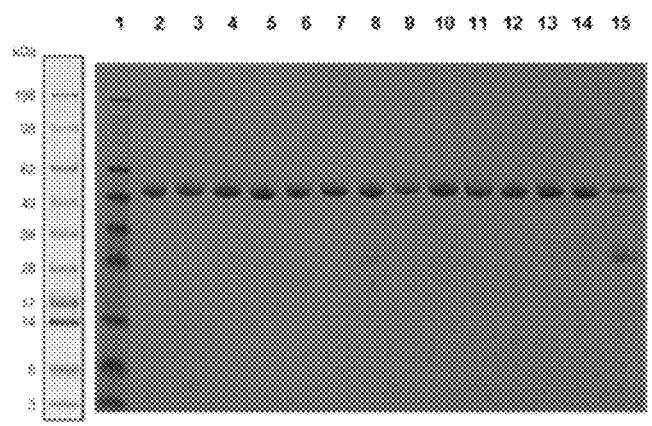
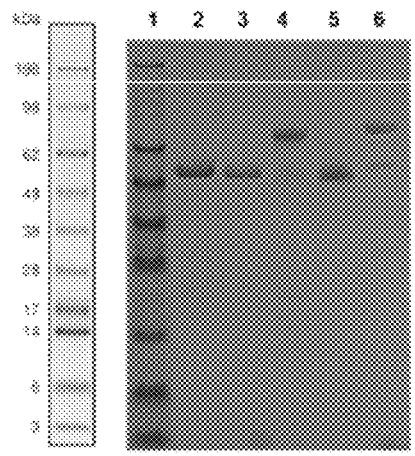
FIGURE 2

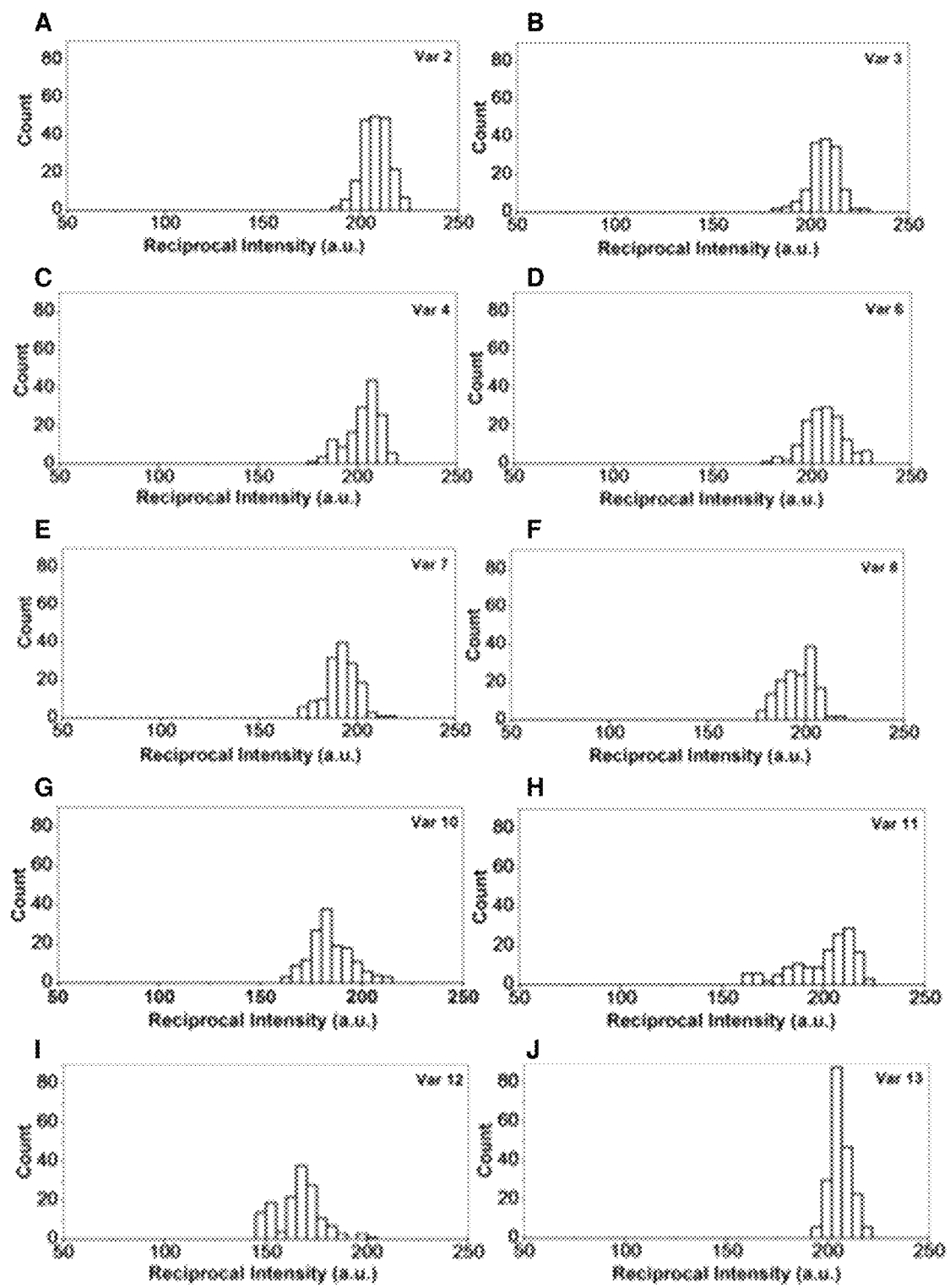
FIGURE 5 (Part 1)

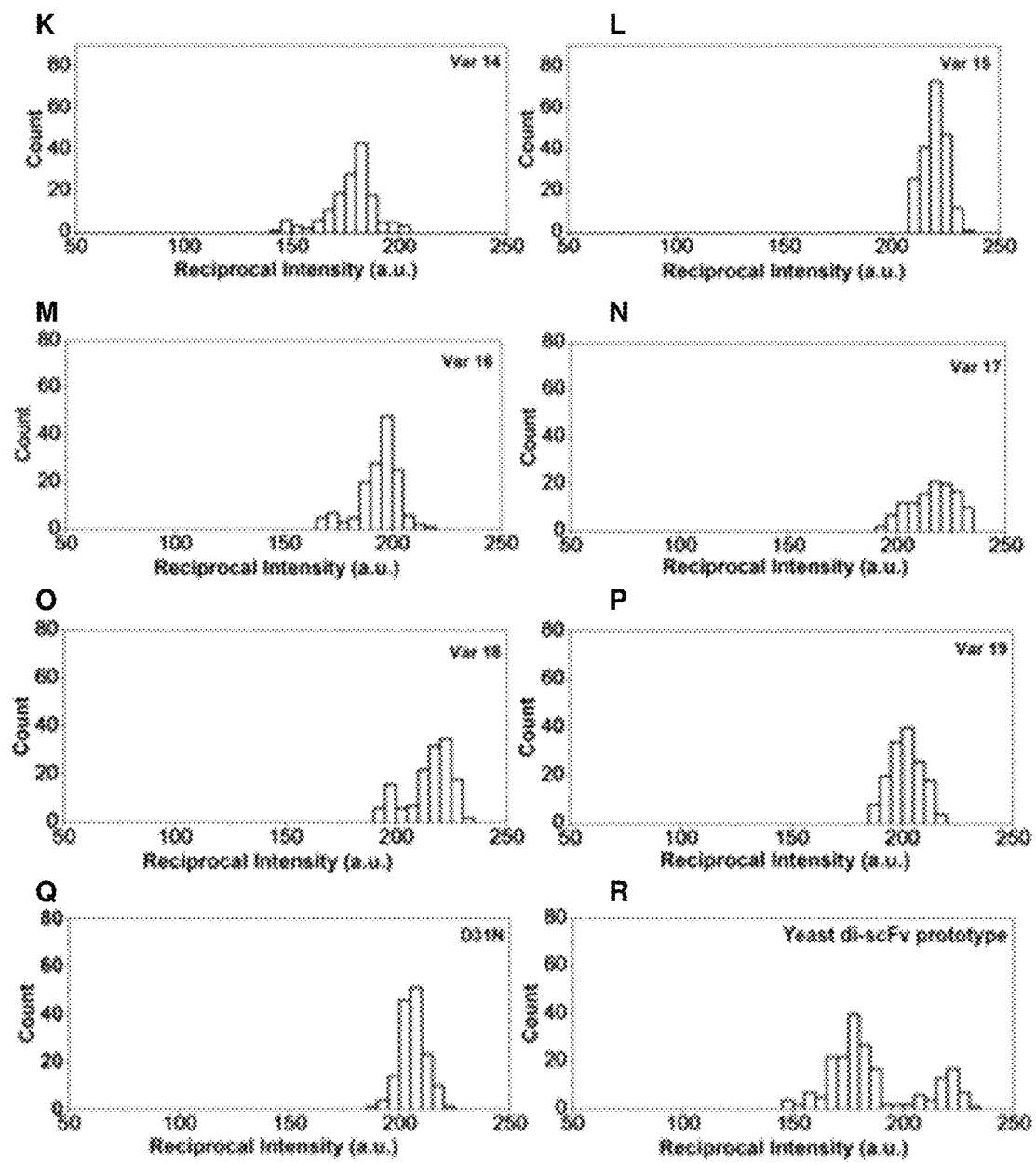
FIGURE 5 (Part 2)

DLD1 Human Colon Cancer Cells
Control                    DX1
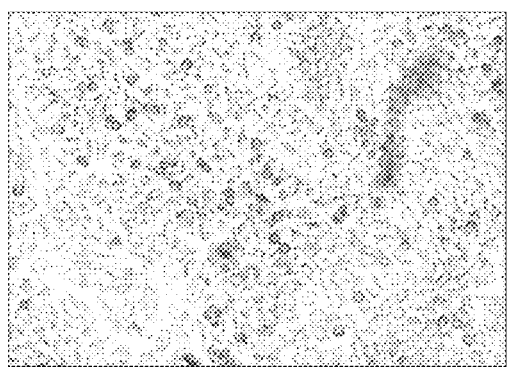 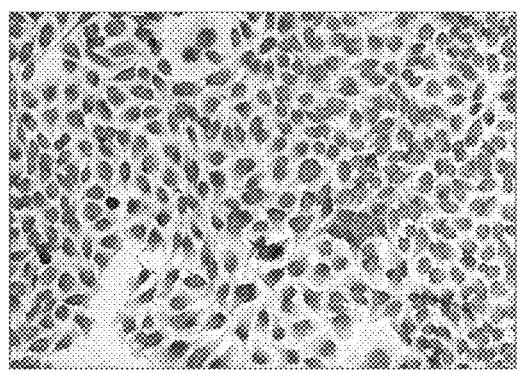
FIGURE 11

```
                           SEQUENCE LISTING

<160> NUMBER OF SEQ ID NOS: 78

<210> SEQ ID NO 1
<211> LENGTH: 5
<212> TYPE: PRT
<213> ORGANISM: Artificial Sequence
<220> FEATURE:
<223> OTHER INFORMATION: Heavy Chain CDR1 KABAT

<400> SEQUENCE: 1

Asn Tyr Gly Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Heavy Chain CDR2 (variants 2 - 4, 6 - 8, 10 -
      12) KABAT

<400> SEQUENCE: 2

Tyr Ile Ser Ser Ser Ser Ser Thr Ile Tyr Tyr Ala Asp Ser Val Lys
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: Heavy Chain CDR2 (variants 13 - 19) KABAT

<400> SEQUENCE: 3

Tyr Ile Ser Ser Gly Ser Ser Thr Ile Tyr Tyr Ala Asp Ser Val Lys
1               5                   10                  15

Gly

<210> SEQ ID NO 4
<211> LENGTH: 7
<212> TYPE: PRT
<213> ORGANISM: Artificial Sequence
<220> FEATURE:
<223> OTHER INFORMATION: Heavy Chain CDR3 KABAT

<400> SEQUENCE: 4

Arg Gly Leu Leu Leu Asp Tyr
1               5

<210> SEQ ID NO 5
<211> LENGTH: 15
<212> TYPE: PRT
<213> ORGANISM: Artificial Sequence
<220> FEATURE:
<223> OTHER INFORMATION: Light Chain CDR1 (variants 2 - 4, 6 - 8, 10 -
      12) KABAT

<400> SEQUENCE: 5

Arg Ala Ser Lys Ser Val Ser Thr Ser Ser Tyr Ser Tyr Met His
1               5                   10                  15
```

```
<210> SEQ ID NO 6
<211> LENGTH: 15
<212> TYPE: PRT
<213> ORGANISM: Artificial Sequence
<220> FEATURE:
<223> OTHER INFORMATION: Light Chain CDR1 (variants 13 - 19) KABAT

<400> SEQUENCE: 6

Arg Ala Ser Lys Thr Val Ser Thr Ser Ser Tyr Ser Tyr Met His
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Light Chain CDR2 KABAT

<400> SEQUENCE: 7

Tyr Ala Ser Tyr Leu Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Light Chain CDR3 KABAT

<400> SEQUENCE: 8

Gln His Ser Arg Glu Phe Pro Trp Thr
1               5

<210> SEQ ID NO 9
<211> LENGTH: 8
<212> TYPE: PRT
<213> ORGANISM: Artificial Sequence
<220> FEATURE:
<223> OTHER INFORMATION: Heavy Chain CDR1 IMGT

<400> SEQUENCE: 9

Gly Phe Thr Phe Ser Asn Tyr Gly
1               5

<210> SEQ ID NO 10
<211> LENGTH: 8
<212> TYPE: PRT
<213> ORGANISM: Artificial Sequence
<220> FEATURE:
<223> OTHER INFORMATION: Heavy Chain CDR2 (variants 2 - 4, 6 - 8, 10 -
      12) IMGT

<400> SEQUENCE: 10

Ile Ser Ser Ser Ser Ser Thr Ile
1               5

<210> SEQ ID NO 11
<211> LENGTH: 8
<212> TYPE: PRT
<213> ORGANISM: Artificial Sequence
<220> FEATURE:
<223> OTHER INFORMATION: Heavy Chain CDR2 (variants 13 - 19) IMGT

<400> SEQUENCE: 11

Ile Ser Ser Gly Ser Ser Thr Ile
1               5
```

```
<210> SEQ ID NO 12
<211> LENGTH: 9
<212> TYPE: PRT
<213> ORGANISM: Artificial Sequence
<220> FEATURE:
<223> OTHER INFORMATION: Heavy Chain CDR3 IMGT

<400> SEQUENCE: 12

Ala Arg Arg Gly Leu Leu Leu Asp Tyr
1               5

<210> SEQ ID NO 13
<211> LENGTH: 10
<212> TYPE: PRT
<213> ORGANISM: Artificial Sequence
<220> FEATURE:
<223> OTHER INFORMATION: Light Chain CDR1 (variants 2 - 4, 6 - 8, 10 -
      12) IMGT

<400> SEQUENCE: 13

Lys Ser Val Ser Thr Ser Ser Tyr Ser Tyr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Light Chain CDR1 (variants 13 - 19) IMGT

<400> SEQUENCE: 14

Lys Thr Val Ser Thr Ser Ser Tyr Ser Tyr
1               5                   10

<210> SEQ ID NO 15
<211> LENGTH: 3
<212> TYPE: PRT
<213> ORGANISM: Artificial Sequence
<220> FEATURE:
<223> OTHER INFORMATION: Light Chain CDR2 IMGT

<400> SEQUENCE: 15

Tyr Ala Ser
1

<210> SEQ ID NO 16
<211> LENGTH: 9
<212> TYPE: PRT
<213> ORGANISM: Artificial Sequence
<220> FEATURE:
<223> OTHER INFORMATION: Light Chain CDR3 IMGT

<400> SEQUENCE: 16

Gln His Ser Arg Glu Phe Pro Trp Thr
1               5

<210> SEQ ID NO 17
<211> LENGTH: 116
<212> TYPE: PRT
<213> ORGANISM: Artificial Sequence
<220> FEATURE:
<223> OTHER INFORMATION: Heavy Chain variable region (variants 2, 6 and
      10)

<400> SEQUENCE: 17

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 18
<211> LENGTH: 116
<212> TYPE: PRT
<213> ORGANISM: Artificial Sequence
<220> FEATURE:
<223> OTHER INFORMATION: Heavy Chain variable region (variants 3, 7 and
      11)

<400> SEQUENCE: 18

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Ser Asn Tyr
                20                  25                  30

Gly Met His Trp Val Arg Gln Ala Pro Glu Lys Gly Leu Glu Trp Val
            35                  40                  45

Ser Tyr Ile Ser Ser Ser Ser Thr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 19
<211> LENGTH: 116
<212> TYPE: PRT
<213> ORGANISM: Artificial Sequence
<220> FEATURE:
<223> OTHER INFORMATION: Heavy Chain variable region (variants 4, 8 and
      12)

<400> SEQUENCE: 19

Glu Val Gln Leu Val Glu Ser Gly Gly Gly Asp Val Lys Pro Gly Gly
 1               5                  10                  15

Ser Leu Arg Leu Ser Cys Ala Ala Ser Gly Phe Thr Phe Ser Asn Tyr
                20                  25                  30

Gly Met His Trp Val Arg Gln Ala Pro Glu Lys Gly Leu Glu Trp Val
            35                  40                  45

Ser Tyr Ile Ser Ser Ser Ser Thr Ile Tyr Tyr Ala Asp Ser Val
 50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 20
<211> LENGTH: 116
<212> TYPE: PRT
<213> ORGANISM: Artificial Sequence
<220> FEATURE:
<223> OTHER INFORMATION: Heavy Chain variable region (variants 6 and 10)

<400> SEQUENCE: 20

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Gly Met His Trp Val Arg Gln Ala Pro Gly Lys Gly Leu Glu Trp Val
         35                  40                  45

Ser Tyr Ile Ser Ser Ser Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 21
<211> LENGTH: 116
<212> TYPE: PRT
<213> ORGANISM: Artificial Sequence
<220> FEATURE:
<223> OTHER INFORMATION: Heavy Chain variable region (variants 13, 16
      and 19)

<400> SEQUENCE: 21

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Gly Met His Trp Val Arg Gln Ala Pro Gly Lys Gly Leu Glu Trp Val
         35                  40                  45

Ser Tyr Ile Ser Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Leu Leu Leu Asp Tyr Trp Gly Gln Gly Thr Thr Val
            100                 105                 110

Thr Val Ser Ser
```

```
            115

<210> SEQ ID NO 22
<211> LENGTH: 116
<212> TYPE: PRT
<213> ORGANISM: Artificial Sequence
<220> FEATURE:
<223> OTHER INFORMATION: Heavy Chain variable region (variants 14 and
      17)

<400> SEQUENCE: 22

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ser Tyr Ile Ser Ser Gly Ser Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 23
<211> LENGTH: 116
<212> TYPE: PRT
<213> ORGANISM: Artificial Sequence
<220> FEATURE:
<223> OTHER INFORMATION: Heavy Chain variable region (variants 15 and
      18)

<400> SEQUENCE: 23

Glu Val Gln Leu Val Glu Ser Gly Gly Gly Asp Val Lys Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ser Tyr Ile Ser Ser Gly Ser Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser
        115

<210> SEQ ID NO 24
<211> LENGTH: 111
<212> TYPE: PRT
<213> ORGANISM: Artificial Sequence
<220> FEATURE:
<223> OTHER INFORMATION: Light Chain variable region (variants 2, 3 and
```

4)

<400> SEQUENCE: 24

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys
            100                 105                 110

<210> SEQ ID NO 25
<211> LENGTH: 111
<212> TYPE: PRT
<213> ORGANISM: Artificial Sequence
<220> FEATURE:
<223> OTHER INFORMATION: Light Chain variable region (variants 6, 7 and
      8)

<400> SEQUENCE: 25

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys
            100                 105                 110

<210> SEQ ID NO 26
<211> LENGTH: 111
<212> TYPE: PRT
<213> ORGANISM: Artificial Sequence
<220> FEATURE:
<223> OTHER INFORMATION: Light Chain variable region (variants 10, 11
      and 12)

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Ser Tyr Ser Tyr Met His Trp Tyr Gln Gln Lys Pro Gly Lys Ala Pro
        35                  40                  45

Lys Leu Leu Ile Lys Tyr Ala Ser Tyr Leu Glu Ser Gly Val Pro Ser
    50                  55                  60

```
Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                 85                  90                  95

Glu Phe Pro Trp Thr Phe Gly Gly Gly Thr Lys Val Glu Ile Lys
            100                 105                 110

<210> SEQ ID NO 27
<211> LENGTH: 111
<212> TYPE: PRT
<213> ORGANISM: Artificial Sequence
<220> FEATURE:
<223> OTHER INFORMATION: Light Chain variable region (variants 13, 14
      and 15)

<400> SEQUENCE: 27

Asp Ile Gln Met Thr Gln Ser Pro Ser Ser Leu Ser Ala Ser Leu Gly
 1               5                  10                  15

Asp Arg Ala Thr Ile Thr Cys Arg Ala Ser Lys Thr Val Ser Thr Ser
                 20                  25                  30

Ser Tyr Ser Tyr Met His Trp Tyr Gln Gln Lys Pro Gly Gln Pro Pro
             35                  40                  45

Lys Leu Leu Ile Lys Tyr Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Ala Ala Thr Tyr Tyr Cys Gln His Ser Arg
                 85                  90                  95

Glu Phe Pro Trp Thr Phe Gly Gly Gly Thr Lys Val Glu Ile Lys
            100                 105                 110

<210> SEQ ID NO 28
<211> LENGTH: 111
<212> TYPE: PRT
<213> ORGANISM: Artificial Sequence
<220> FEATURE:
<223> OTHER INFORMATION: Light Chain variable region (variants 16, 17
      and 18)

<400> SEQUENCE: 28

Asp Ile Gln Met Thr Gln Ser Pro Ser Ser Leu Ser Ala Ser Val Gly
 1               5                  10                  15

Asp Arg Val Thr Ile Thr Cys Arg Ala Ser Lys Thr Val Ser Thr Ser
                 20                  25                  30

Ser Tyr Ser Tyr Met His Trp Tyr Gln Gln Lys Pro Gly Lys Ala Pro
             35                  40                  45

Lys Leu Leu Ile Lys Tyr Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                 85                  90                  95

Glu Phe Pro Trp Thr Phe Gly Gly Gly Thr Lys Val Glu Ile Lys
            100                 105                 110

<210> SEQ ID NO 29
<211> LENGTH: 111
<212> TYPE: PRT
<213> ORGANISM: Artificial Sequence
```

```
<220> FEATURE:
<223> OTHER INFORMATION: Light Chain variable region (variant 19)

<400> SEQUENCE: 29

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Thr Val Ser Thr Ser
            20                  25                  30

Ser Tyr Ser Tyr Met His Trp Tyr Gln Gln Lys Pro Gly Gln Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys
            100                 105                 110

<210> SEQ ID NO 30
<211> LENGTH: 21
<212> TYPE: PRT
<213> ORGANISM: Artificial Sequence
<220> FEATURE:
<223> OTHER INFORMATION: Linker sequence 1

<400> SEQUENCE: 30

Arg Ala Asp Ala Ala Pro Gly Gly Gly Ser Gly Gly Gly Gly Ser
1               5                   10                  15

Gly Gly Gly Gly Ser
            20

<210> SEQ ID NO 31
<211> LENGTH: 19
<212> TYPE: PRT
<213> ORGANISM: Artificial Sequence
<220> FEATURE:
<223> OTHER INFORMATION: Linker sequence 2

<400> SEQUENCE: 31

Ala Ser Thr Lys Gly Pro Ser Val Phe Pro Leu Ala Pro Leu Glu Ser
1               5                   10                  15

Ser Gly Ser

<210> SEQ ID NO 32
<211> LENGTH: 515
<212> TYPE: PRT
<213> ORGANISM: Artificial Sequence
<220> FEATURE:
<223> OTHER INFORMATION: Variant 2

<400> SEQUENCE: 32

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
    50                  55                  60
```

-continued

```
Arg Phe Ser Gly Ser Gly Ser Gly Thr Asp Phe Thr Leu Thr Ile Ser
 65                  70                  75                  80

Ser Leu Gln Pro Glu Asp Ala Ala Thr Tyr Tyr Cys Gln His Ser Arg
                 85                  90                  95

Glu Phe Pro Trp Thr Phe Gly Gly Gly Thr Lys Val Glu Ile Lys Arg
            100                 105                 110

Ala Asp Ala Ala Pro Gly Gly Gly Ser Gly Gly Gly Ser Gly
        115                 120                 125

Gly Gly Gly Ser Glu Val Gln Leu Val Glu Ser Gly Gly Leu Val
    130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
                165                 170                 175

Leu Glu Trp Val Ser Tyr Ile Ser Ser Ser Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Leu Gly Asp Arg Ala Thr Ile
        275                 280                 285

Thr Cys Arg Ala Ser Lys Ser Val Ser Thr Ser Ser Tyr Ser Tyr Met
    290                 295                 300

His Trp Tyr Gln Gln Lys Pro Gly Gln Pro Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Ala Ala Thr Tyr Tyr Cys Gln His Ser Arg Glu Phe Pro Trp Thr
        355                 360                 365

Phe Gly Gly Gly Thr Lys Val Glu Ile Lys Arg Ala Asp Ala Ala Pro
    370                 375                 380

Gly Gly Gly Gly Ser Gly Gly Gly Ser Gly Gly Gly Ser Glu
385                 390                 395                 400

Val Gln Leu Val Glu Ser Gly Gly Leu Val Gln Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Gly Lys Gly Leu Glu Trp Val Ser
        435                 440                 445

Tyr Ile Ser Ser Ser Ser Thr Ile Tyr Tyr Ala Asp Ser Val Lys
    450                 455                 460

Gly Arg Phe Thr Ile Ser Arg Asp Asn Ala Lys Asn Ser Leu Tyr Leu
465                 470                 475                 480

Gln Met Asn Ser Leu Arg Ala Glu Asp Thr Ala Val Tyr Tyr Cys Ala
```

```
                        485                 490                 495
Arg Arg Gly Leu Leu Asp Tyr Trp Gly Gln Gly Thr Thr Val Thr
                500                 505                 510

Val Ser Ser
        515

<210> SEQ ID NO 33
<211> LENGTH: 515
<212> TYPE: PRT
<213> ORGANISM: Artificial Sequence
<220> FEATURE:
<223> OTHER INFORMATION: Variant 3

<400> SEQUENCE: 33

Asp Ile Gln Met Thr Gln Ser Pro Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125

Gly Gly Gly Ser Glu Val Gln Leu Val Glu Ser Gly Gly Gly Val Val
    130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Ser Ser Thr Ile Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Gly Ser Asp Ile Gln Met Thr
            260                 265                 270

Gln Ser Pro Ser Ser Leu Ser Ala Ser Leu Gly Asp Arg Ala Thr Ile
        275                 280                 285

Thr Cys Arg Ala Ser Lys Ser Val Ser Thr Ser Ser Tyr Ser Tyr Met
    290                 295                 300

His Trp Tyr Gln Gln Lys Pro Gly Gln Pro Pro Lys Leu Leu Ile Lys
305                 310                 315                 320

Tyr Ala Ser Tyr Leu Glu Ser Gly Val Pro Ser Arg Phe Ser Gly Ser
```

```
                  325                 330                 335
Gly Ser Gly Thr Asp Phe Thr Leu Thr Ile Ser Ser Leu Gln Pro Glu
            340                 345                 350

Asp Ala Ala Thr Tyr Tyr Cys Gln His Ser Arg Glu Phe Pro Trp Thr
            355                 360                 365

Phe Gly Gly Gly Thr Lys Val Glu Ile Lys Arg Ala Asp Ala Ala Pro
            370                 375                 380

Gly Gly Gly Gly Ser Gly Gly Gly Ser Gly Gly Gly Gly Ser Glu
385                 390                 395                 400

Val Gln Leu Val Glu Ser Gly Gly Val Val Gln Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Glu Lys Gly Leu Glu Trp Val Ser
            435                 440                 445

Tyr Ile Ser Ser Ser Ser Thr Ile Tyr Tyr Ala Asp Ser Val Lys
            450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
                500                 505                 510

Val Ser Ser
        515

<210> SEQ ID NO 34
<211> LENGTH: 515
<212> TYPE: PRT
<213> ORGANISM: Artificial Sequence
<220> FEATURE:
<223> OTHER INFORMATION: Variant 4

<400> SEQUENCE: 34

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys Arg
            100                 105                 110

Ala Asp Ala Ala Pro Gly Gly Gly Gly Ser Gly Gly Gly Ser Gly
            115                 120                 125

Gly Gly Gly Ser Glu Val Gln Leu Val Glu Ser Gly Gly Asp Val
        130                 135                 140

Lys Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
```

```
                165                 170                 175
Leu Glu Trp Val Ser Tyr Ile Ser Ser Ser Ser Thr Ile Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Leu Gly Asp Arg Ala Thr Ile
        275                 280                 285

Thr Cys Arg Ala Ser Lys Ser Val Ser Thr Ser Ser Tyr Ser Tyr Met
    290                 295                 300

His Trp Tyr Gln Gln Lys Pro Gly Gln Pro Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Ala Ala Thr Tyr Tyr Cys Gln His Ser Arg Glu Phe Pro Trp Thr
        355                 360                 365

Phe Gly Gly Gly Thr Lys Val Glu Ile Lys Arg Ala Asp Ala Ala Pro
    370                 375                 380

Gly Gly Gly Gly Ser Gly Gly Gly Ser Gly Gly Gly Gly Ser Glu
385                 390                 395                 400

Val Gln Leu Val Glu Ser Gly Gly Asp Val Lys Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Glu Lys Gly Leu Glu Trp Val Ser
        435                 440                 445

Tyr Ile Ser Ser Ser Ser Thr Ile Tyr Tyr Ala Asp Ser Val Lys
    450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Asp Tyr Trp Gly Gln Gly Thr Thr Val Thr
            500                 505                 510

Val Ser Ser
        515

<210> SEQ ID NO 35
<211> LENGTH: 515
<212> TYPE: PRT
<213> ORGANISM: Artificial Sequence
<220> FEATURE:
<223> OTHER INFORMATION: Variant 6

<400> SEQUENCE: 35

Asp Ile Gln Met Thr Gln Ser Pro Ser Ser Leu Ser Ala Ser Leu Gly
```

```
1               5                    10                   15
Asp Arg Ala Thr Ile Thr Cys Arg Ala Ser Lys Ser Val Ser Thr Ser
                20                  25                  30

Ser Tyr Ser Tyr Met His Trp Tyr Gln Gln Lys Pro Gly Gln Ala Pro
                35                  40                  45

Lys Leu Leu Ile Lys Tyr Ala Ser Tyr Leu Glu Ser Gly Val Pro Ser
            50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
                100                 105                 110

Ala Asp Ala Ala Pro Gly Gly Gly Gly Ser Gly Gly Gly Gly Ser Gly
                115                 120                 125

Gly Gly Gly Ser Glu Val Gln Leu Val Glu Ser Gly Gly Gly Leu Val
            130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
                165                 170                 175

Leu Glu Trp Val Ser Tyr Ile Ser Ser Ser Ser Ser Thr Ile Tyr Tyr
                180                 185                 190

Ala Asp Ser Val Lys Gly Arg Phe Thr Ile Ser Arg Asp Asn Ala Lys
                195                 200                 205

Asn Ser Leu Tyr Leu Gln Met Asn Ser Leu Arg Ala Glu Asp Thr Ala
            210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
                260                 265                 270

Gln Ser Pro Ser Ser Leu Ser Ala Ser Leu Gly Asp Arg Ala Thr Ile
                275                 280                 285

Thr Cys Arg Ala Ser Lys Ser Val Ser Thr Ser Ser Tyr Ser Tyr Met
                290                 295                 300

His Trp Tyr Gln Gln Lys Pro Gly Gln Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
                340                 345                 350

Asp Phe Ala Thr Tyr Tyr Cys Gln His Ser Arg Glu Phe Pro Trp Thr
                355                 360                 365

Phe Gly Gln Gly Thr Lys Val Glu Ile Lys Arg Ala Asp Ala Ala Pro
            370                 375                 380

Gly Gly Gly Gly Ser Gly Gly Gly Gly Ser Gly Gly Gly Gly Ser Glu
385                 390                 395                 400

Val Gln Leu Val Glu Ser Gly Gly Gly Leu Val Gln Pro Gly Gly Ser
                405                 410                 415

Leu Arg Leu Ser Cys Ala Ala Ser Gly Phe Thr Phe Ser Asn Tyr Gly
                420                 425                 430
```

```
Met His Trp Val Arg Gln Ala Pro Gly Lys Gly Leu Glu Trp Val Ser
        435                 440                 445

Tyr Ile Ser Ser Ser Ser Thr Ile Tyr Tyr Ala Asp Ser Val Lys
    450                 455                 460

Gly Arg Phe Thr Ile Ser Arg Asp Asn Ala Lys Asn Ser Leu Tyr Leu
465                 470                 475                 480

Gln Met Asn Ser Leu Arg Ala Glu Asp Thr Ala Val Tyr Tyr Cys Ala
            485                 490                 495

Arg Arg Gly Leu Leu Leu Asp Tyr Trp Gly Gln Gly Thr Thr Val Thr
                500                 505                 510

Val Ser Ser
        515

<210> SEQ ID NO 36
<211> LENGTH: 515
<212> TYPE: PRT
<213> ORGANISM: Artificial Sequence
<220> FEATURE:
<223> OTHER INFORMATION: Variant 7

<400> SEQUENCE: 36

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125

Gly Gly Gly Ser Glu Val Gln Leu Val Glu Ser Gly Gly Gly Val Val
    130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Ser Ser Thr Ile Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270
```

```
Gln Ser Pro Ser Ser Leu Ser Ala Ser Leu Gly Asp Arg Ala Thr Ile
            275                 280                 285

Thr Cys Arg Ala Ser Lys Ser Val Ser Thr Ser Ser Tyr Ser Tyr Met
290                 295                 300

His Trp Tyr Gln Gln Lys Pro Gly Gln Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
        355                 360                 365

Phe Gly Gln Gly Thr Lys Val Glu Ile Lys Arg Ala Asp Ala Ala Pro
370                 375                 380

Gly Gly Gly Gly Ser Gly Gly Gly Ser Gly Gly Gly Ser Glu
385                 390                 395                 400

Val Gln Leu Val Glu Ser Gly Gly Val Val Gln Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Glu Lys Gly Leu Glu Trp Val Ser
        435                 440                 445

Tyr Ile Ser Ser Ser Ser Thr Ile Tyr Tyr Ala Asp Ser Val Lys
450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
            500                 505                 510

Val Ser Ser
        515

<210> SEQ ID NO 37
<211> LENGTH: 515
<212> TYPE: PRT
<213> ORGANISM: Artificial Sequence
<220> FEATURE:
<223> OTHER INFORMATION: Variant 8

<400> SEQUENCE: 37

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110
```

Ala Asp Ala Ala Pro Gly Gly Gly Ser Gly Gly Gly Ser Gly
        115                 120                 125

Gly Gly Gly Ser Glu Val Gln Leu Val Glu Ser Gly Gly Asp Val
    130                 135                 140

Lys Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Ser Ser Thr Ile Tyr Tyr
                180                 185                 190

Ala Asp Ser Val Lys Gly Arg Phe Thr Ile Ser Arg Asp Asn Ser Lys
                195                 200                 205

Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
                260                 265                 270

Gln Ser Pro Ser Ser Leu Ser Ala Ser Leu Gly Asp Arg Ala Thr Ile
            275                 280                 285

Thr Cys Arg Ala Ser Lys Ser Val Ser Thr Ser Ser Tyr Ser Tyr Met
    290                 295                 300

His Trp Tyr Gln Gln Lys Pro Gly Gln Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
        355                 360                 365

Phe Gly Gln Gly Thr Lys Val Glu Ile Lys Arg Ala Asp Ala Ala Pro
    370                 375                 380

Gly Gly Gly Gly Ser Gly Gly Gly Ser Gly Gly Gly Ser Glu
385                 390                 395                 400

Val Gln Leu Val Glu Ser Gly Gly Asp Val Lys Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Glu Lys Gly Leu Glu Trp Val Ser
    435                 440                 445

Tyr Ile Ser Ser Ser Ser Thr Ile Tyr Tyr Ala Asp Ser Val Lys
    450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
            500                 505                 510

Val Ser Ser
        515

-continued

```
<210> SEQ ID NO 38
<211> LENGTH: 515
<212> TYPE: PRT
<213> ORGANISM: Artificial Sequence
<220> FEATURE:
<223> OTHER INFORMATION: Variant 10

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Ser Tyr Ser Tyr Met His Trp Tyr Gln Gln Lys Pro Gly Lys Ala Pro
        35                  40                  45

Lys Leu Leu Ile Lys Tyr Ala Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125

Gly Gly Gly Ser Glu Val Gln Leu Val Glu Ser Gly Gly Gly Leu Val
130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
                165                 170                 175

Leu Glu Trp Val Ser Tyr Ile Ser Ser Ser Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
210                 215                 220

Val Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Val Gly Asp Arg Val Thr Ile
        275                 280                 285

Thr Cys Arg Ala Ser Lys Ser Val Ser Thr Ser Ser Tyr Ser Tyr Met
290                 295                 300

His Trp Tyr Gln Gln Lys Pro Gly Lys Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
        355                 360                 365
```

```
Phe Gly Gln Gly Thr Lys Val Glu Ile Lys Arg Ala Asp Ala Ala Pro
    370                 375                 380
Gly Gly Gly Gly Ser Gly Gly Gly Ser Gly Gly Gly Gly Ser Glu
385                 390                 395                 400
Val Gln Leu Val Glu Ser Gly Gly Leu Val Gln Pro Gly Gly Ser
                405                 410                 415
Leu Arg Leu Ser Cys Ala Ala Ser Gly Phe Thr Phe Ser Asn Tyr Gly
                420                 425                 430
Met His Trp Val Arg Gln Ala Pro Gly Lys Gly Leu Glu Trp Val Ser
            435                 440                 445
Tyr Ile Ser Ser Ser Ser Thr Ile Tyr Tyr Ala Asp Ser Val Lys
    450                 455                 460
Gly Arg Phe Thr Ile Ser Arg Asp Asn Ala Lys Asn Ser Leu Tyr Leu
465                 470                 475                 480
Gln Met Asn Ser Leu Arg Ala Glu Asp Thr Ala Val Tyr Tyr Cys Ala
                485                 490                 495
Arg Arg Gly Leu Leu Leu Asp Tyr Trp Gly Gln Gly Thr Thr Val Thr
                500                 505                 510
Val Ser Ser
        515

<210> SEQ ID NO 39
<211> LENGTH: 515
<212> TYPE: PRT
<213> ORGANISM: Artificial Sequence
<220> FEATURE:
<223> OTHER INFORMATION: Variant 11

<400> SEQUENCE: 39

Asp Ile Gln Met Thr Gln Ser Pro Ser Ser Leu Ser Ala Ser Val Gly
1               5                   10                  15
Asp Arg Val Thr Ile Thr Cys Arg Ala Ser Lys Ser Val Ser Thr Ser
                20                  25                  30
Ser Tyr Ser Tyr Met His Trp Tyr Gln Gln Lys Pro Gly Lys Ala Pro
            35                  40                  45
Lys Leu Leu Ile Lys Tyr Ala Ser Tyr Leu Glu Ser Gly Val Pro Ser
    50                  55                  60
Arg Phe Ser Gly Ser Gly Ser Gly Thr Asp Phe Thr Leu Thr Ile Ser
65                  70                  75                  80
Ser Leu Gln Pro Glu Asp Phe Ala Thr Tyr Tyr Cys Gln His Ser Arg
                85                  90                  95
Glu Phe Pro Trp Thr Phe Gly Gln Gly Thr Lys Val Glu Ile Lys Arg
                100                 105                 110
Ala Asp Ala Ala Pro Gly Gly Gly Gly Ser Gly Gly Gly Gly Ser Gly
            115                 120                 125
Gly Gly Gly Ser Glu Val Gln Leu Val Glu Ser Gly Gly Gly Val Val
130                 135                 140
Gln Pro Gly Gly Ser Leu Arg Leu Ser Cys Ala Ala Ser Gly Phe Thr
145                 150                 155                 160
Phe Ser Asn Tyr Gly Met His Trp Val Arg Gln Ala Pro Glu Lys Gly
                165                 170                 175
Leu Glu Trp Val Ser Tyr Ile Ser Ser Ser Ser Thr Ile Tyr Tyr
                180                 185                 190
Ala Asp Ser Val Lys Gly Arg Phe Thr Ile Ser Arg Asp Asn Ser Lys
            195                 200                 205
```

```
Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Val Gly Asp Arg Val Thr Ile
        275                 280                 285

Thr Cys Arg Ala Ser Lys Ser Val Ser Thr Ser Ser Tyr Ser Tyr Met
    290                 295                 300

His Trp Tyr Gln Gln Lys Pro Gly Lys Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
        355                 360                 365

Phe Gly Gln Gly Thr Lys Val Glu Ile Lys Arg Ala Asp Ala Ala Pro
    370                 375                 380

Gly Gly Gly Gly Ser Gly Gly Gly Ser Gly Gly Gly Gly Ser Glu
385                 390                 395                 400

Val Gln Leu Val Glu Ser Gly Gly Val Val Gln Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Glu Lys Gly Leu Glu Trp Val Ser
        435                 440                 445

Tyr Ile Ser Ser Ser Ser Ser Thr Ile Tyr Tyr Ala Asp Ser Val Lys
    450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Asp Tyr Trp Gly Gln Gly Thr Thr Val Thr
            500                 505                 510

Val Ser Ser
        515

<210> SEQ ID NO 40
<211> LENGTH: 515
<212> TYPE: PRT
<213> ORGANISM: Artificial Sequence
<220> FEATURE:
<223> OTHER INFORMATION: Variant 12

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Ser Tyr Ser Tyr Met His Trp Tyr Gln Gln Lys Pro Gly Lys Ala Pro
        35                  40                  45
```

Lys Leu Leu Ile Lys Tyr Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                 85                  90                  95

Glu Phe Pro Trp Thr Phe Gly Gln Gly Thr Lys Val Glu Ile Lys Arg
                100                 105                 110

Ala Asp Ala Ala Pro Gly Gly Gly Ser Gly Gly Gly Ser Gly
                115                 120                 125

Gly Gly Gly Ser Glu Val Gln Leu Val Glu Ser Gly Gly Gly Asp Val
130                 135                 140

Lys Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Ser Ser Thr Ile Tyr Tyr
                180                 185                 190

Ala Asp Ser Val Lys Gly Arg Phe Thr Ile Ser Arg Asp Asn Ser Lys
                195                 200                 205

Asn Thr Leu Tyr Leu Gln Met Asn Ser Leu Arg Ala Glu Asp Thr Ala
210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
                260                 265                 270

Gln Ser Pro Ser Ser Leu Ser Ala Ser Val Gly Asp Arg Val Thr Ile
                275                 280                 285

Thr Cys Arg Ala Ser Lys Ser Val Ser Thr Ser Ser Tyr Ser Tyr Met
290                 295                 300

His Trp Tyr Gln Gln Lys Pro Gly Lys Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
                340                 345                 350

Asp Phe Ala Thr Tyr Tyr Cys Gln His Ser Arg Glu Phe Pro Trp Thr
                355                 360                 365

Phe Gly Gln Gly Thr Lys Val Glu Ile Lys Arg Ala Asp Ala Ala Pro
                370                 375                 380

Gly Gly Gly Gly Ser Gly Gly Gly Gly Ser Gly Gly Gly Gly Ser Glu
385                 390                 395                 400

Val Gln Leu Val Glu Ser Gly Gly Gly Asp Val Lys Pro Gly Gly Ser
                405                 410                 415

Leu Arg Leu Ser Cys Ala Ala Ser Gly Phe Thr Phe Ser Asn Tyr Gly
                420                 425                 430

Met His Trp Val Arg Gln Ala Pro Glu Lys Gly Leu Glu Trp Val Ser
                435                 440                 445

Tyr Ile Ser Ser Ser Ser Thr Ile Tyr Tyr Ala Asp Ser Val Lys
450                 455                 460

Gly Arg Phe Thr Ile Ser Arg Asp Asn Ser Lys Asn Thr Leu Tyr Leu

```
            465                 470                 475                 480
Gln Met Asn Ser Leu Arg Ala Glu Asp Thr Ala Val Tyr Tyr Cys Ala
                    485                 490                 495

Arg Arg Gly Leu Leu Asp Tyr Trp Gly Gln Gly Thr Thr Val Thr
            500                 505                 510

Val Ser Ser
        515

<210> SEQ ID NO 41
<211> LENGTH: 515
<212> TYPE: PRT
<213> ORGANISM: Artificial Sequence
<220> FEATURE:
<223> OTHER INFORMATION: Variant 13

<400> SEQUENCE: 41

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Thr Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
                165                 170                 175

Leu Glu Trp Val Ser Tyr Ile Ser Ser Gly Ser Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
    210                 215                 220

Val Tyr Tyr Cys Ala Arg Arg Gly Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Leu Gly Asp Arg Ala Thr Ile
        275                 280                 285

Thr Cys Arg Ala Ser Lys Thr Val Ser Thr Ser Ser Tyr Ser Tyr Met
    290                 295                 300

His Trp Tyr Gln Gln Lys Pro Gly Gln Pro Pro Lys Leu Leu Ile Lys
```

```
                305                 310                 315                 320
        Tyr Ala Ser Tyr Leu Glu Ser Gly Val Pro Ser Arg Phe Ser Gly Ser
                        325                 330                 335

Gly Ser Gly Thr Asp Phe Thr Leu Thr Ile Ser Ser Leu Gln Pro Glu
                        340                 345                 350

Asp Ala Ala Thr Tyr Tyr Cys Gln His Ser Arg Glu Phe Pro Trp Thr
                        355                 360                 365

Phe Gly Gly Gly Thr Lys Val Glu Ile Lys Arg Ala Asp Ala Ala Pro
                        370                 375                 380

Gly Gly Gly Gly Ser Gly Gly Gly Ser Gly Gly Gly Gly Ser Glu
        385                 390                 395                 400

Val Gln Leu Val Glu Ser Gly Gly Leu Val Gln Pro Gly Gly Ser
                        405                 410                 415

Leu Arg Leu Ser Cys Ala Ala Ser Gly Phe Thr Phe Ser Asn Tyr Gly
                        420                 425                 430

Met His Trp Val Arg Gln Ala Pro Gly Lys Gly Leu Glu Trp Val Ser
                        435                 440                 445

Tyr Ile Ser Ser Gly Ser Ser Thr Ile Tyr Tyr Ala Asp Ser Val Lys
                        450                 455                 460

Gly Arg Phe Thr Ile Ser Arg Asp Asn Ala Lys Asn Ser Leu Tyr Leu
        465                 470                 475                 480

Gln Met Asn Ser Leu Arg Ala Glu Asp Thr Ala Val Tyr Tyr Cys Ala
                        485                 490                 495

Arg Arg Gly Leu Leu Leu Asp Tyr Trp Gly Gln Gly Thr Thr Val Thr
                        500                 505                 510

Val Ser Ser
                515

<210> SEQ ID NO 42
<211> LENGTH: 515
<212> TYPE: PRT
<213> ORGANISM: Artificial Sequence
<220> FEATURE:
<223> OTHER INFORMATION: Variant 14

<400> SEQUENCE: 42

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Thr Val Ser Thr Ser
                20                  25                  30

Ser Tyr Ser Tyr Met His Trp Tyr Gln Gln Lys Pro Gly Gln Pro Pro
                35                  40                  45

Lys Leu Leu Ile Lys Tyr Ala Ser Tyr Leu Glu Ser Gly Val Pro Ser
            50                  55                  60

Arg Phe Ser Gly Ser Gly Ser Gly Thr Asp Phe Thr Leu Thr Ile Ser
65              70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys Arg
                100                 105                 110

Ala Asp Ala Ala Pro Gly Gly Gly Gly Ser Gly Gly Gly Ser Gly
                115                 120                 125

Gly Gly Gly Ser Glu Val Gln Leu Val Glu Ser Gly Gly Gly Val Val
            130                 135                 140

Gln Pro Gly Gly Ser Leu Arg Leu Ser Cys Ala Ala Ser Gly Phe Thr
```

```
            145                 150                 155                 160
        Phe Ser Asn Tyr Gly Met His Trp Val Arg Gln Ala Pro Glu Lys Gly
                        165                 170                 175
        Leu Glu Trp Val Ser Tyr Ile Ser Ser Gly Ser Ser Thr Ile Tyr Tyr
                        180                 185                 190
        Ala Asp Ser Val Lys Gly Arg Phe Thr Ile Ser Arg Asp Asn Ser Lys
                        195                 200                 205
        Asn Thr Leu Tyr Leu Gln Met Asn Ser Leu Arg Ala Glu Asp Thr Ala
                        210                 215                 220
        Val Tyr Tyr Cys Ala Arg Arg Gly Leu Leu Asp Tyr Trp Gly Gln
        225                 230                 235                 240
        Gly Thr Thr Val Thr Val Ser Ser Ala Ser Thr Lys Gly Pro Ser Val
                            245                 250                 255
        Phe Pro Leu Ala Pro Leu Glu Ser Gly Ser Asp Ile Gln Met Thr
                        260                 265                 270
        Gln Ser Pro Ser Ser Leu Ser Ala Ser Leu Gly Asp Arg Ala Thr Ile
                        275                 280                 285
        Thr Cys Arg Ala Ser Lys Thr Val Ser Thr Ser Ser Tyr Ser Tyr Met
                290                 295                 300
        His Trp Tyr Gln Gln Lys Pro Gly Gln Pro Pro Lys Leu Leu Ile Lys
        305                 310                 315                 320
        Tyr Ala Ser Tyr Leu Glu Ser Gly Val Pro Ser Arg Phe Ser Gly Ser
                        325                 330                 335
        Gly Ser Gly Thr Asp Phe Thr Leu Thr Ile Ser Ser Leu Gln Pro Glu
                        340                 345                 350
        Asp Ala Ala Thr Tyr Tyr Cys Gln His Ser Arg Glu Phe Pro Trp Thr
                        355                 360                 365
        Phe Gly Gly Gly Thr Lys Val Glu Ile Lys Arg Ala Asp Ala Ala Pro
                        370                 375                 380
        Gly Gly Gly Gly Ser Gly Gly Gly Ser Gly Gly Gly Ser Glu
        385                 390                 395                 400
        Val Gln Leu Val Glu Ser Gly Gly Val Val Gln Pro Gly Gly Ser
                        405                 410                 415
        Leu Arg Leu Ser Cys Ala Ala Ser Gly Phe Thr Phe Ser Asn Tyr Gly
                        420                 425                 430
        Met His Trp Val Arg Gln Ala Pro Glu Lys Gly Leu Glu Trp Val Ser
                        435                 440                 445
        Tyr Ile Ser Ser Gly Ser Ser Thr Ile Tyr Tyr Ala Asp Ser Val Lys
                        450                 455                 460
        Gly Arg Phe Thr Ile Ser Arg Asp Asn Ser Lys Asn Thr Leu Tyr Leu
        465                 470                 475                 480
        Gln Met Asn Ser Leu Arg Ala Glu Asp Thr Ala Val Tyr Tyr Cys Ala
                        485                 490                 495
        Arg Arg Gly Leu Leu Leu Asp Tyr Trp Gly Gln Gly Thr Thr Val Thr
                        500                 505                 510
        Val Ser Ser
                515

<210> SEQ ID NO 43
<211> LENGTH: 515
<212> TYPE: PRT
<213> ORGANISM: Artificial Sequence
<220> FEATURE:
<223> OTHER INFORMATION: Variant 15
```

<400> SEQUENCE: 43

```
Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Thr Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln His Ser Arg
                85                  90                  95

Glu Phe Pro Trp Thr Phe Gly Gly Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125

Gly Gly Gly Ser Glu Val Gln Leu Val Glu Ser Gly Gly Gly Asp Val
    130                 135                 140

Lys Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
            165                 170                 175

Leu Glu Trp Val Ser Tyr Ile Ser Ser Gly Ser Ser Thr Ile Tyr Tyr
        180                 185                 190

Ala Asp Ser Val Lys Gly Arg Phe Thr Ile Ser Arg Asp Asn Ser Lys
    195                 200                 205

Asn Thr Leu Tyr Leu Gln Met Asn Ser Leu Arg Ala Glu Asp Thr Ala
210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
            245                 250                 255

Phe Pro Leu Ala Pro Leu Glu Ser Ser Gly Ser Asp Ile Gln Met Thr
        260                 265                 270

Gln Ser Pro Ser Ser Leu Ser Ala Ser Leu Gly Asp Arg Ala Thr Ile
    275                 280                 285

Thr Cys Arg Ala Ser Lys Thr Val Ser Thr Ser Ser Tyr Ser Tyr Met
290                 295                 300

His Trp Tyr Gln Gln Lys Pro Gly Gln Pro Pro Lys Leu Leu Ile Lys
305                 310                 315                 320

Tyr Ala Ser Tyr Leu Glu Ser Gly Val Pro Ser Arg Phe Ser Gly Ser
            325                 330                 335

Gly Ser Gly Thr Asp Phe Thr Leu Thr Ile Ser Ser Leu Gln Pro Glu
        340                 345                 350

Asp Ala Ala Thr Tyr Tyr Cys Gln His Ser Arg Glu Phe Pro Trp Thr
    355                 360                 365

Phe Gly Gly Gly Thr Lys Val Glu Ile Lys Arg Ala Asp Ala Ala Pro
370                 375                 380

Gly Gly Gly Gly Ser Gly Gly Gly Gly Ser Gly Gly Gly Gly Ser Glu
385                 390                 395                 400

Val Gln Leu Val Glu Ser Gly Gly Gly Asp Val Lys Pro Gly Gly Ser
            405                 410                 415
```

```
Leu Arg Leu Ser Cys Ala Ala Ser Gly Phe Thr Phe Ser Asn Tyr Gly
        420                 425                 430

Met His Trp Val Arg Gln Ala Pro Glu Lys Gly Leu Glu Trp Val Ser
            435                 440                 445

Tyr Ile Ser Ser Gly Ser Ser Thr Ile Tyr Tyr Ala Asp Ser Val Lys
450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
                500                 505                 510

Val Ser Ser
        515

<210> SEQ ID NO 44
<211> LENGTH: 515
<212> TYPE: PRT
<213> ORGANISM: Artificial Sequence
<220> FEATURE:
<223> OTHER INFORMATION: Variant 16

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Thr Val Ser Thr Ser
            20                  25                  30

Ser Tyr Ser Tyr Met His Trp Tyr Gln Gln Lys Pro Gly Lys Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
                165                 170                 175

Leu Glu Trp Val Ser Tyr Ile Ser Ser Gly Ser Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255
```

Phe Pro Leu Ala Pro Leu Glu Ser Ser Gly Ser Asp Ile Gln Met Thr
                260                 265                 270

Gln Ser Pro Ser Ser Leu Ser Ala Ser Val Gly Asp Arg Val Thr Ile
            275                 280                 285

Thr Cys Arg Ala Ser Lys Thr Val Ser Thr Ser Ser Tyr Ser Tyr Met
290                 295                 300

His Trp Tyr Gln Gln Lys Pro Gly Lys Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
        355                 360                 365

Phe Gly Gln Gly Thr Lys Val Glu Ile Lys Arg Ala Asp Ala Ala Pro
370                 375                 380

Gly Gly Gly Gly Ser Gly Gly Gly Ser Gly Gly Gly Gly Ser Glu
385                 390                 395                 400

Val Gln Leu Val Glu Ser Gly Gly Leu Val Gln Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Gly Lys Gly Leu Glu Trp Val Ser
        435                 440                 445

Tyr Ile Ser Ser Gly Ser Ser Thr Ile Tyr Tyr Ala Asp Ser Val Lys
450                 455                 460

Gly Arg Phe Thr Ile Ser Arg Asp Asn Ala Lys Asn Ser Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
            500                 505                 510

Val Ser Ser
        515

<210> SEQ ID NO 45
<211> LENGTH: 515
<212> TYPE: PRT
<213> ORGANISM: Artificial Sequence
<220> FEATURE:
<223> OTHER INFORMATION: Variant 17

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Thr Val Ser Thr Ser
            20                  25                  30

Ser Tyr Ser Tyr Met His Trp Tyr Gln Gln Lys Pro Gly Lys Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

```
Glu Phe Pro Trp Thr Phe Gly Gln Gly Thr Lys Val Glu Ile Lys Arg
                100                 105                 110

Ala Asp Ala Ala Pro Gly Gly Gly Ser Gly Gly Gly Ser Gly
        115                 120                 125

Gly Gly Gly Ser Glu Val Gln Leu Val Glu Ser Gly Gly Val Val
130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Gly Ser Ser Thr Ile Tyr Tyr
                180                 185                 190

Ala Asp Ser Val Lys Gly Arg Phe Thr Ile Ser Arg Asp Asn Ser Lys
                195                 200                 205

Asn Thr Leu Tyr Leu Gln Met Asn Ser Leu Arg Ala Glu Asp Thr Ala
                210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
                260                 265                 270

Gln Ser Pro Ser Ser Leu Ser Ala Ser Val Gly Asp Arg Val Thr Ile
                275                 280                 285

Thr Cys Arg Ala Ser Lys Thr Val Ser Thr Ser Ser Tyr Ser Tyr Met
                290                 295                 300

His Trp Tyr Gln Gln Lys Pro Gly Lys Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
                340                 345                 350

Asp Phe Ala Thr Tyr Tyr Cys Gln His Ser Arg Glu Phe Pro Trp Thr
                355                 360                 365

Phe Gly Gln Gly Thr Lys Val Glu Ile Lys Arg Ala Asp Ala Ala Pro
                370                 375                 380

Gly Gly Gly Gly Ser Gly Gly Gly Ser Gly Gly Gly Ser Glu
385                 390                 395                 400

Val Gln Leu Val Glu Ser Gly Gly Val Val Gln Pro Gly Gly Ser
                405                 410                 415

Leu Arg Leu Ser Cys Ala Ala Ser Gly Phe Thr Phe Ser Asn Tyr Gly
                420                 425                 430

Met His Trp Val Arg Gln Ala Pro Glu Lys Gly Leu Glu Trp Val Ser
                435                 440                 445

Tyr Ile Ser Ser Gly Ser Ser Thr Ile Tyr Tyr Ala Asp Ser Val Lys
                450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
                500                 505                 510
```

Val Ser Ser
        515

<210> SEQ ID NO 46
<211> LENGTH: 515
<212> TYPE: PRT
<213> ORGANISM: Artificial Sequence
<220> FEATURE:
<223> OTHER INFORMATION: Variant 18

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Thr Val Ser Thr Ser
            20                  25                  30

Ser Tyr Ser Tyr Met His Trp Tyr Gln Gln Lys Pro Gly Lys Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Gly Ser Gly
        115                 120                 125

Gly Gly Gly Ser Glu Val Gln Leu Val Glu Ser Gly Gly Gly Asp Val
    130                 135                 140

Lys Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Glu Lys Gly
                165                 170                 175

Leu Glu Trp Val Ser Tyr Ile Ser Ser Gly Ser Ser Thr Ile Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Arg Gly Leu Leu Leu Asp Tyr Trp Gly Gln
225                 230                 235                 240

Gly Thr Thr Val Thr Val Ser Ser Ala Ser Thr Lys Gly Pro Ser Val
                245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Val Gly Asp Arg Val Thr Ile
        275                 280                 285

Thr Cys Arg Ala Ser Lys Thr Val Ser Thr Ser Ser Tyr Ser Tyr Met
    290                 295                 300

His Trp Tyr Gln Gln Lys Pro Gly Lys Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

```
Asp Phe Ala Thr Tyr Tyr Cys Gln His Ser Arg Glu Phe Pro Trp Thr
            355                 360                 365

Phe Gly Gln Gly Thr Lys Val Glu Ile Lys Arg Ala Asp Ala Ala Pro
    370                 375                 380

Gly Gly Gly Gly Ser Gly Gly Gly Ser Gly Gly Gly Gly Ser Glu
385                 390                 395                 400

Val Gln Leu Val Glu Ser Gly Gly Asp Val Lys Pro Gly Gly Ser
                405                 410                 415

Leu Arg Leu Ser Cys Ala Ala Ser Phe Thr Phe Ser Asn Tyr Gly
                420                 425                 430

Met His Trp Val Arg Gln Ala Pro Glu Lys Gly Leu Glu Trp Val Ser
            435                 440                 445

Tyr Ile Ser Ser Gly Ser Ser Thr Ile Tyr Tyr Ala Asp Ser Val Lys
            450                 455                 460

Gly Arg Phe Thr Ile Ser Arg Asp Asn Ser Lys Asn Thr Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Leu Asp Tyr Trp Gly Gln Gly Thr Thr Val Thr
                500                 505                 510

Val Ser Ser
        515

<210> SEQ ID NO 47
<211> LENGTH: 515
<212> TYPE: PRT
<213> ORGANISM: Artificial Sequence
<220> FEATURE:
<223> OTHER INFORMATION: Variant 19

<400> SEQUENCE: 47

Asp Ile Gln Met Thr Gln Ser Pro Ser Ser Leu Ser Ala Ser Leu Gly
1               5                   10                  15

Asp Arg Ala Thr Ile Thr Cys Arg Ala Ser Lys Thr Val Ser Thr Ser
            20                  25                  30

Ser Tyr Ser Tyr Met His Trp Tyr Gln Gln Lys Pro Gly Gln Ala Pro
        35                  40                  45

Lys Leu Leu Ile Lys Tyr Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Val Glu Ile Lys Arg
            100                 105                 110

Ala Asp Ala Ala Pro Gly Gly Gly Gly Ser Gly Gly Gly Ser Gly
            115                 120                 125

Gly Gly Gly Ser Glu Val Gln Leu Val Glu Ser Gly Gly Gly Leu Val
        130                 135                 140

Gln Pro Gly Gly Ser Leu Arg Leu Ser Cys Ala Ala Ser Gly Phe Thr
145                 150                 155                 160

Phe Ser Asn Tyr Gly Met His Trp Val Arg Gln Ala Pro Gly Lys Gly
                165                 170                 175

Leu Glu Trp Val Ser Tyr Ile Ser Ser Gly Ser Ser Thr Ile Tyr Tyr
            180                 185                 190
```

Ala Asp Ser Val Lys Gly Arg Phe Thr Ile Ser Arg Asp Asn Ala Lys
            195                 200                 205

Asn Ser Leu Tyr Leu Gln Met Asn Ser Leu Arg Ala Glu Asp Thr Ala
        210                 215                 220

Val Tyr Tyr Cys Ala Arg Arg Gly Leu Leu Asp Tyr Trp Gly Gln
225                 230                 235                 240

Gly Thr Thr Val Thr Val Ser Ala Ser Thr Lys Gly Pro Ser Val
            245                 250                 255

Phe Pro Leu Ala Pro Leu Glu Ser Ser Gly Ser Asp Ile Gln Met Thr
            260                 265                 270

Gln Ser Pro Ser Ser Leu Ser Ala Ser Leu Gly Asp Arg Ala Thr Ile
        275                 280                 285

Thr Cys Arg Ala Ser Lys Thr Val Ser Thr Ser Ser Tyr Ser Tyr Met
        290                 295                 300

His Trp Tyr Gln Gln Lys Pro Gly Gln Ala Pro Lys Leu Leu Ile Lys
305                 310                 315                 320

Tyr Ala Ser Tyr Leu Glu Ser Gly Val Pro Ser Arg Phe Ser Gly Ser
                325                 330                 335

Gly Ser Gly Thr Asp Phe Thr Leu Thr Ile Ser Ser Leu Gln Pro Glu
            340                 345                 350

Asp Phe Ala Thr Tyr Tyr Cys Gln His Ser Arg Glu Phe Pro Trp Thr
            355                 360                 365

Phe Gly Gln Gly Thr Lys Val Glu Ile Lys Arg Ala Asp Ala Ala Pro
            370                 375                 380

Gly Gly Gly Gly Ser Gly Gly Gly Ser Gly Gly Gly Gly Ser Glu
385                 390                 395                 400

Val Gln Leu Val Glu Ser Gly Gly Gly Leu Val Gln Pro Gly Gly Ser
                405                 410                 415

Leu Arg Leu Ser Cys Ala Ala Ser Gly Phe Thr Phe Ser Asn Tyr Gly
            420                 425                 430

Met His Trp Val Arg Gln Ala Pro Gly Lys Gly Leu Glu Trp Val Ser
            435                 440                 445

Tyr Ile Ser Ser Gly Ser Ser Thr Ile Tyr Tyr Ala Asp Ser Val Lys
450                 455                 460

Gly Arg Phe Thr Ile Ser Arg Asp Asn Ala Lys Asn Ser Leu Tyr Leu
465                 470                 475                 480

Gln Met Asn Ser Leu Arg Ala Glu Asp Thr Ala Val Tyr Tyr Cys Ala
                485                 490                 495

Arg Arg Gly Leu Leu Asp Tyr Trp Gly Gln Gly Thr Thr Val Thr
            500                 505                 510

Val Ser Ser
        515

<210> SEQ ID NO 48
<211> LENGTH: 116
<212> TYPE: PRT
<213> ORGANISM: Artificial Sequence
<220> FEATURE:
<223> OTHER INFORMATION: Heavy Chain variable region murine 3E10 (D31N)

<400> SEQUENCE: 48

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asn Tyr
            20                  25                  30

```
Gly Met His Trp Val Arg Gln Ala Pro Glu Lys Gly Leu Glu Trp Val
         35                  40                  45

Ala Tyr Ile Ser Ser Gly Ser Ser Thr Ile Tyr Tyr Ala Asp Thr Val
 50                  55                  60

Lys Gly Arg Phe Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Arg Gly Leu Leu Leu Asp Tyr Trp Gly Gln Gly Thr Thr Leu
                 100                 105                 110

Thr Val Ser Ser
        115

<210> SEQ ID NO 49
<211> LENGTH: 111
<212> TYPE: PRT
<213> ORGANISM: Artificial Sequence
<220> FEATURE:
<223> OTHER INFORMATION: Light Chain variable region murine 3E10 (D31N)

<400> SEQUENCE: 49

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
         35                  40                  45

Lys Leu Leu Ile Lys Tyr Ala Ser Tyr Leu Glu Ser Gly Val Pro Ala
 50                  55                  60

Arg Phe Ser Gly Ser Gly Ser Gly Thr Asp Phe His Leu Asn Ile His
 65                  70                  75                  80

Pro Val Glu Glu Glu Asp Ala Ala Thr Tyr Tyr Cys Gln His Ser Arg
                 85                  90                  95

Glu Phe Pro Trp Thr Phe Gly Gly Gly Thr Lys Leu Glu Leu Lys
                 100                 105                 110

<210> SEQ ID NO 50
<211> LENGTH: 541
<212> TYPE: PRT
<213> ORGANISM: Artificial Sequence
<220> FEATURE:
<223> OTHER INFORMATION: 3E10 (D31N) murine prototype produced from P.
      pastoris

<400> SEQUENCE: 50

Ala Gly Ile His Asp Ile Val Leu Thr Gln Ser Pro Ala Ser Leu Ala
1               5                   10                  15

Val Ser Leu Gly Gln Arg Ala Thr Ile Ser Cys Arg Ala Ser Lys Ser
            20                  25                  30

Val Ser Thr Ser Ser Tyr Ser Tyr Met His Trp Tyr Gln Gln Lys Pro
         35                  40                  45

Gly Gln Pro Pro Lys Leu Leu Ile Lys Tyr Ala Ser Tyr Leu Glu Ser
 50                  55                  60

Gly Val Pro Ala Arg Phe Ser Gly Ser Gly Ser Gly Thr Asp Phe Thr
 65                  70                  75                  80

Leu Asn Ile His Pro Val Glu Glu Glu Asp Ala Ala Thr Tyr Tyr Cys
                 85                  90                  95

Gln His Ser Arg Glu Phe Pro Trp Thr Phe Gly Gly Gly Thr Lys Leu
```

```
                100                 105                 110
Glu Ile Lys Arg Ala Asp Ala Ala Pro Gly Gly Gly Ser Gly Gly
            115                 120                 125
Gly Gly Ser Gly Gly Gly Ser Glu Val Gln Leu Val Glu Ser Gly
            130                 135                 140
Gly Gly Leu Val Lys Pro Gly Gly Ser Arg Lys Leu Ser Cys Ala Ala
145                 150                 155                 160
Ser Gly Phe Thr Phe Ser Asn Tyr Gly Met His Trp Val Arg Gln Ala
            165                 170                 175
Pro Glu Lys Gly Leu Glu Trp Val Ala Tyr Ile Ser Ser Gly Ser Ser
            180                 185                 190
Thr Ile Tyr Tyr Ala Asp Thr Val Lys Gly Arg Phe Thr Ile Ser Arg
            195                 200                 205
Asp Asn Ala Lys Asn Thr Leu Phe Leu Gln Met Thr Ser Leu Arg Ser
            210                 215                 220
Glu Asp Thr Ala Met Tyr Tyr Cys Ala Arg Arg Gly Leu Leu Leu Asp
225                 230                 235                 240
Tyr Trp Gly Gln Gly Thr Thr Leu Thr Val Ser Ser Ala Ser Thr Lys
            245                 250                 255
Gly Pro Ser Val Phe Pro Leu Ala Pro Leu Glu Ser Ser Gly Ser Asp
            260                 265                 270
Ile Val Leu Thr Gln Ser Pro Ala Ser Leu Ala Val Ser Leu Gly Gln
            275                 280                 285
Arg Ala Thr Ile Ser Cys Arg Ala Ser Lys Ser Val Ser Thr Ser Ser
            290                 295                 300
Tyr Ser Tyr Met His Trp Tyr Gln Gln Lys Pro Gly Gln Pro Pro Lys
305                 310                 315                 320
Leu Leu Ile Lys Tyr Ala Ser Tyr Leu Glu Ser Gly Val Pro Ala Arg
            325                 330                 335
Phe Ser Gly Ser Gly Ser Gly Thr Asp Phe Thr Leu Asn Ile His Pro
            340                 345                 350
Val Glu Glu Glu Asp Ala Ala Thr Tyr Tyr Cys Gln His Ser Arg Glu
            355                 360                 365
Phe Pro Trp Thr Phe Gly Gly Gly Thr Lys Leu Glu Ile Lys Arg Ala
            370                 375                 380
Asp Ala Ala Pro Gly Gly Gly Ser Gly Gly Gly Gly Ser Gly Gly
385                 390                 395                 400
Gly Gly Ser Glu Val Gln Leu Val Glu Ser Gly Gly Gly Leu Val Lys
            405                 410                 415
Pro Gly Gly Ser Arg Lys Leu Ser Cys Ala Ala Ser Gly Phe Thr Phe
            420                 425                 430
Ser Asn Tyr Gly Met His Trp Val Arg Gln Ala Pro Glu Lys Gly Leu
            435                 440                 445
Glu Trp Val Ala Tyr Ile Ser Ser Gly Ser Ser Thr Ile Tyr Tyr Ala
            450                 455                 460
Asp Thr Val Lys Gly Arg Phe Thr Ile Ser Arg Asp Asn Ala Lys Asn
465                 470                 475                 480
Thr Leu Phe Leu Gln Met Thr Ser Leu Arg Ser Glu Asp Thr Ala Met
            485                 490                 495
Tyr Tyr Cys Ala Arg Arg Gly Leu Leu Leu Asp Tyr Trp Gly Gln Gly
            500                 505                 510
Thr Thr Leu Thr Val Ser Ser Leu Glu Gln Lys Leu Ile Ser Glu Glu
            515                 520                 525
```

Asp Leu Asn Ser Ala Val Asp His His His His His
      530                 535                 540

<210> SEQ ID NO 51
<211> LENGTH: 1555
<212> TYPE: DNA
<213> ORGANISM: Artificial Sequence
<220> FEATURE:
<223> OTHER INFORMATION: Variant 2

<400> SEQUENCE: 51

| | | | | | |
|---|---|---|---|---|---|
| gacatccaga | tgacccagtc | tccatcctct | ctgtctgctt | ccctgggcga | cagagccacc | 60 |
| atcacctgta | gagcctccaa | gtccgtgtcc | acctcctcct | actcctacat | gcactggtat | 120 |
| cagcagaagc | ccggccagcc | tcctaagctg | ctgattaagt | acgcctccta | cctggaatcc | 180 |
| ggcgtgccct | ctagattctc | cggctctggc | tctggcaccg | actttaccct | gacaatctcc | 240 |
| agcctgcagc | ctgaggatgc | cgctacctac | tactgccagc | actccagaga | gttcccttgg | 300 |
| acctttggcg | gaggcaccaa | ggtggaaatc | aagagagctg | acgctgctcc | tggcggcgga | 360 |
| ggaagcggag | cggaggttc | tggtggtggt | ggatctgaag | tgcagctggt | ggaatctggc | 420 |
| ggaggattgg | ttcagcctgg | cggctctctg | agactgtctt | gtgccgcttc | tggcttcacc | 480 |
| ttctccaact | acggcatgca | ttgggtccga | caggcccctg | gcaaaggact | ggaatgggtg | 540 |
| tcctacatct | cctccagctc | ctccaccatc | tactacgccg | actccgtgaa | gggcagattc | 600 |
| accatctcca | gagacaacgc | caagaactcc | ctgtacctgc | agatgaacag | cctgagagcc | 660 |
| gaggacaccg | ccgtgtacta | ctgtgctaga | agaggcctgc | tgctggacta | ttggggccag | 720 |
| ggcacaacag | tgaccgtgtc | ctctgcttcc | accaagggac | cctctgtgtt | ccctctggct | 780 |
| cctctggaat | cttccggctc | cgatattcag | atgacacaga | gccctcccag | cctgtccgcc | 840 |
| tctctgggag | atagagctac | aatcacatgc | cgggccagca | gtctgtgtc | taccagcagc | 900 |
| tacagctata | tgcattggta | tcaacaaaaa | cctgggcagc | caccaaaact | gctgatcaaa | 960 |
| tacgctagct | acctcgagag | cggcgtgcca | agcagatttt | ctggctccgg | cagcggcaca | 1020 |
| gactttacac | tcaccattag | ctccctgcaa | ccagaggacg | ctgccaccta | ttattgtcag | 1080 |
| cactcccgcg | aatttccatg | gaccttcgga | ggcggcacaa | agtcgagat | caagcgggct | 1140 |
| gatgctgcac | caggtggcgg | cggtagtggt | ggcggaggaa | gtggcggagg | cggatctgaa | 1200 |
| gtccaattgg | ttgaaagcgg | cggtggcctt | gtgcaacccg | gtggaagtct | gagactctcc | 1260 |
| tgcgctgcct | ccggctttac | cttcagcaat | tacggaatgc | actgggttcg | ccaagctcca | 1320 |
| ggcaaaggct | tggagtgggt | ttcctatatc | agctcctcta | gcagcaccat | ctattatgct | 1380 |
| gacagcgtga | aaggccggtt | taccatcagc | cgggataatg | ccaagaatag | cctgtatctc | 1440 |
| caaatgaact | ctctccgcgc | tgaggataca | gctgtgtact | attgcgcccg | cagaggactc | 1500 |
| ctgctcgatt | actggggaca | gggaactacc | gtgacagtgt | ctagctgatg | aattc | 1555 |

<210> SEQ ID NO 52
<211> LENGTH: 1555
<212> TYPE: DNA
<213> ORGANISM: Artificial Sequence
<220> FEATURE:
<223> OTHER INFORMATION: Variant 3

<400> SEQUENCE: 52

| | | | | | |
|---|---|---|---|---|---|
| gacatccaga | tgacccagtc | tccatcctct | ctgtctgctt | ccctgggcga | cagagccacc | 60 |
| atcacctgta | gagcctccaa | gtccgtgtcc | acctcctcct | actcctacat | gcactggtat | 120 |

| | |
|---|---:|
| cagcagaagc ccggccagcc tcctaagctg ctgattaagt acgcctccta cctggaatcc | 180 |
| ggcgtgccct ctagattctc cggctctggc tctggcaccg actttaccct gacaatctcc | 240 |
| agcctgcagc ctgaggatgc cgctacctac tactgccagc actccagaga gttcccttgg | 300 |
| acctttggcg gaggcaccaa ggtggaaatc aagagagctg acgctgctcc tggcggcgga | 360 |
| ggaagcggag gcggaggttc tggtggtggt ggatctgaag tgcagctggt ggaatcaggt | 420 |
| ggcggagttg ttcagcctgg cggctctctg agactgtctt gtgccgcttc tggcttcacc | 480 |
| ttctccaact acggcatgca ttgggtccga caggcccctg agaaaggcct ggaatgggtg | 540 |
| tcctacatct cctccagctc ctccaccatc tactacgccg actccgtgaa gggcagattc | 600 |
| accatctctc gggacaactc caagaacacc ctgtacctgc agatgaactc cctgagagcc | 660 |
| gaggacaccg ccgtgtacta ctgtgctaga gaggcctgc tgctggacta ttggggccag | 720 |
| ggcacaacag tgaccgtgtc ctctgcttcc accaagggac cctctgtgtt ccctctggct | 780 |
| cctctggaat cttccggctc cgatattcag atgacacaga gcccttccag cctgtccgcc | 840 |
| tctctgggag atagagctac aatcacatgc cgggccagca gtctgtgtc taccagcagc | 900 |
| tacagctata tgcattggta tcaacaaaaa cctgggcagc caccaaaact gctgatcaaa | 960 |
| tacgctagct acctcgagag cggcgtgcca agcagatttt ctggctccgg cagcggcaca | 1020 |
| gactttacac tcaccattag ctccctgcaa ccagaggacg ctgccaccta ttattgtcag | 1080 |
| cactcccgcg aatttccatg gaccttcgga ggcggcacaa agtcgagat caagcgggct | 1140 |
| gatgctgcac caggtggcgg cggatctggt ggcggaggct ctggcggagg cggtagtgaa | 1200 |
| gttcagttgg tcgagtcagg cggtggcgtt gtgcaacctg gtggtagtct gaggctgtcc | 1260 |
| tgcgctgcct ccggctttac cttcagcaat tacggaatgc actgggttcg ccaagctcca | 1320 |
| gagaagggac ttgagtgggt ttcctatatc agctccagca gctctaccat ctattatgct | 1380 |
| gacagcgtga aaggccggtt taccatcagc cgggataaca gcaagaatac tctgtatctc | 1440 |
| caaatgaata gcctgcgcgc cgaggataca gctgtgtatt attgcgccag acggggactc | 1500 |
| ctgctggatt actggggaca aggtactacc gtgacagtgt ccagctgatg aattc | 1555 |

<210> SEQ ID NO 53
<211> LENGTH: 1555
<212> TYPE: DNA
<213> ORGANISM: Artificial Sequence
<220> FEATURE:
<223> OTHER INFORMATION: Variant 4

<400> SEQUENCE: 53

| | |
|---|---:|
| gacatccaga tgacccagtc tccatcctct ctgtctgctt ccctgggcga cagagccacc | 60 |
| atcacctgta gagcctccaa gtccgtgtcc acctcctcct actcctacat gcactggtat | 120 |
| cagcagaagc ccggccagcc tcctaagctg ctgattaagt acgcctccta cctggaatcc | 180 |
| ggcgtgccct ctagattctc cggctctggc tctggcaccg actttaccct gacaatctcc | 240 |
| agcctgcagc ctgaggatgc cgctacctac tactgccagc actccagaga gttcccttgg | 300 |
| acctttggcg gaggcaccaa ggtggaaatc aagagagctg acgctgctcc tggcggcgga | 360 |
| ggaagcggag gcggaggttc tggtggtggt ggatctgaag tgcagctggt ggaatctggc | 420 |
| ggtggcgacg tgaaacctgg cggatctctg agactgtctt gtgccgcctc tggcttcacc | 480 |
| ttctccaact acggcatgca ttgggtccga caggcccctg agaaaggcct ggaatgggtg | 540 |
| tcctacatct cctccagctc ctccaccatc tactacgccg actccgtgaa gggcagattc | 600 |

| | |
|---|---:|
| accatctctc gggacaactc caagaacacc ctgtacctgc agatgaactc cctgagagcc | 660 |
| gaggacaccg ccgtgtacta ctgtgctaga agaggcctgc tgctggacta ttggggccag | 720 |
| ggcacaacag tgaccgtgtc ctctgcttcc accaagggac cctctgtgtt ccctctggct | 780 |
| cctctggaat cttccggctc cgatattcag atgacacaga gcccttccag cctgtccgcc | 840 |
| tctctgggag atagagctac aatcacatgc cgggccagca agtctgtgtc taccagcagc | 900 |
| tacagctata tgcattggta tcaacaaaaa cctgggcagc caccaaaact gctgatcaaa | 960 |
| tacgctagct acctcgagag cggcgtgcca agcagatttt ctggctccgg cagcggcaca | 1020 |
| gactttacac tcaccattag ctccctgcaa ccagaggacg ctgccaccta ttattgtcag | 1080 |
| cactcccgcg aatttccatg gaccttcggt ggcggaacaa aggtcgagat caagcgggct | 1140 |
| gatgcagcac ctggcggagg cggttcaggt ggcggaggat caggcggtgg cggtagtgaa | 1200 |
| gttcagttgg ttgagtccgg cggagggat gttaagcctg gcggtagcct gagactctcc | 1260 |
| tgcgctgctt ccggctttac cttcagcaat tacggaatgc actgggttcg ccaagctcca | 1320 |
| gagaagggac ttgagtgggt ttcctatatc agctccagca gctctaccat ctattatgct | 1380 |
| gacagcgtga aaggccggtt taccatcagc cgggataaca gcaagaatac tctgtatctc | 1440 |
| caaatgaaca gcctgcgcgc cgaggataca gctgtgtatt attgcgccag acggggactc | 1500 |
| ctgctggatt actggggaca aggtactacc gtgacagtgt ccagctgatg aattc | 1555 |

<210> SEQ ID NO 54
<211> LENGTH: 1555
<212> TYPE: DNA
<213> ORGANISM: Artificial Sequence
<220> FEATURE:
<223> OTHER INFORMATION: Variant 6

<400> SEQUENCE: 54

| | |
|---|---:|
| gacatccaga tgacccagtc tccatcctct ctgtctgctt ccctgggcga cagagccacc | 60 |
| atcacctgta gagcctccaa gtccgtgtcc acctcctcct actcctacat gcactggtat | 120 |
| cagcagaagc ccggccaggc tcctaagctg ctgattaagt acgcctccta cctggaatcc | 180 |
| ggcgtgccct ctagattctc cggctctggc tctggcaccg actttaccct gacaatctcc | 240 |
| agcctgcagc ctgaggactt cgccacctac tactgccagc actccagaga gttcccttgg | 300 |
| acctttggcc agggcaccaa ggtggaaatc aagagagctg acgctgctcc tggcggcgga | 360 |
| ggatctggcg gaggtggaag cggaggcggt ggatctgaag tgcagctggt tgagagtggt | 420 |
| ggcggattgg ttcagcctgg cggatctctg agactgtctt gtgccgcctc tggcttcacc | 480 |
| ttctccaact acggcatgca ttgggtccga caggcccctg gcaaaggact ggaatgggtg | 540 |
| tcctacatct cctccagctc ctccaccatc tactacgccg actccgtgaa gggcagattc | 600 |
| accatctcca gagacaacgc caagaactcc ctgtacctgc agatgaacag cctgagagcc | 660 |
| gaggacaccg ccgtgtacta ctgtgctaga agaggcctgc tgctggacta ttggggccag | 720 |
| ggaacaaccg tgaccgtgtc ctctgcttcc acaaagggcc cctctgtgtt ccctctggct | 780 |
| cctctggaat cttccggctc cgatattcag atgacacaga gcccttccag cctgtccgcc | 840 |
| tctctgggag atagagctac aatcacatgc cgggccagca agtctgtgtc taccagcagc | 900 |
| tacagctata tgcattggta tcaacaaaaa cccgggcaag ccccaaagct cctgatcaaa | 960 |
| tacgccagct atctggaaag cggcgtgcca tctcggtttt ctggctccgg aagcggcaca | 1020 |
| gactttacac tcaccattag ctccctgcag ccagaagatt ttgctaccta ttattgccag | 1080 |
| catagccgcg agtttccatg gacattcgga cagggaacta aggtcgagat caagcgggcc | 1140 |

| | |
|---|---|
| gatgctgcac ctggcggagg cggttcaggt ggcggaggca gcggtggcgg cggtagtgaa | 1200 |
| gttcagttgg tcgagtcagg cggcggactt gttcaaccag gtggtagcct gagactgagc | 1260 |
| tgtgctgcta gcggctttac cttcagcaat tacggaatgc actgggttcg ccaagctcca | 1320 |
| ggcaaaggct tggagtgggt ttcctatatc agctcctcta gctctaccat ctattatgcc | 1380 |
| gatagcgtga aaggccggtt taccatcagc cgggataatg ccaagaatag cctgtatctc | 1440 |
| caaatgaact ctctccgcgc tgaggatacc gctgtgtatt attgcgcccg cagaggactc | 1500 |
| ctgctcgatt actggggaca gggcactaca gtgacagtgt ctagctgatg aattc | 1555 |

<210> SEQ ID NO 55
<211> LENGTH: 1555
<212> TYPE: DNA
<213> ORGANISM: Artificial Sequence
<220> FEATURE:
<223> OTHER INFORMATION: Variant 7

<400> SEQUENCE: 55

| | |
|---|---|
| gacatccaga tgacccagtc tccatcctct ctgtctgctt ccctgggcga cagagccacc | 60 |
| atcacctgta gagcctccaa gtccgtgtcc acctcctcct actcctacat gcactggtat | 120 |
| cagcagaagc ccggccaggc tcctaagctg ctgattaagt acgcctccta cctggaatcc | 180 |
| ggcgtgccct ctagattctc cggctctggc tctggcaccg actttaccct gacaatctcc | 240 |
| agcctgcagc ctgaggactt cgccacctac tactgccagc actccagaga gttcccttgg | 300 |
| acctttggcc agggcaccaa ggtggaaatc aagagagctg acgctgctcc tggcggcgga | 360 |
| ggatctggcg gaggtggaag cggaggcggt ggatctgaag tgcagctggt tgagagtggt | 420 |
| ggcggagttg ttcagcctgg cggatctctg agactgtctt gtgccgcctc tggcttcacc | 480 |
| ttctccaact acggcatgca ttgggtccga caggcccctg agaaaggcct ggaatgggtg | 540 |
| tcctacatct cctccagctc ctccaccatc tactacgccg actccgtgaa gggcagattc | 600 |
| accatctctc gggacaactc caagaacacc ctgtacctgc agatgaactc cctgagagcc | 660 |
| gaggacaccg ccgtgtacta ctgtgctaga gaggcctgc tgctgactat tggggccag | 720 |
| ggaacaaccg tgaccgtgtc ctctgcttcc acaaagggcc cctctgtgtt ccctctggct | 780 |
| cctctggaat cttccggctc cgatattcag atgacacaga gcccttccag cctgtccgcc | 840 |
| tctctgggag atagagctac aatcacatgc cgggccagca gtctgtgtc taccagcagc | 900 |
| tacagctata tgcattggta tcaacaaaaa cccgggcaag ccccaaagct cctgatcaaa | 960 |
| tacgccagct atctggaaag cggcgtgcca tctcggtttt ctggctccgg aagcggcaca | 1020 |
| gactttacac tcaccattag ctccctgcag ccagaagatt ttgctaccta ttattgccag | 1080 |
| catagccgcg agtttccatg gacattcgga caggaactaa ggtcgagat caagcgggcc | 1140 |
| gatgctgcac ctggcggagg cggttcaggt ggtggtggat caggtggcgg aggcagtgaa | 1200 |
| gtccagttgg tggaatcagg cggtggcgtt gtgcaacctg gtggaagtct gaggctgtcc | 1260 |
| tgcgctgctt ccggctttac cttcagcaat tacggaatgc actgggttcg ccaagctcca | 1320 |
| gagaagggac ttgagtgggt ttcctatatc agctccagca gctctaccat ctattatgct | 1380 |
| gacagcgtga aaggccggtt taccatcagc cgggataaca gcaagaatac tctgtatctc | 1440 |
| caaatgaata gcctgcgcgc cgaggataca gctgtgtatt attgcgccag acggggactc | 1500 |
| ctgctggatt actggggaca aggcactaca gtgacagtgt ccagctgatg aattc | 1555 |

<210> SEQ ID NO 56

<211> LENGTH: 1555
<212> TYPE: DNA
<213> ORGANISM: Artificial Sequence
<220> FEATURE:
<223> OTHER INFORMATION: Variant 8

<400> SEQUENCE: 56

| | |
|---|---|
| gacatccaga tgacccagtc tccatcctct ctgtctgctt ccctgggcga cagagccacc | 60 |
| atcacctgta gagcctccaa gtccgtgtcc acctcctcct actcctacat gcactggtat | 120 |
| cagcagaagc ccggccaggc tcctaagctg ctgattaagt acgcctccta cctggaatcc | 180 |
| ggcgtgccct ctagattctc cggctctggc tctggcaccg actttaccct gacaatctcc | 240 |
| agcctgcagc ctgaggactt cgccacctac tactgccagc actccagaga gttcccttgg | 300 |
| acctttggcc agggcaccaa ggtggaaatc aagagagctg acgctgctcc tggcggcgga | 360 |
| ggatctggcg gaggtggaag cggaggcggt ggatctgaag tgcagctggt tgagagtggc | 420 |
| ggaggcgacg tgaaacctgg cggatctctg agactgtctt gtgccgcctc tggcttcacc | 480 |
| ttctccaact acggcatgca ttgggtccga caggcccctg agaaaggcct ggaatgggtg | 540 |
| tcctacatct cctccagctc ctccaccatc tactacgccg actccgtgaa gggcagattc | 600 |
| accatctctc gggacaactc caagaacacc ctgtacctgc agatgaactc cctgagagcc | 660 |
| gaggacaccg ccgtgtacta ctgtgctaga gaggcctgc tgctggacta ttggggccag | 720 |
| ggaacaaccg tgaccgtgtc ctctgcttcc acaaagggcc cctctgtgtt ccctctggct | 780 |
| cctctggaat cttccggctc cgatattcag atgacacaga gcccttccag cctgtccgcc | 840 |
| tctctgggag atagagctac aatcacatgc cgggccagca gtctgtgtc taccagcagc | 900 |
| tacagctata tgcattggta tcaacaaaaa cccgggcaag ccccaaagct cctgatcaaa | 960 |
| tacgccagct atctggaaag cggcgtgcca tctcggtttt ctggctccgg aagcggcaca | 1020 |
| gactttacac tcaccattag ctccctgcag ccagaagatt ttgctaccta ttattgccag | 1080 |
| catagccgcg agtttccatg gacattcgga caggaactaa ggtcgagat caagcgggcc | 1140 |
| gatgctgcac caggcggtgg tggttcaggc ggaggcggta gcggcggagg cggctctgaa | 1200 |
| gttcaattgg tggaatcagg tggcgggat gtcaagcctg gtggaagtct gagactcagc | 1260 |
| tgtgccgcca gcggctttac cttcagcaat tacggaatgc actgggttcg ccaagctcca | 1320 |
| gagaagggac ttgagtgggt ttcctatatc agctccagca gctctaccat ctattatgct | 1380 |
| gacagcgtga aggccggtt taccatcagc cgggataaca gcaagaatac tctgtatctc | 1440 |
| caaatgaaca gcctgcgcgc cgaggataca gctgtgtatt attgcgccag acggggactc | 1500 |
| ctgctggatt actggggaca aggcactaca gtgacagtgt ccagctgatg aattc | 1555 |

<210> SEQ ID NO 57
<211> LENGTH: 1555
<212> TYPE: DNA
<213> ORGANISM: Artificial Sequence
<220> FEATURE:
<223> OTHER INFORMATION: Variant 10

<400> SEQUENCE: 57

| | |
|---|---|
| gacatccaga tgacccagtc tccatcctct ctgtccgcct ctgtgggcga cagagtgacc | 60 |
| atcacctgtc gggcctccaa gtccgtgtcc acctcctcct actcctacat gcactggtat | 120 |
| cagcagaagc ccggcaaggc ccctaagctg ctgattaagt acgcctccta cctggaatcc | 180 |
| ggcgtgccct ctagattctc cggctctggc tctggcaccg actttaccct gacaatctcc | 240 |
| agcctgcagc ctgaggactt cgccacctac tactgccagc actccagaga gttcccttgg | 300 |

```
acctttggcc agggcaccaa ggtggaaatc aagagagctg acgctgctcc tggcggcgga    360
ggatctggcg gaggtggaag cggaggcggt ggatctgaag tgcagctggt tgagagtggt    420
ggcggattgg ttcagcctgg cggatctctg agactgtctt gtgccgcctc tggcttcacc    480
ttctccaact acggcatgca ttgggtccga caggcccctg caaaggact ggaatgggtg     540 tcctacatct cctccagctc ctccaccatc tactacgccg actccgtgaa gggcagattc    600
accatctcca gagacaacgc caagaactcc ctgtacctgc agatgaacag cctgagagcc    660
gaggacaccg ccgtgtacta ctgtgctaga gaggcctgc tgctggacta ttggggccag     720
ggaacaaccg tgaccgtgtc ctctgcttcc acaaagggcc cctctgtgtt ccctctggct    780
cctctggaat cttccggctc cgatattcag atgacacaga gcccttccag cctgtctgct    840
tccgtgggag atcgcgtgac aatcacatgc cgggccagca atctgtgtc caccagcagc    900 tacagctata tgcattggta tcaacaaaaa cccgggaaag ctcccaagct cctgatcaaa    960
tacgccagct atctggaaag cggcgtgcca tctcggtttt ctggctccgg aagcggcaca   1020
gactttacac tcaccattag ctccctgcag ccagaagatt ttgctaccta ttattgccag   1080
catagccgcg agtttccatg gacattcgga caggaacta aggtcgagat caagcgggcc    1140
gatgctgcac ctggcggagg cggttcaggt ggcggtggtt caggcggtgg tggctctgag   1200
gttcagttgg tcgagtcagg cggaggactt gttcaaccag gcggaagcct gagactgagc   1260
tgtgctgcta gcggctttac cttcagcaat tacggaatgc actgggttcg ccaagctcca   1320
ggcaaaggct tggagtgggt ttcctatatc agctcctcta gctctaccat ctattatgcc   1380
gatagcgtga aaggccggtt taccatcagc cgggataatg ccaagaatag cctgtatctc   1440
caaatgaact ctctccgcgc tgaggatacc gctgtgtatt attgcgcccg cagaggactc   1500
ctgctcgatt actggggaca gggcactaca gtgacagtgt ctagctgatg aattc         1555

<210> SEQ ID NO 58
<211> LENGTH: 1555
<212> TYPE: DNA
<213> ORGANISM: Artificial Sequence
<220> FEATURE:
<223> OTHER INFORMATION: Variant 11

<400> SEQUENCE: 58
gacatccaga tgacccagtc tccatcctct ctgtccgcct ctgtgggcga cagagtgacc     60
atcacctgtc gggcctccaa gtccgtgtcc acctcctcct actcctacat gcactggtat    120
cagcagaagc ccggcaaggc ccctaagctg ctgattaagt acgcctccta cctggaatcc    180
ggcgtgccct ctagattctc cggctctggc tctggcaccg actttaccct gacaatctcc    240
agcctgcagc ctgaggactt cgccacctac tactgccagc actccagaga gttcccttgg    300
acctttggcc agggcaccaa ggtggaaatc aagagagctg acgctgctcc tggcggcgga    360
ggatctggcg gaggtggaag cggaggcggt ggatctgaag tgcagctggt tgagagtggt    420
ggcggagttg ttcagcctgg cggatctctg agactgtctt gtgccgcctc tggcttcacc    480
ttctccaact acggcatgca ttgggtccga caggcccctg agaaaggcct ggaatgggtg    540
tcctacatct cctccagctc ctccaccatc tactacgccg actccgtgaa gggcagattc    600
accatctctc gggacaactc caagaacacc ctgtacctgc agatgaactc cctgagagcc    660
gaggacaccg ccgtgtacta ctgtgctaga gaggcctgc tgctggacta ttggggccag     720
ggaacaaccg tgaccgtgtc ctctgcttcc acaaagggcc cctctgtgtt ccctctggct    780
```

```
cctctggaat cttccggctc cgatattcag atgacacaga gcccttccag cctgtctgct      840
tccgtgggag atcgcgtgac aatcacatgc cgggccagca atctgtgtc caccagcagc        900 tacagctata tgcattggta tcaacaaaaa cccgggaaag ctcccaagct cctgatcaaa       960
tacgccagct atctggaaag cggcgtgcca tctcggtttt ctggctccgg aagcggcaca      1020
gactttacac tcaccattag ctccctgcag ccagaagatt ttgctaccta ttattgccag      1080
catagccgcg agtttccatg gacattcgga cagggaacta aggtcgagat caagcgggcc     1140
gatgctgcac ctggcggagg cggttcaggt ggtggtggat caggtggcgg aggcagtgaa     1200
gtccagttgg tggaatcagg cggtggcgtt gtgcaacctg gtggaagtct gaggctgtcc    1260
tgcgctgctt ccggctttac cttcagcaat tacggaatgc actgggttcg ccaagctcca   1320
gagaagggac ttgagtgggt ttcctatatc agctccagca gctctaccat ctattatgct    1380
gacagcgtga aaggccggtt taccatcagc cgggataaca gcaagaatac tctgtatctc    1440
caaatgaata gcctgcgcgc cgaggataca gctgtgtatt attgcgccag acggggactc   1500
ctgctggatt actggggaca aggcactaca gtgacagtgt ccagctgatg aattc         1555
```

<210> SEQ ID NO 59
<211> LENGTH: 1555
<212> TYPE: DNA
<213> ORGANISM: Artificial Sequence
<220> FEATURE:
<223> OTHER INFORMATION: Variant 12

<400> SEQUENCE: 59

```
gacatccaga tgacccagtc tccatcctct ctgtccgcct ctgtgggcga cagagtgacc        60
atcacctgtc gggcctccaa gtccgtgtcc acctcctcct actcctacat gcactggtat       120
cagcagaagc ccggcaaggc ccctaagctg ctgattaagt acgcctccta cctggaatcc       180
ggcgtgccct ctagattctc cggctctggc tctggcaccg actttaccct gacaatctcc      240
agcctgcagc ctgaggactt cgccacctac tactgccagc actccagaga gttcccttgg     300
acctttggcc agggcaccaa ggtggaaatc aagagagctg acgctgctcc tggcggcgga    360
ggatctggcg gaggtggaag cggaggcggt ggatctgaag tgcagctggt tgagagtggc   420
ggaggcgacg tgaaacctgg cggatctctg agactgtctt gtgccgcctc tggcttcacc   480
ttctccaact acggcatgca ttgggtccga caggcccctg agaaaggcct ggaatgggtg    540
tcctacatct cctccagctc ctccaccatc tactacgccg actccgtgaa gggcagattc    600
accatctctc gggacaactc caagaacacc ctgtacctgc agatgaactc cctgagagcc   660
gaggacaccg ccgtgtacta ctgtgctaga gaggcctgc tgctggacta ttggggccag   720
ggaacaaccg tgaccgtgtc ctctgcttcc acaaagggcc cctctgtgtt ccctctggct    780
cctctggaat cttccggctc cgatattcag atgacacaga gcccttccag cctgtctgct    840
tccgtgggag atcgcgtgac aatcacatgc cgggccagca atctgtgtc caccagcagc    900 tacagctata tgcattggta tcaacaaaaa cccgggaaag ctcccaagct cctgatcaaa   960
tacgccagct atctggaaag cggcgtgcca tctcggtttt ctggctccgg aagcggcaca  1020
gactttacac tcaccattag ctccctgcag ccagaagatt ttgctaccta ttattgccag  1080
catagccgcg agtttccatg gacattcgga cagggaacta aggtcgagat caagcgggcc 1140
gatgctgcac aggcggtgg tggttcaggc ggaggcggta gcggcggagg cggctctgaa 1200
gttcaattgg tggaatcagg tggcggggat gtcaagcctg gtggaagtct gagactcagc  1260
tgtgccgcca gcggctttac cttcagcaat tacggaatgc actgggttcg ccaagctcca   1320
```

```
gagaagggac ttgagtgggt ttcctatatc agctccagca gctctaccat ctattatgct    1380
gacagcgtga aaggccggtt taccatcagc cgggataaca gcaagaatac tctgtatctc    1440
caaatgaaca gcctgcgcgc cgaggataca gctgtgtatt attgcgccag acggggactc    1500
ctgctggatt actggggaca aggcactaca gtgacagtgt ccagctgatg aattc         1555
```

<210> SEQ ID NO 60
<211> LENGTH: 1555
<212> TYPE: DNA
<213> ORGANISM: Artificial Sequence
<220> FEATURE:
<223> OTHER INFORMATION: Variant 13

<400> SEQUENCE: 60

```
gacatccaga tgacccagtc tccatcctct ctgtctgctt ccctgggcga cagagccacc      60
atcacctgta gagcctccaa gaccgtgtcc acctcctcct actcctacat gcactggtat     120
cagcagaagc ccggccagcc tcctaagctg ctgattaagt acgcctccta cctggaatcc     180
ggcgtgccct ctagattctc cggctctggc tctggcaccg actttaccct gacaatctcc     240
agcctgcagc ctgaggatgc cgctacctac tactgccagc actccagaga gttcccttgg     300
acctttggcg gaggcaccaa ggtggaaatc aagagagctg acgctgctcc tggcggcgga     360
ggaagcggag cgcgaggttc tggtggtggt ggatctgaag tgcagctggt ggaatctggc     420
ggaggattgg ttcagcctgg cggctctctg agactgtctt gtgccgcttc tggcttcacc     480
ttctccaact acggcatgca ttgggtccga caggcccctg gcaaaggact ggaatgggtg     540
tcctacatct cctccggctc ctccaccatc tactacgccg actctgtgaa gggcagattc     600
accatctctc gggacaacgc caagaactcc ctgtacctgc agatgaacag cctgagagcc     660
gaggacaccg ccgtgtacta ctgtgctaga agaggcctgc tgctggacta ttggggccag     720
ggcacaacag tgaccgtgtc tagcgcttcc accaagggac cctctgtgtt ccctctggct     780
cctctggaat cttccggctc cgatattcag atgacacaga gcccttccag cctgtccgcc     840
tctctgggag atagagctac aatcacatgc cgggccagca gacagtgtc taccagcagc     900 tacagctata tgcattggta tcaacaaaaa cctgggcagc caccaaaact gctgatcaaa     960
tacgctagct acctcgagag cggcgtgcca agcagatttt ctggctccgg cagcggcaca    1020
gactttacac tcaccattag ctccctgcaa ccagaggacg ctgccaccta ttattgtcag    1080
cactcccgcg aatttccatg gaccttcgga ggcggcacaa aagtcgagat caagcgggct    1140
gatgctgcac aggtggcgg cggtagtggt ggcggaggaa gtggcggagg cggatctgaa    1200
gtccaattgg ttgaaagcgg cggtggcctt gtgcaacccg gtggaagtct gagactctcc    1260
tgcgctgcct ccggctttac cttcagcaat tacggaatgc actgggttcg ccaagctcca    1320
ggcaaaggct tggagtgggt ttcatatatc tccagcggca gcagcaccat ctattatgct    1380
gacagcgtga aaggccggtt caccatcagc agagataatg ccaagaacag cctctacctc    1440
caaatgaact cactgcgcgc tgaggataca gctgtgtact attgcgcccg cagaggactc    1500
ctgctcgatt actggggaca gggaactacc gtgacagtgt cctcctgatg aattc         1555
```

<210> SEQ ID NO 61
<211> LENGTH: 1555
<212> TYPE: DNA
<213> ORGANISM: Artificial Sequence
<220> FEATURE:
<223> OTHER INFORMATION: Variant 14

<400> SEQUENCE: 61

```
gacatccaga tgacccagtc tccatcctct ctgtctgctt ccctgggcga cagagccacc      60
atcacctgta gagcctccaa gaccgtgtcc acctcctcct actcctacat gcactggtat     120
cagcagaagc ccggccagcc tcctaagctg ctgattaagt acgcctccta cctggaatcc     180
ggcgtgccct ctagattctc cggctctggc tctggcaccg actttaccct gacaatctcc     240
agcctgcagc ctgaggatgc cgctacctac tactgccagc actccagaga gttcccttgg     300
acctttggcg gaggcaccaa ggtggaaatc aagagagctg acgctgctcc tggcggcgga     360
ggaagcggag gcgaggttc tggtggtggt ggatctgaag tgcagctggt ggaatcaggt      420
ggcggagttg ttcagcctgg cggctctctg agactgtctt gtgccgcttc tggcttcacc     480
ttctccaact acggcatgca ttgggtccga caggcccctg agaaaggcct ggaatgggtg     540
tcctacatct cctccggctc ctccaccatc tactacgccg actctgtgaa gggcagattc     600
accatcagcc gggacaactc caagaacacc ctgtacctgc agatgaactc cctgagagcc     660
gaggacaccg ccgtgtacta ctgtgctaga gaggcctgc tgctgactat ttggggccag      720
ggcacaacag tgaccgtgtc tagcgcttcc accaagggac cctctgtgtt ccctctggct     780
cctctggaat cttccggctc cgatattcag atgacacaga gccttccag cctgtccgcc      840
tctctgggag atagagctac aatcacatgc cgggccagca agacagtgtc taccagcagc     900
tacagctata tgcattggta tcaacaaaaa cctgggcagc accaaaact gctgatcaaa      960
tacgctagct acctcgagag cggcgtgcca agcagatttt ctggctccgg cagcggcaca    1020
gactttacac tcaccattag ctccctgcaa ccagaggacg ctgccaccta ttattgtcag    1080
cactcccgcg aatttccatg gaccttcgga ggcggcacaa agtcgagat caagcgggct     1140
gatgctgcac aggtggcgg cggatctggt ggcggaggct ctggcggagg cggtagtgaa     1200
gttcagttgg tcgagtcagg cggtggcgtt gtgcaacctg gtggtagtct gaggctgtcc    1260
tgcgctgcct ccggctttac cttcagcaat tacggaatgc actgggttcg ccaagctcca    1320
gagaagggac ttgagtgggt ttcctatatc agcagcggca gcagcaccat ctattatgct    1380
gacagcgtga aaggccggtt caccatctcc agagacaaca gcaagaatac tctgtatctc    1440
caaatgaata gcctgcgcgc cgaggataca gctgtgtatt attgcgccag acggggactc    1500
ctgctggatt actggggaca aggtactacc gtgacagtgt cctcctgatg aattc         1555
```

<210> SEQ ID NO 62
<211> LENGTH: 1555
<212> TYPE: DNA
<213> ORGANISM: Artificial Sequence
<220> FEATURE:
<223> OTHER INFORMATION: Variant 15

<400> SEQUENCE: 62

```
gacatccaga tgacccagtc tccatcctct ctgtctgctt ccctgggcga cagagccacc      60
atcacctgta gagcctccaa gaccgtgtcc acctcctcct actcctacat gcactggtat     120
cagcagaagc ccggccagcc tcctaagctg ctgattaagt acgcctccta cctggaatcc     180
ggcgtgccct ctagattctc cggctctggc tctggcaccg actttaccct gacaatctcc     240
agcctgcagc ctgaggatgc cgctacctac tactgccagc actccagaga gttcccttgg     300
acctttggcg gaggcaccaa ggtggaaatc aagagagctg acgctgctcc tggcggcgga     360
ggaagcggag gcgaggttc tggtggtggt ggatctgaag tgcagctggt ggaatctggc      420
ggtggcgacg tgaaacctgg cggatctctg agactgtctt gtgccgcctc tggcttcacc     480
```

```
ttctccaact acggcatgca ttgggtccga caggcccctg agaaaggcct ggaatgggtg      540
tcctacatct cctccggctc ctccaccatc tactacgccg actctgtgaa gggcagattc      600
accatcagcc gggacaactc caagaacacc ctgtacctgc agatgaactc cctgagagcc      660
gaggacaccg ccgtgtacta ctgtgctaga gaggcctgc tgctggacta ttggggccag       720
ggcacaacag tgaccgtgtc tagcgcttcc accaagggac cctctgtgtt ccctctggct      780
cctctggaat cttccggctc cgatattcag atgacacaga gcccttccag cctgtccgcc      840
tctctgggag atagagctac aatcacatgc cgggccagca agacagtgtc taccagcagc      900
tacagctata tgcattggta tcaacaaaaa cctgggcagc caccaaaact gctgatcaaa      960
tacgctagct acctcgagag cggcgtgcca agcagatttt ctggctccgg cagcggcaca     1020
gactttacac tcaccattag ctccctgcaa ccagaggacg ctgccaccta ttattgtcag     1080
cactcccgcg aatttccatg gaccttcggt ggcggaacaa aggtcgagat caagcgggct     1140
gatgcagcac ctggcggagg cggttcaggt ggcggaggat caggcggtgg cggtagtgaa     1200
gttcagttgg ttgagtccgg cggagggat gttaagcctg gcggtagcct gagactctcc      1260
tgcgctgctt ccggctttac cttcagcaat tacggaatgc actgggttcg ccaagctcca     1320
gagaagggac ttgagtgggt ttcctatatc agcagcggca gcagcaccat ctattatgct     1380
gacagcgtga aaggccggtt caccatctcc agagacaaca gcaagaatac tctgtatctc     1440
caaatgaaca gcctgcgcgc cgaggataca gctgtgtatt attgcgccag acggggactc     1500
ctgctggatt actggggaca aggtactacc gtgacagtgt cctcctgatg aattc          1555
```

<210> SEQ ID NO 63
<211> LENGTH: 1555
<212> TYPE: DNA
<213> ORGANISM: Artificial Sequence
<220> FEATURE:
<223> OTHER INFORMATION: Variant 16

<400> SEQUENCE: 63

```
gacatccaga tgacccagtc tccatcctct ctgtccgcct ctgtgggcga cagagtgacc       60
atcacctgtc gggcttccaa gaccgtgtcc acctcctcct actcctacat gcactggtat      120
cagcagaagc ccggcaaggc ccctaagctg ctgattaagt acgcctccta cctggaatcc      180
ggcgtgccct ctagattctc cggctctggc tctggcaccg actttaccct gacaatctcc      240
agcctgcagc ctgaggactt cgccacctac tactgccagc actccagaga gttcccttgg      300 accttggcc agggcaccaa ggtggaaatc aagagagctg acgctgctcc tggcggcgga      360
ggatctggcg gaggtggaag cggaggcggt ggatctgaag tgcagctggt tgagagtggt      420
ggcggattgg ttcagcctgg cggatctctg agactgtctt gtgccgcctc tggcttcacc      480
ttctccaact acggcatgca ttgggtccga caggcccctg gcaaaggact ggaatgggtg      540
tcctacatct cctccggctc ctccaccatc tactacgccg actctgtgaa gggcagattc      600
accatctctc gggacaacgc caagaactcc ctgtacctgc agatgaacag cctgagagcc      660
gaggacaccg ccgtgtacta ctgtgctaga gaggcctgc tgctggacta ttggggccag       720
ggaacaaccg tgaccgtgtc tagcgcttcc acaagggcc cctctgtgtt ccctctggct      780
cctctggaat cttccggctc cgatattcag atgacacaga gcccttccag cctgtctgct     840
tccgtgggag atcgcgtgac aatcacatgc agagccagca agacagtgtc taccagcagc      900
tacagctata tgcattggta tcaacaaaaa cccgggaaag ctcccaagct cctgatcaaa      960
```

| | |
|---|---:|
| tacgccagct atctggaaag cggcgtgcca tctcggtttt ccggaagcgg ctctggaaca | 1020 |
| gactttacac tcaccattag ctccctccag ccagaggatt tgctaccta ttattgccag | 1080 |
| catagccgcg agtttccatg gacattcgga cagggaacta aggtcgagat caagcgggcc | 1140 |
| gatgctgcac ctggcggagg cggttcaggt ggcggtggtt caggcggtgg tggctctgag | 1200 |
| gttcagttgg tcgagtcagg cggaggactt gttcaaccag gcggaagcct gagactgagc | 1260 |
| tgtgctgcta gcggctttac cttcagcaat tacggaatgc actgggttcg ccaagctcca | 1320 |
| ggcaaaggct tggagtgggt ttcatatatc tccagcggca gcagcaccat ctattatgct | 1380 |
| gacagcgtga aaggccggtt caccatcagc agagataatg ccaagaacag cctctatctc | 1440 |
| caaatgaact ctctccgcgc tgaggatacc gctgtgtatt attgcgcccg cagaggactc | 1500 |
| ctgctcgatt actggggaca gggcactaca gtgacagtgt cctcctgatg aattc | 1555 |

<210> SEQ ID NO 64
<211> LENGTH: 1555
<212> TYPE: DNA
<213> ORGANISM: Artificial Sequence
<220> FEATURE:
<223> OTHER INFORMATION: Variant 17

<400> SEQUENCE: 64

| | |
|---|---:|
| gacatccaga tgacccagtc tccatcctct ctgtccgcct ctgtgggcga cagagtgacc | 60 |
| atcacctgtc gggcttccaa gaccgtgtcc acctcctcct actcctacat gcactggtat | 120 |
| cagcagaagc ccggcaaggc ccctaagctg ctgattaagt acgcctccta cctggaatcc | 180 |
| ggcgtgccct ctagattctc cggctctggc tctggcaccg actttaccct gacaatctcc | 240 |
| agcctgcagc ctgaggactt cgccacctac tactgccagc actccagaga gttcccttgg | 300 |
| acctttggcc agggcaccaa ggtggaaatc aagagagctg acgctgctcc tggcggcgga | 360 |
| ggatctggcg gaggtggaag cggaggcggt ggatctgaag tgcagctggt tgagagtggt | 420 |
| ggcggagttg ttcagcctgg cggatctctg agactgtctt gtgccgcctc tggcttcacc | 480 |
| ttctccaact acggcatgca ttgggtccga caggcccctg agaaaggcct ggaatgggtg | 540 |
| tcctacatct cctccggctc ctccaccatc tactacgccg actctgtgaa gggcagattc | 600 |
| accatcagcc gggacaactc caagaacacc ctgtacctgc agatgaactc cctgagagcc | 660 |
| gaggacaccg ccgtgtacta ctgtgctaga gaggcctgc tgctggacta ttggggccag | 720 |
| ggaacaaccg tgaccgtgtc tagcgcttcc acaaagggcc cctctgtgtt ccctctggct | 780 |
| cctctggaat cttccggctc cgatattcag atgacacaga gcccttccag cctgtctgct | 840 |
| tccgtgggag atcgcgtgac aatcacatgc agagccagca agacagtgtc taccagcagc | 900 |
| tacagctata tgcattggta tcaacaaaaa cccgggaaag ctcccaagct cctgatcaaa | 960 |
| tacgccagct atctggaaag cggcgtgcca tctcggtttt ccggaagcgg ctctggaaca | 1020 |
| gactttacac tcaccattag ctccctccag ccagaggatt tgctaccta ttattgccag | 1080 |
| catagccgcg agtttccatg gacattcgga cagggaacta aggtcgagat caagcgggcc | 1140 |
| gatgctgcac ctggcggagg cggttcaggt ggtggtggat caggtggcgg aggcagtgaa | 1200 |
| gtccagttgg tggaatcagg cggtggcgtt gtgcaacctg gtggaagtct gaggctgtcc | 1260 |
| tgcgctgctt ccggctttac cttcagcaat tacggaatgc actgggttcg ccaagctcca | 1320 |
| gagaagggac ttgagtgggt ttcctatatc agctccggca gcagcaccat ctattatgct | 1380 |
| gacagcgtga aaggccggtt caccatctcc agagacaaca gcaagaatac tctgtatctc | 1440 |
| caaatgaata gcctgcgcgc cgaggataca gctgtgtatt attgcgccag acggggactc | 1500 |

```
ctgctggatt actggggaca aggcactaca gtgacagtgt cctcctgatg aattc         1555
```

<210> SEQ ID NO 65
<211> LENGTH: 1555
<212> TYPE: DNA
<213> ORGANISM: Artificial Sequence
<220> FEATURE:
<223> OTHER INFORMATION: Variant 18

<400> SEQUENCE: 65

```
gacatccaga tgacccagtc tccatcctct ctgtccgcct ctgtgggcga cagagtgacc      60
atcacctgtc gggcttccaa gaccgtgtcc acctcctcct actcctacat gcactggtat    120
cagcagaagc ccggcaaggc ccctaagctg ctgattaagt acgcctccta cctggaatcc    180
ggcgtgccct ctagattctc cggctctggc tctggcaccg actttaccct gacaatctcc    240
agcctgcagc ctgaggactt cgccacctac tactgccagc actccagaga gttcccttgg    300
acctttggcc agggcaccaa ggtggaaatc aagagagctg acgctgctcc tggcggcgga    360
ggatctggcg gaggtggaag cggaggcggt ggatctgaag tgcagctggt tgagagtggc    420
ggaggcgacg tgaaacctgg cggatctctg agactgtctt gtgccgcctc tggcttcacc    480
ttctccaact acggcatgca ttgggtccga caggcccctg agaaaggcct ggaatgggtg    540
tcctacatct cctccggctc ctccaccatc tactacgccg actctgtgaa gggcagattc    600
accatcagcc gggacaactc caagaacacc ctgtacctgc agatgaactc cctgagagcc    660
gaggacaccg ccgtgtacta ctgtgctaga gaggcctgc tgctgactat ttggggccag    720
ggaacaaccg tgaccgtgtc tagcgcttcc acaaagggcc cctctgtgtt ccctctggct    780
cctctggaat cttccggctc cgatattcag atgacacaga gcccttccag cctgtctgct    840
tccgtgggag atcgcgtgac aatcacatgc agagccagca gacagtgtc taccagcagc    900
tacagctata tgcattggta tcaacaaaaa cccgggaaag ctcccaagct cctgatcaaa    960
tacgccagct atctggaaag cggcgtgcca tctcggtttt ccggaagcgg ctctggaaca   1020
gactttacac tcaccattag ctccctccag ccagaggatt ttgctaccta ttattgccag   1080
catagccgcg agtttccatg gacattcgga cagggaacta aggtcgagat caagcgggcc   1140
gatgctgcac caggcggtgg tggttcaggc ggaggcggta gcggcggagg cggctctgaa   1200
gttcaattgg tggaatcagg tggcggggat gtcaagcctg gtggaagtct gagactcagc   1260
tgtgccgcca gcggctttac cttcagcaat tacggaatgc actgggttcg ccaagctcca   1320
gagaagggac ttgagtgggt ttcctatatc agctccggca gcagcaccat ctattatgct   1380
gacagcgtga aaggccggtt caccatctcc agagacaaca gcaagaatac tctgtatctc   1440
caaatgaaca gcctgcgcgc cgaggataca gctgtgtatt attgcgccag acggggactc   1500
ctgctggatt actggggaca aggcactaca gtgacagtgt cctcctgatg aattc         1555
```

<210> SEQ ID NO 66
<211> LENGTH: 1555
<212> TYPE: DNA
<213> ORGANISM: Artificial Sequence
<220> FEATURE:
<223> OTHER INFORMATION: Variant 19

<400> SEQUENCE: 66

```
gacatccaga tgacccagtc tccatcctct ctgtctgctt ccctgggcga cagagccacc      60
atcacctgta gagcctccaa gaccgtgtcc acctcctcct actcctacat gcactggtat    120
```

| | |
|---|---|
| cagcagaagc ccggccaggc tcctaagctg ctgattaagt acgcctccta cctggaatcc | 180 |
| ggcgtgccct ctagattctc cggctctggc tctggcaccg actttaccct gacaatctcc | 240 |
| agcctgcagc ctgaggactt cgccacctac tactgccagc actccagaga gttcccttgg | 300 |
| acctttggcc agggcaccaa ggtggaaatc aagagagctg acgctgctcc tggcggcgga | 360 |
| ggatctggcg gaggtggaag cggaggcggt ggatctgaag tgcagctggt tgagagtggt | 420 |
| ggcggattgg ttcagcctgg cggatctctg agactgtctt gtgccgcctc tggcttcacc | 480 |
| ttctccaact acggcatgca ttgggtccga caggcccctg gcaaaggact ggaatgggtg | 540 |
| tcctacatct cctccggctc ctccaccatc tactacgccg actctgtgaa gggcagattc | 600 |
| accatctctc gggacaacgc caagaactcc ctgtacctgc agatgaacag cctgagagcc | 660 |
| gaggacaccg ccgtgtacta ctgtgctaga gaggcctgc tgctggacta ttggggccag | 720 |
| ggaacaaccg tgaccgtgtc tagcgcttcc acaaagggcc cctctgtgtt ccctctggct | 780 |
| cctctggaat cttccggctc cgatattcag atgacacaga gcccttccag cctgtccgcc | 840 |
| tctctgggag atagagctac aatcacatgc cgggccagca gacagtgtc taccagcagc | 900 |
| tacagctata tgcattggta tcaacaaaaa cccgggcaag ccccaaagct cctgatcaaa | 960 |
| tacgccagct atctggaaag cggcgtgcca tctcggtttt ccggaagcgg ctctggaaca | 1020 |
| gactttacac tcaccattag ctccctccag ccagaggatt ttgctaccta ttattgccag | 1080 |
| catagccgcg agtttccatg gacattcgga caggggaacta aggtcgagat caagcgggcc | 1140 |
| gatgctgcac ctggcggagg cggttcaggt ggcggaggca gcggtggcgg cggtagtgaa | 1200 |
| gttcagttgg tcgagtcagg cggcggactt gttcaaccag tggtagcct gagactgagc | 1260 |
| tgtgctgctt ccggctttac cttcagcaat tacggaatgc actgggttcg ccaagctcca | 1320 |
| ggcaaaggct tggagtgggt ttcatatatc tccagcggca gcagcaccat ctattatgct | 1380 |
| gacagcgtga aaggccggtt caccatcagc agagataatg ccaagaacag cctctacctc | 1440 |
| caaatgaact cactgcgcgc tgaggatacc gctgtgtatt attgcgcccg cagaggactc | 1500 |
| ctgctcgatt actggggaca gggcactaca gtgacagtgt cctcctgatg aattc | 1555 |

<210> SEQ ID NO 67
<211> LENGTH: 1555
<212> TYPE: DNA
<213> ORGANISM: Artificial Sequence
<220> FEATURE:
<223> OTHER INFORMATION: Variant 19

<400> SEQUENCE: 67

| | |
|---|---|
| gacatccaga tgacccagtc tccatcctct ctgtctgctt ccctgggcga cagagccacc | 60 |
| atcacctgta gagcctccaa gaccgtgtcc acctcctcct actcctacat gcactggtat | 120 |
| cagcagaagc ccggccaggc tcctaagctg ctgattaagt acgcctccta cctggaatcc | 180 |
| ggcgtgccct ctagattctc cggctctggc tctggcaccg actttaccct gacaatctcc | 240 |
| agcctgcagc ctgaggactt cgccacctac tactgccagc actccagaga gttcccttgg | 300 |
| acctttggcc agggcaccaa ggtggaaatc aagagagctg acgctgctcc tggcggcgga | 360 |
| ggatctggcg gaggtggaag cggaggcggt ggatctgaag tgcagctggt tgagagtggt | 420 |
| ggcggattgg ttcagcctgg cggatctctg agactgtctt gtgccgcctc tggcttcacc | 480 |
| ttctccaact acggcatgca ttgggtccga caggcccctg gcaaaggact ggaatgggtg | 540 |
| tcctacatct cctccggctc ctccaccatc tactacgccg actctgtgaa gggcagattc | 600 |
| accatctctc gggacaacgc caagaactcc ctgtacctgc agatgaacag cctgagagcc | 660 |

-continued

```
gaggacaccg ccgtgtacta ctgtgctaga agaggcctgc tgctggacta ttggggccag      720
ggaacaaccg tgaccgtgtc tagcgcttcc acaaagggcc cctctgtgtt ccctctggct      780
cctctggaat cttccggctc cgatattcag atgacacaga gcccttccag cctgtccgcc      840
tctctgggag atagagctac aatcacatgc cgggccagca agacagtgtc taccagcagc      900
tacagctata tgcattggta tcaacaaaaa cccgggcaag ccccaaagct cctgatcaaa      960
tacgccagct atctggaaag cggcgtgcca ctctcggtttt ccggaagcgg ctctggaaca     1020
gactttacac tcaccattag ctccctccag ccagaggatt ttgctaccta ttattgccag     1080
catagccgcg agtttccatg gacattcgga cagggaacta aggtcgagat caagcgggcc     1140
gatgctgcac ctggcggagg cggttcaggt ggcggaggca gcggtggcgg cggtagtgaa     1200
gttcagttgg tcgagtcagg cggcggactt gttcaaccag gtggtagcct gagactgagc     1260
tgtgctgctt ccggctttac cttcagcaat tacggaatgc actgggttcg ccaagctcca     1320
ggcaaaggct tggagtgggt ttcatatatc tccagcggca gcagcaccat ctattatgct     1380
gacagcgtga aaggccggtt caccatcagc agagataatg ccaagaacag cctctacctc     1440
caaatgaact cactgcgcgc tgaggatacc gctgtgtatt attgcgcccg cagaggactc     1500
ctgctcgatt actggggaca gggcactaca gtgacagtgt cctcctgatg aattc         1555
```

<210> SEQ ID NO 68
<211> LENGTH: 446
<212> TYPE: PRT
<213> ORGANISM: Artificial Sequence
<220> FEATURE:
<223> OTHER INFORMATION: Full length heavy chain

<400> SEQUENCE: 68

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

```
Lys Val Asp Lys Lys Val Glu Pro Lys Ser Cys Asp Lys Thr His Thr
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 69
<211> LENGTH: 98
<212> TYPE: PRT
<213> ORGANISM: Artificial Sequence
<220> FEATURE:
<223> OTHER INFORMATION: IgG1 constant heavy region 1

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 70
<211> LENGTH: 12
```

```
<212> TYPE: PRT
<213> ORGANISM: Artificial Sequence
<220> FEATURE:
<223> OTHER INFORMATION: IgG1 hinge region

<400> SEQUENCE: 70

Glu Pro Lys Ser Cys Asp Lys Thr His Thr Cys Pro
1               5                   10

<210> SEQ ID NO 71
<211> LENGTH: 113
<212> TYPE: PRT
<213> ORGANISM: Artificial Sequence
<220> FEATURE:
<223> OTHER INFORMATION: IgG1 L2345A/L235A constant heavy region 2

<400> SEQUENCE: 71

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 72
<211> LENGTH: 107
<212> TYPE: PRT
<213> ORGANISM: Artificial Sequence
<220> FEATURE:
<223> OTHER INFORMATION: IgG1 constant heavy region 3

<400> SEQUENCE: 72

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 73
<211> LENGTH: 446
<212> TYPE: PRT
<213> ORGANISM: Artificial Sequence
```

<220> FEATURE:
<223> OTHER INFORMATION: IgG1 N297D heavy chain full length sequence

<400> SEQUENCE: 73

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asp Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 74
<211> LENGTH: 113
<212> TYPE: PRT
<213> ORGANISM: Artificial Sequence
<220> FEATURE:
<223> OTHER INFORMATION: IgG1 N297D constant heavy region 2

<400> SEQUENCE: 74

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asp Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 75
<211> LENGTH: 446
<212> TYPE: PRT
<213> ORGANISM: Artificial Sequence
<220> FEATURE:
<223> OTHER INFORMATION: IgG1 L2345A/L235A/N297D heavy chain full length
      sequence

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
```

```
                130             135             140
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asp Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 76
<211> LENGTH: 113
<212> TYPE: PRT
<213> ORGANISM: Artificial Sequence
<220> FEATURE:
<223> OTHER INFORMATION: IgG1 L2345A/L235A/N297D constant heavy region 2

<400> SEQUENCE: 76

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
```

```
Arg Glu Glu Gln Tyr Asp Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys

<210> SEQ ID NO 77
<211> LENGTH: 113
<212> TYPE: PRT
<213> ORGANISM: Artificial Sequence
<220> FEATURE:
<223> OTHER INFORMATION: Unmodified constant heavy region 2

<400> SEQUENCE: 77

Pro Cys Pro Ala Pro Glu Leu Leu Gly Gly Pro Ser Val Phe Leu Phe
 1               5                  10                  15

Pro Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Lys Phe
                 35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys

<210> SEQ ID NO 78
<211> LENGTH: 218
<212> TYPE: PRT
<213> ORGANISM: Artificial Sequence
<220> FEATURE:
<223> OTHER INFORMATION: Light chain full length sequence

<400> SEQUENCE: 78

Asp Ile Gln Met Thr Gln Ser Pro Ser Ser Leu Ser Ala Ser Leu Gly
 1               5                  10                  15

Asp Arg Ala Thr Ile Thr Cys Arg Ala Ser Lys Thr Val Ser Thr Ser
                 20                  25                  30

Ser Tyr Ser Tyr Met His Trp Tyr Gln Gln Lys Pro Gly Gln Pro Pro
                 35                  40                  45

Lys Leu Leu Ile Lys Tyr Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Ala Ala Thr Tyr Tyr Cys Gln His Ser Arg
                 85                  90                  95

Glu Phe Pro Trp Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
                115                 120                 125
```

```
Leu Lys Ser Gly Thr Ala Ser Val Val Cys Leu Leu Asn Asn Phe Tyr
    130             135                 140
Pro Arg Glu Ala Lys Val Gln Trp Lys Val Asp Asn Ala Leu Gln Ser
145             150                 155                 160
Gly Asn Ser Gln Glu Ser Val Thr Glu Gln Asp Ser Lys Asp Ser Thr
            165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

BINDING PROTEINS 1

FIELD OF THE INVENTION

The present disclosure relates to cell penetrating anti-DNA binding proteins. Compositions comprising these binding proteins may be useful for delivering agents to cells and treating diseases such as cancer.

BACKGROUND OF THE INVENTION

Development of cell penetrating anti-DNA binding proteins as therapeutic agents for human diseases has great clinical potential, in particular because of their ability to selectively impair DNA repair pathways and/or deliver various therapeutic payloads to target cells.

Accordingly, improved cell penetrating anti-DNA binding proteins are required.

SUMMARY OF THE INVENTION

The present inventors have identified cell penetrating anti-DNA binding protein modifications that surprisingly increase nuclear penetration. In some cases, these modifications may also improve physical stability and reduce immunogenicity.

Accordingly, in a first example, the present disclosure relates to a cell penetrating anti-DNA binding protein having an antigen binding domain, wherein the antigen binding domain binds to or specifically binds to DNA and comprises a heavy chain variable region ($V_H$) having a complementarity determining region (CDR) 1 as shown in SEQ ID NO: 1, a CDR2 as shown in SEQ ID NO: 2 or SEQ ID NO: 3 and a CDR3 as shown in SEQ ID NO: 4 and a light chain variable region ($V_L$) having a CDR1 as shown in SEQ ID NO: 5 or SEQ ID NO: 6, a CDR2 as shown in SEQ ID NO: 7 and a CDR3 as shown in SEQ ID NO: 8. In this example, the CDRs have been defined using Kabat.

In another example, the present disclosure relates to a cell penetrating anti-DNA binding protein having an antigen binding domain, wherein the antigen binding domain binds to or specifically binds to DNA and comprises:
- a heavy chain variable region ($V_H$) having a complementarity determining region (CDR) 1 as shown in SEQ ID NO: 9, a CDR2 as shown in SEQ ID NO: 10 or SEQ ID NO: 11 and a CDR3 as shown in SEQ ID NO: 12;
- a light chain variable region ($V_L$) having a CDR1 as shown in SEQ ID NO: 13 or SEQ ID NO: 14, a CDR2 as shown in SEQ ID NO: 15 and a CDR3 as shown in SEQ ID NO: 16. In this example, the CDRs have been defined using IMGT.

In another example, binding proteins according to the present disclosure comprise:
 (i) a $V_H$ comprising a sequence at least 95% identical to the sequence as shown in any one of SEQ ID NOs: 17 to 23;
 (ii) a $V_L$ comprising a sequence at least 95% identical to the sequence as shown in any one of SEQ ID NOs: 24 to 29; or
 (iii) a $V_H$ comprising a sequence at least 95% identical to the sequence as shown in any one of SEQ ID NOs: 17 to 23 and a $V_L$ comprising a sequence at least 95% identical to the sequence as shown in any one of SEQ ID NOs: 24 to 29. For example, the binding protein may comprise a sequence at least 95% identical to the sequence as shown in any one of SEQ ID NOs: 17 to 23. In another example, the binding protein may comprise a $V_L$ comprising a sequence at least 95% identical to the sequence as shown in any one of SEQ ID NOs: 24 to 29. In another example, the binding protein may comprise a $V_H$ comprising a sequence at least 95% identical to the sequence as shown in any one of SEQ ID NOs: 17 to 23 and a $V_L$ comprising a sequence at least 95% identical to the sequence as shown in any one of SEQ ID NOs: 24 to 29.

In another example, the $V_H$ and a $V_L$ are separated by a linker. For example, the linker may be comprise (Gly$_4$Ser)$_3$. In another example the linker comprises an amino acid sequence as shown in SEQ ID NO: 30.

In an example, the $V_H$ and $V_L$ are in a single polypeptide chain. For example, the binding protein may be:
 (i) a single chain Fv fragment (scFv);
 (ii) a dimeric scFv (di-scFv);
 (iii) a trimeric scFv (tri-scFv);
 (iv) any one of (i), (ii) or (iii) linked to a constant region of an antibody, Fc or a heavy chain constant domain $C_H2$ and/or $C_H3$. For example, the binding protein may be a di-scFv. In this example, the scFv's may be separated by a linker. For example, the linker may comprise an amino acid sequence as shown in SEQ ID NO: 31.

In another example, the $V_H$ and $V_L$ are in separate polypeptide chains. For example, the binding protein may be:
 (i) a diabody;
 (ii) a triabody;
 (iii) a tetrabody;
 (iv) a Fab;
 (v) a F(ab')$_2$;
 (vi) a Fv;
 (vii) one of (i) to (vi) linked to a constant region of an antibody, Fc or a heavy chain constant domain $C_H2$ and/or $C_H3$; or,
 (viii) an intact antibody.

Thus, the $V_H$ and $V_L$ of an Fv can be formed of a single peptide chain (e.g. scFv), or can be formed of two separate peptide chains.

In an example, the binding protein is humanized.

In another example, the present disclosure relates to a cell penetrating anti-DNA Fv fragment having an antigen binding domain, wherein the antigen binding domain binds to or specifically binds to DNA and comprises at least one of:
 a $V_H$ having a CDR 1 as shown in SEQ ID NO: 1, a CDR2 as shown in SEQ ID NO: 2 or SEQ ID NO: 3, a CDR3 as shown in SEQ ID NO: 4 and a $V_L$ having a CDR1 as shown in SEQ ID NO: 5 or SEQ ID NO: 6, a CDR2 as shown in SEQ ID NO: 7 and a CDR3 as shown in SEQ ID NO: 8;
 a $V_H$ having a CDR 1 as shown in SEQ ID NO: 9, a CDR2 as shown in SEQ ID NO: 10 or SEQ ID NO: 11, a CDR3 as shown in SEQ ID NO: 12 and a $V_L$ having a CDR1 as shown in SEQ ID NO: 13 or SEQ ID NO: 14, a CDR2 as shown in SEQ ID NO: 15 and a CDR3 as shown in SEQ ID NO: 16;
 a $V_H$ comprising a sequence at least 95% identical to the sequence as shown in any one of SEQ ID NOs: 17 to 23 and a $V_L$ comprising a sequence at least 95% identical to the sequence as shown in any one of SEQ ID NOs: 24 to 29.

In this example, the Fv fragment may be a di-scFv. In an example, the Fv fragment may comprise an amino acid sequence as shown in any one of SEQ ID NOs: 32-47. For example, the Fv fragment may comprise an amino acid sequence as shown in SEQ ID NO: 41.

In some embodiments, the Fv is naked. In another example, the Fv fragment may be conjugated to another compound.

In an example, the Fv is humanized. For example, the Fv may be a humanized di-scFv.

In another example, the present disclosure relates to a nucleic acid sequence encoding an above referenced binding proteins. Exemplary nucleic acid sequences are shown in SEQ ID NOs: 51-66. The disclosed nucleic acid sequences can be codon-optimized to increase levels of expression for synthesizing the proteins. In another example, the present disclosure relates to an expression vector comprising a nucleic acid sequence according to the present disclosure. For example, the expression vector may comprise a nucleic acid sequences are shown in any one of SEQ ID NOs: 51-66 or a codon optimized sequence thereof.

In another example, the present disclosure relates to a host cell comprising an above referenced binding protein, nucleic acid or vector, or codon optimized sequence thereof.

In another example, the present disclosure relates to a method of treating cancer. For example, a method of treating cancer comprising administering to a subject an Fv fragment comprising an amino acid sequence as shown in any one of SEQ ID NOs: 32, 36, 41 or 43. For example, an Fv fragment comprising an amino acid sequence as shown in SEQ ID NOs: 32 may be administered to a subject. In another example, an Fv fragment comprising an amino acid sequence as shown in SEQ ID NOs: 36 may be administered to a subject. In another example, an Fv fragment comprising an amino acid sequence as shown in SEQ ID NOs: 41 may be administered to a subject. In another example, an Fv fragment comprising an amino acid sequence as shown in SEQ ID NOs: 43 may be administered to a subject. In an example, the cancer is colon cancer, brain cancer, prostate cancer, ovarian cancer, endometrial cancer, breast cancer, or pancreatic cancer. For example, the cancer may be colon cancer or brain cancer. In an example, the cancer is brain cancer. In an example, the brain cancer is glioblastoma.

In another example, the present disclosure relates to use of a binding protein such as an Fv fragment, composition, vector or host cell according to the present disclosure in the manufacture of a medicament for treating cancer. In another example, the present disclosure relates to a binding protein such as an Fv fragment, composition, vector or host cell according to the present disclosure for use in treating cancer.

The experimental results below also illustrate that binding proteins disclosed herein can work with poly (ADP-ribose) polymerase (PARP) inhibitors to kill cancer cells. Accordingly, in another example, the present disclosure relates to a method of treating cancer in a subject in need thereof, the method comprising administering to the subject a binding protein or Fv fragment defined herein and a PARP inhibitor.

In an example, the PARP inhibitor is olaparib.

In an example, the cancer is substantially HDR deficient. In another example, the cancer is substantially BRCA2 deficient. In another example, the cancer is substantially PTEN deficient. In an example, the cancer is colon cancer, brain cancer, prostate cancer, ovarian cancer, endometrial cancer, breast cancer, or pancreatic cancer. For example, the cancer may be colon cancer or brain cancer. In an example, the cancer is brain cancer. In an example, the brain cancer is glioblastoma. In an example, the cancer is resistant to PARP inhibition. For example, the cancer may be resistant to treatment with olaparib. In another example, the cancer is triple negative breast cancer.

In another example, the present disclosure relates to a therapeutic combination comprising a binding protein or Fv fragment defined herein and a PARP inhibitor, the combination being provided for simultaneous or sequential administration. In another example, the present disclosure relates to a therapeutic combination comprising:

a binding protein or Fv comprising the CDRs of SEQ ID NOs: 41; or, a binding protein comprising the amino acid sequence shown in SEQ ID NO: 41;

and, a PARP inhibitor, the combination being provided for simultaneous or sequential administration. For example, the binding protein or Fv can comprise heavy chain CDRs as shown in SEQ ID NOs: 1, 3 and 4 and light chain CDRs as shown in SEQ ID NOs: 6, 7 and 8. In these examples, the therapeutic combination may be used for treating cancer. Furthermore, in these examples, the PARP inhibitor may be olaparib.

Any example herein shall be taken to apply mutatis mutandis to any other example unless specifically stated otherwise.

The present disclosure is not to be limited in scope by the specific examples described herein, which are intended for the purpose of exemplification only. Functionally-equivalent products, compositions and methods are clearly within the scope of the disclosure, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The disclosure is hereinafter described by way of the following non-limiting Examples and with reference to the accompanying drawings.

BRIEF DESCRIPTION OF THE ACCOMPANYING DRAWINGS

FIG. 1. Images illustrating the results of SDS-PAGE analysis of reduced and denatured variants.

FIG. 2. Images illustrating the results of SDS-PAGE analysis of non-reduced variants.

FIG. 3. Images illustrating the results of Alkaline phosphatase-based survey of nuclear penetration.

Figure 4:
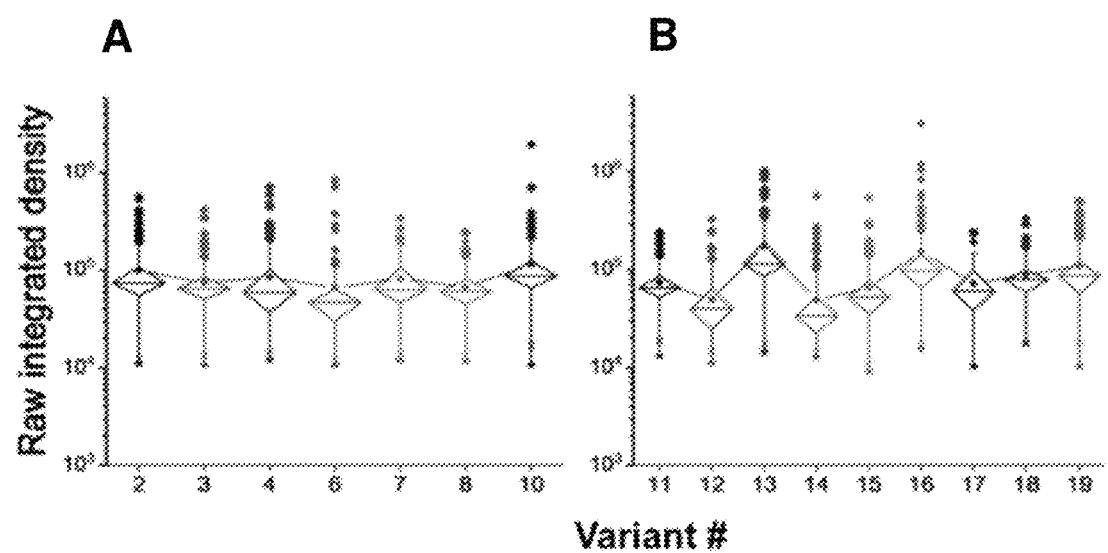

FIG. 4. Plots showing Quantitative analysis of the alkaline phosphatase-based survey of nuclear penetration.

FIG. 5. Histograms of Quantitative analysis of the alkaline phosphatase-based survey of nuclear penetration.

Figure 6:
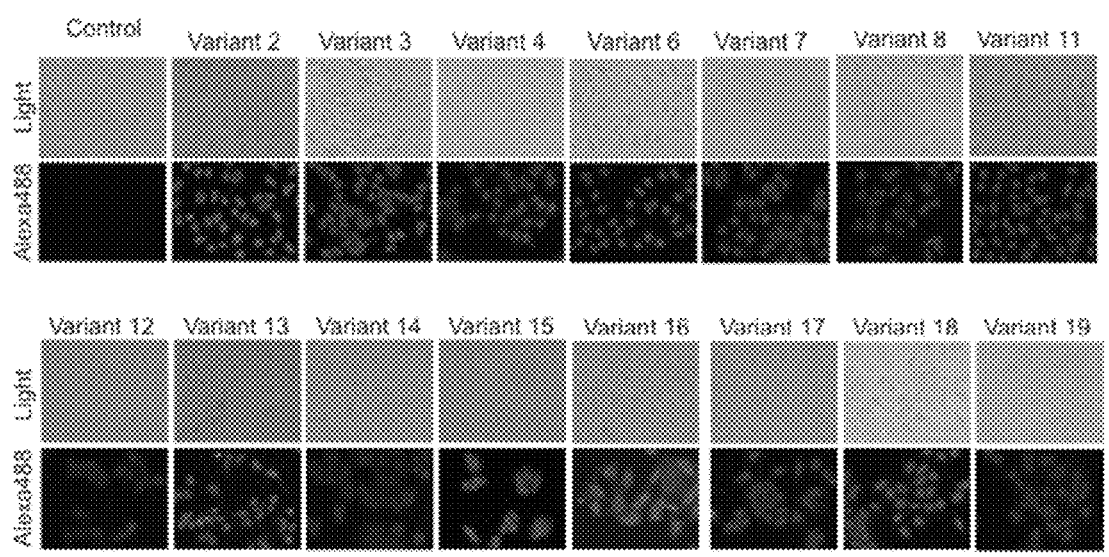

FIG. 6. Images illustrating the results of Immunofluorescence-based survey of nuclear penetration.

Figure 7:
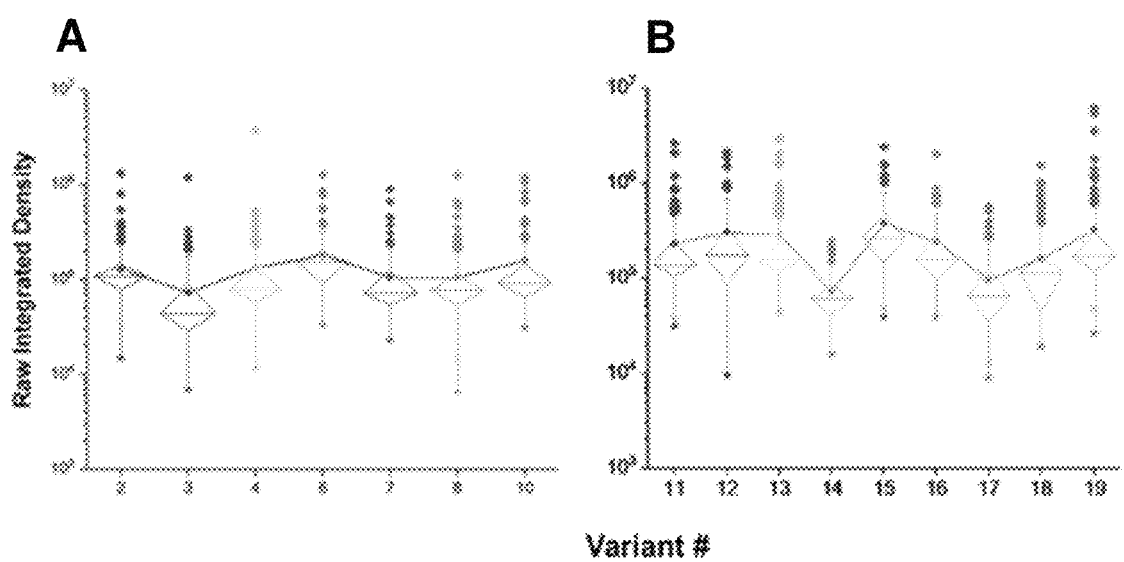

FIG. 7. Plots showing Quantitative analysis of the immunofluorescence-based survey of nuclear penetration.

Figure 8:
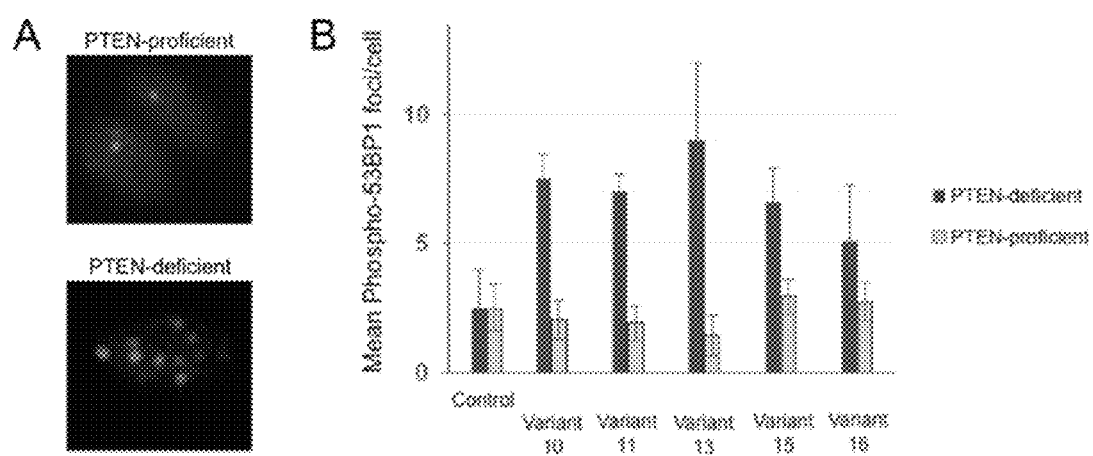

FIG. 8, Panel A. Exemplary images showing Accumulation of DNA damage in PTEN-proficient and PTEN-deficient cancer cells.

FIG. 8, Panel B. Histogram showing Accumulation of DNA damage in PTEN-proficient and PTEN-deficient cancer cells.

Figure 9:
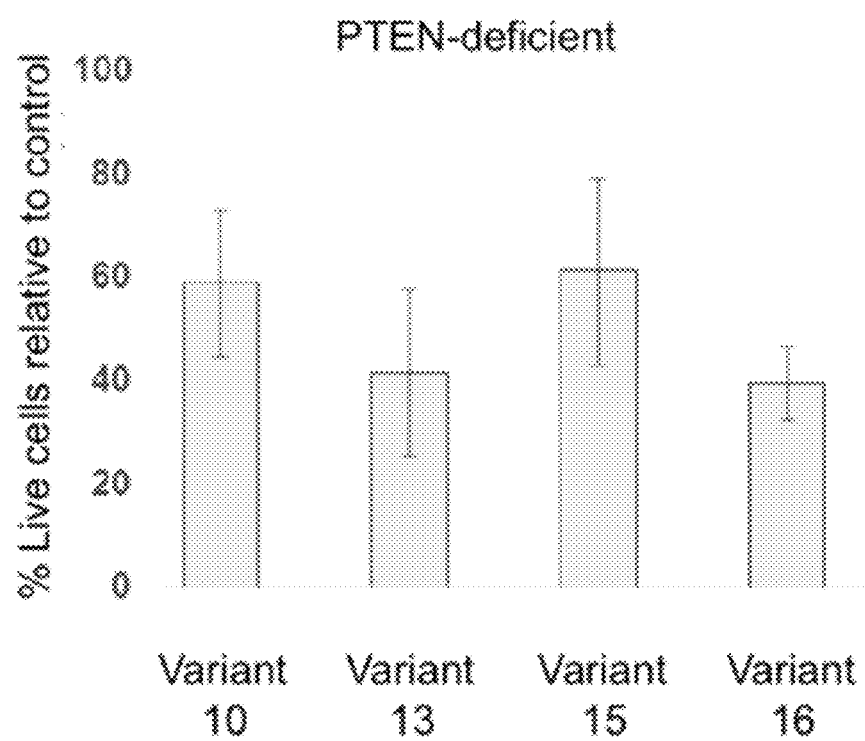

FIG. 9. Histogram showing Cell viability of PTEN-deficient cancer cells.

Figure 10:
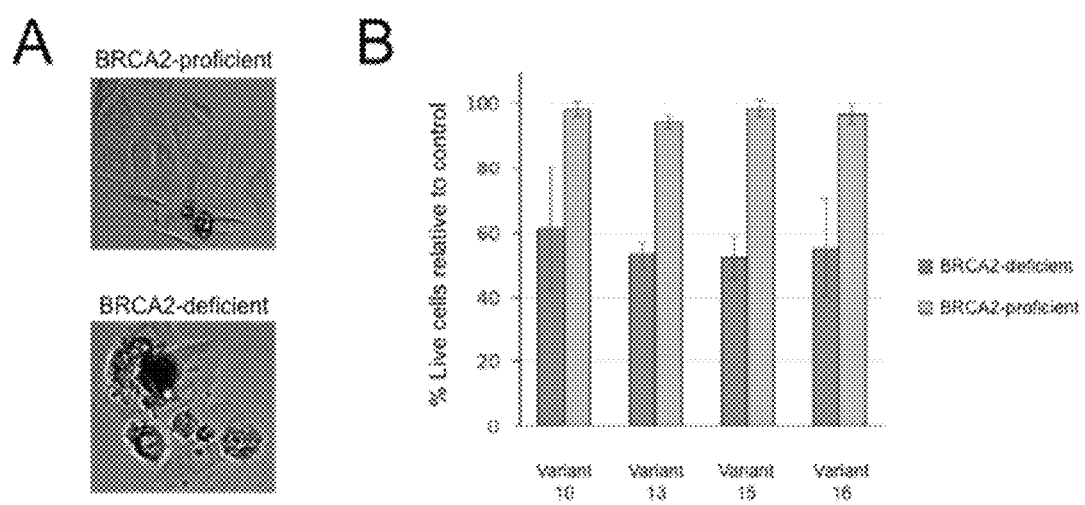

FIG. 10, Panel A. Exemplary images showing Accumulation of DNA damage in BRCA2-proficient and BRCA2-deficient cancer cells.

FIG. 10, Panel B. Histogram showing Accumulation of DNA damage in BRCA2-proficient and BRCA2-deficient cancer cells.

FIG. 11. di-scFv (SEQ ID NO: 41) penetrates HDR deficient DLD-1 colon cancer cell nuclei.

Figure 12:
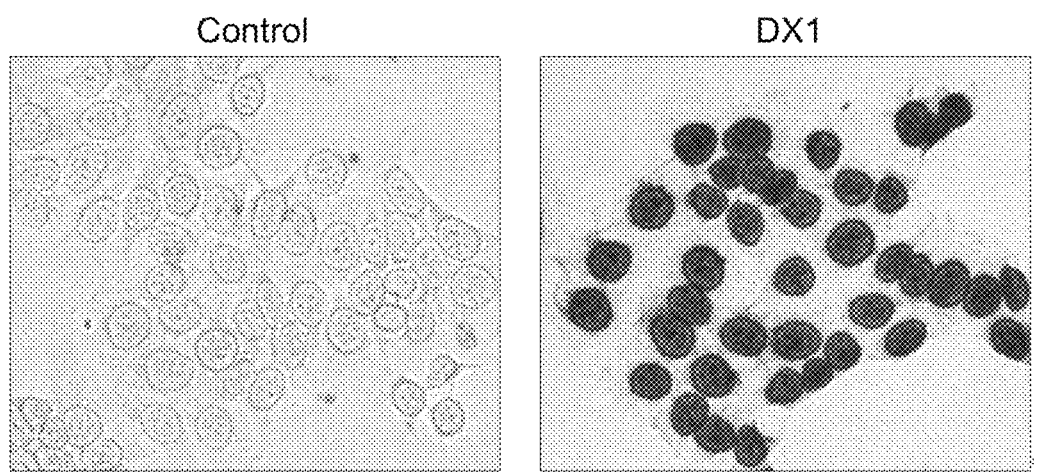

FIG. 12. di-scFv (SEQ ID NO: 41) penetrates HDR deficient MCF-7 breast cancer cell nuclei.

Figure 13:
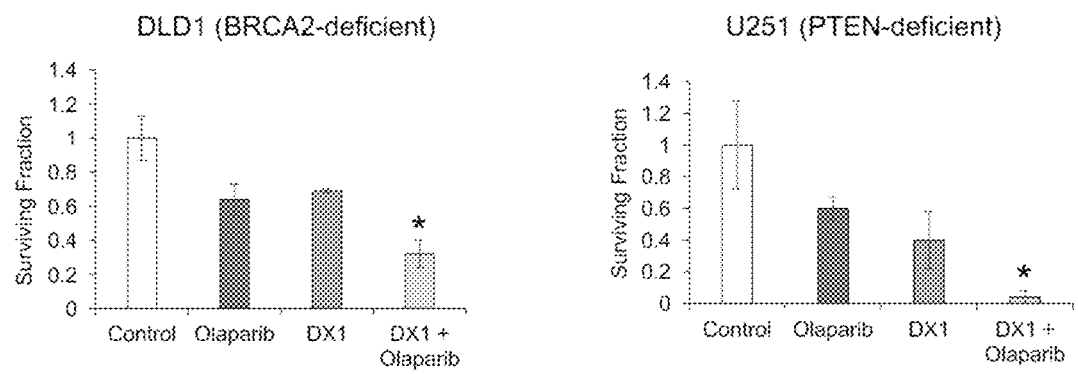

FIG. 13. More than additive cell death mediated by di-scFv (SEQ ID NO: 41) and PARP inhibitor in HDR deficient cancer cells (*p<0.05 compared to olaparib or the di-scFv alone).

Figure 14:
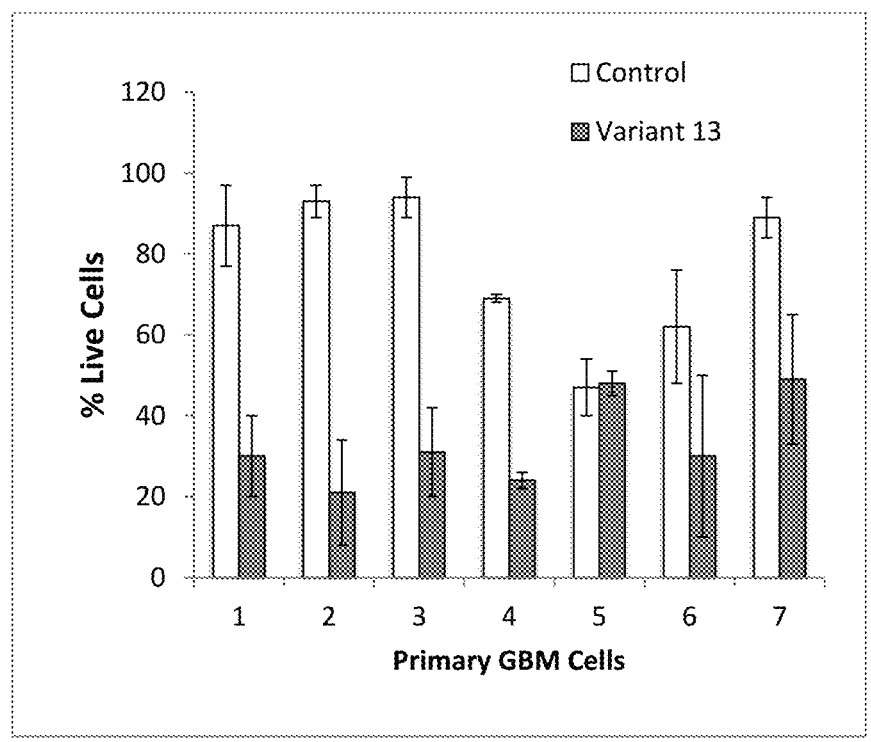

FIG. 14. di-scFv (SEQ ID NO: 41) kills primary human glioblastoma cells.

Figure 15:
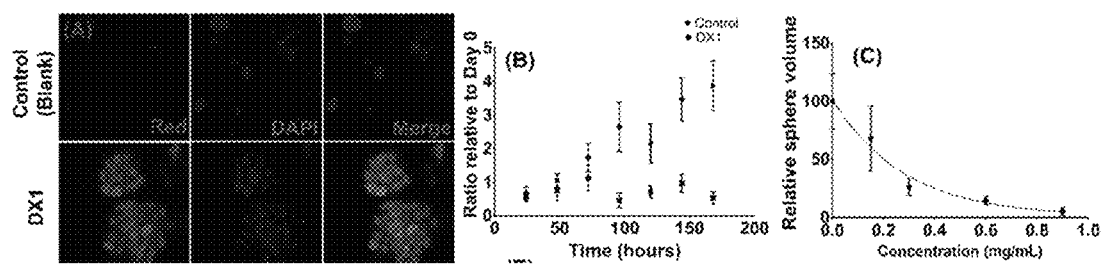

FIG. 15. di-scFv (SEQ ID NO: 41) penetrates human glioblastoma spheres (A) and reduces sphere volume in a time-dependent (B) and dose-dependent (C) manner.

Figure 16:
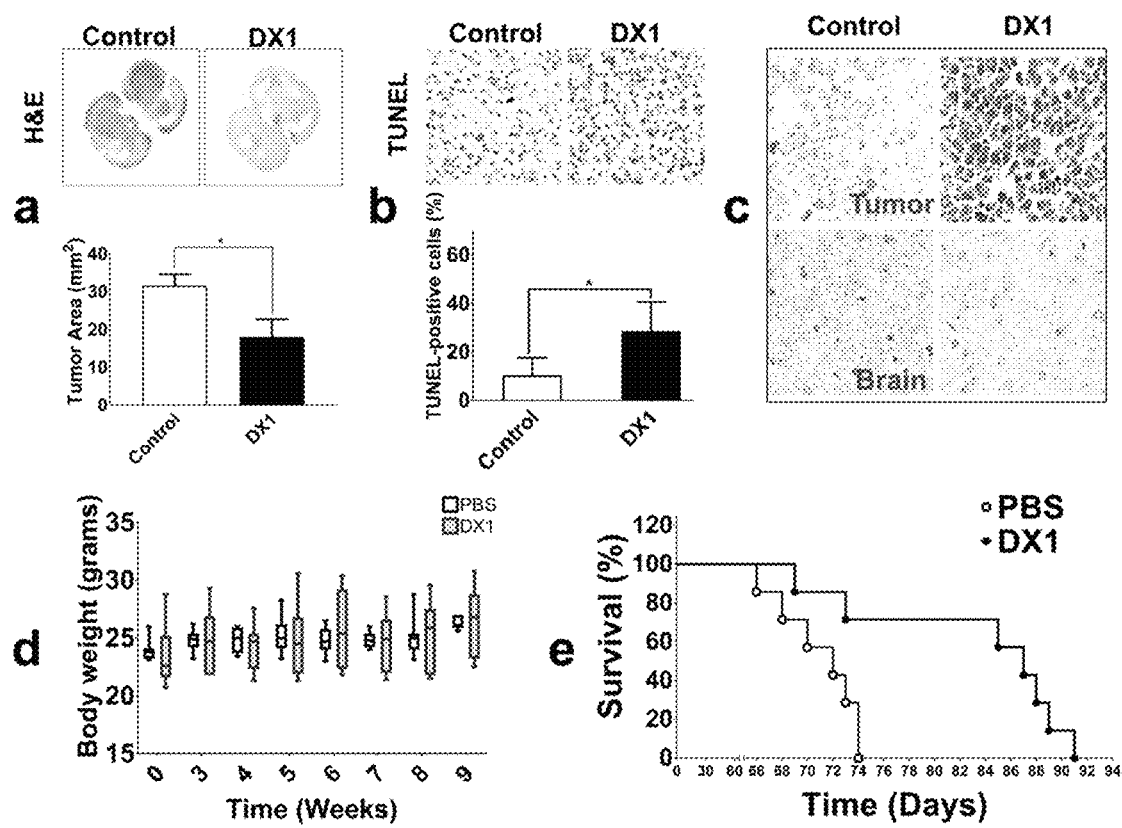

FIG. 16. In-vivo assessment of di-scFv (SEQ ID NO: 41) in a orthotopic mouse model of glioblastoma. a) Representative H&E stained brain sections from mice treated with control or di-scFv (SEQ ID NO: 41) and corresponding quantification of area. (*P<0.04, n=3). b) Representative micrographs of TUNEL staining, and corresponding percentage of TUNEL-positive cells. * denotes a P≤0.05 as determined by a one-way ANOVA test. c) Protein L-based immunostaining for comparison of di-scFv (SEQ ID NO: 41) in tumour and adjacent brain tissue. d) Body weight (grams) profile for mice in the survival study (n=7). e) Survival data for control PBS versus di-scFv (SEQ ID NO: 41) treatment arms (n=7, P=0.02, Mantel-Cox test).

Figure 17:
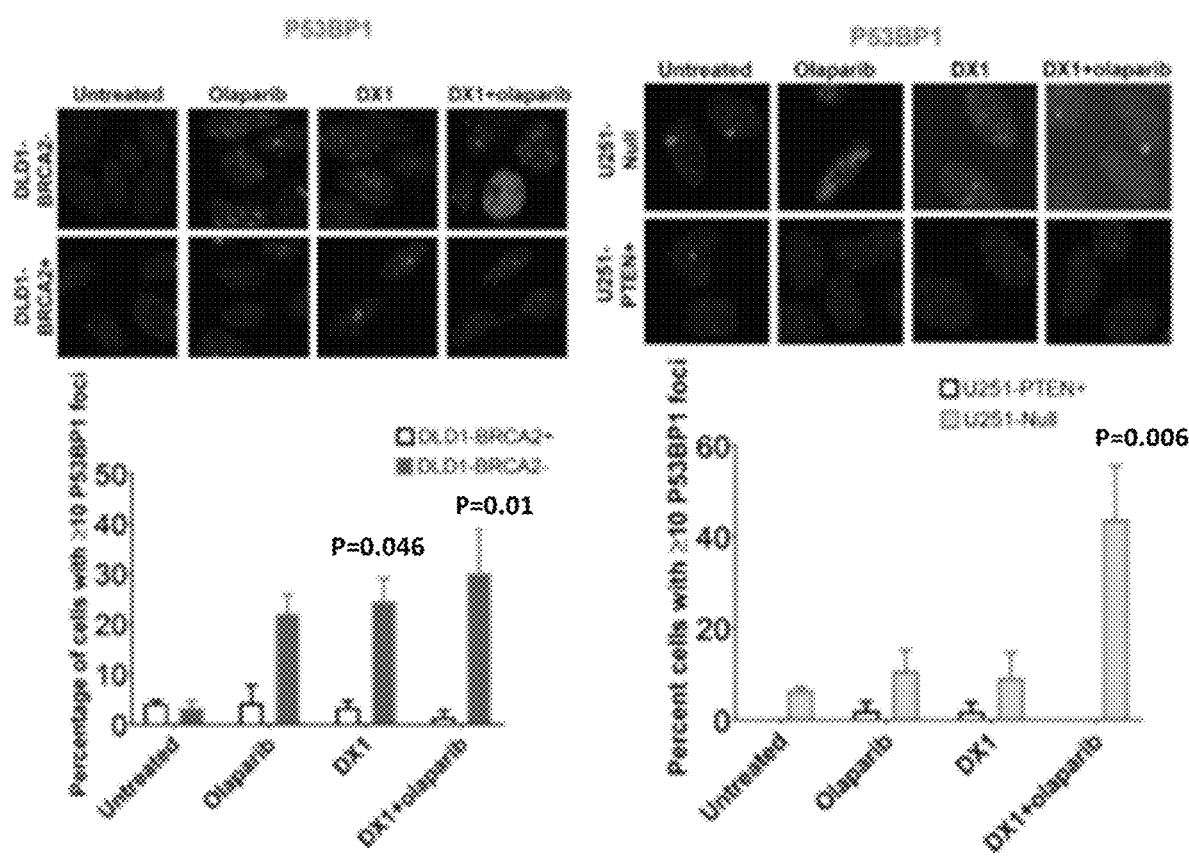

FIG. 17. Effect of di-scFv (SEQ ID NO: 41) on Foci Accumulation. The percentage of P53BP1-positive cells increased in HDR-deficient DLD1 and U251 cells following 24 hour PAT-DX1 and combination treatment(s).

KEY TO SEQUENCE LISTING

SEQ ID NO: 1—Heavy Chain CDR1 KABAT
SEQ ID NO: 2—Heavy Chain CDR2 (variants 2-4, 6-8, 10-12) KABAT
SEQ ID NO: 3—Heavy Chain CDR2 (variants 13-19) KABAT
SEQ ID NO: 4—Heavy Chain CDR3 KABAT
SEQ ID NO: 5—Light Chain CDR1 (variants 2-4, 6-8, 10-12) KABAT
SEQ ID NO: 6—Light Chain CDR1 (variants 13-19) KABAT
SEQ ID NO: 7—Light Chain CDR2 KABAT
SEQ ID NO: 8—Light Chain CDR3 KABAT
SEQ ID NO: 9—Heavy Chain CDR1 IMGT
SEQ ID NO: 10—Heavy Chain CDR2 (variants 2-4, 6-8, 10-12) IMGT
SEQ ID NO: 11—Heavy Chain CDR2 (variants 13-19) IMGT
SEQ ID NO: 12—Heavy Chain CDR3 IMGT
SEQ ID NO: 13—Light Chain CDR1 (variants 2-4, 6-8, 10-12) IMGT
SEQ ID NO: 14—Light Chain CDR1 (variants 13-19) IMGT
SEQ ID NO: 15—Light Chain CDR2 IMGT
SEQ ID NO: 16—Light Chain CDR3 IMGT
SEQ ID NO: 17—Heavy Chain variable region (variants 2, 6 and 10)
SEQ ID NO: 18—Heavy Chain variable region (variants 3, 7 and 11)
SEQ ID NO: 19—Heavy Chain variable region (variants 4, 8 and 12)
SEQ ID NO: 20—Heavy Chain variable region (variants 6 and 10)
SEQ ID NO: 21—Heavy Chain variable region (variants 13, 16 and 19)
SEQ ID NO: 22—Heavy Chain variable region (variants 14 and 17)
SEQ ID NO: 23—Heavy Chain variable region (variants 15 and 18)
SEQ ID NO: 24—Light Chain variable region (variants 2, 3 and 4)
SEQ ID NO: 25—Light Chain variable region (variants 6, 7 and 8)
SEQ ID NO: 26—Light Chain variable region (variants 10, 11 and 12)
SEQ ID NO: 27—Light Chain variable region (variants 13, 14 and 15)
SEQ ID NO: 28—Light Chain variable region (variants 16, 17 and 18)
SEQ ID NO: 29—Light Chain variable region (variant 19)
SEQ ID NO: 30—Linker sequence 1
SEQ ID NO: 31—Linker sequence 2
SEQ ID NO: 32—Variant 2
SEQ ID NO: 33—Variant 3
SEQ ID NO: 34—Variant 4
SEQ ID NO: 35—Variant 6
SEQ ID NO: 36—Variant 7
SEQ ID NO: 37—Variant 8
SEQ ID NO: 38—Variant 10
SEQ ID NO: 39—Variant 11
SEQ ID NO: 40—Variant 12
SEQ ID NO: 41—Variant 13
SEQ ID NO: 42—Variant 14
SEQ ID NO: 43—Variant 15
SEQ ID NO: 44—Variant 16
SEQ ID NO: 45—Variant 17
SEQ ID NO: 46—Variant 18
SEQ ID NO: 47—Variant 19
SEQ ID NO: 0.48—Heavy Chain variable region murine (D31N) anti-DNA binding antibody
SEQ ID NO: 49—Light Chain variable region murine (D31N) anti-DNA binding antibody
SEQ ID NO: 50—(D31N) murine prototype produced from *P. pastoris*
SEQ ID NO: 51—DNA sequence Variant 2
SEQ ID NO: 52—DNA sequence Variant 3
SEQ ID NO: 53—DNA sequence Variant 4
SEQ ID NO: 54—DNA sequence Variant 6
SEQ ID NO: 55—DNA sequence Variant 7
SEQ ID NO: 56—DNA sequence Variant 8
SEQ ID NO: 57—DNA sequence Variant 10
SEQ ID NO: 58—DNA sequence Variant 11
SEQ ID NO: 59—DNA sequence Variant 12
SEQ ID NO: 60—DNA sequence Variant 13
SEQ ID NO: 61—DNA sequence Variant 14
SEQ ID NO: 62—DNA sequence Variant 15
SEQ ID NO: 63—DNA sequence Variant 16
SEQ ID NO: 64—DNA sequence Variant 17
SEQ ID NO: 65—DNA sequence Variant 18
SEQ ID NO: 66—DNA sequence Variant 19
SEQ ID NO: 67—(GGGGS)$_3$ linker
SEQ ID NO: 68-3E10 human IgG1 L2345A/L235A heavy chain full length sequence
SEQ ID NO: 69-3E10 human IgG1 constant heavy region 1
SEQ ID NO: 70-3E10 human IgG1 hinge region
SEQ ID NO: 71-3E10 human IgG1 L2345A/L235A constant heavy region 2
SEQ ID NO: 72-3E10 human IgG1 constant heavy region 3
SEQ ID NO: 73-3E10 human IgG1 N297D heavy chain full length sequence SEQ ID NO: 74-3E10 human IgG1 N297D constant heavy region 2

SEQ ID NO: 75-3E10 human IgG1 L2345A/L235A/N297D heavy chain full length sequence SEQ ID NO: 76-3E10 human IgG1 L2345A/L235A/N297D constant heavy region 2

SEQ ID NO: 77—Unmodified constant heavy region 2

SEQ ID NO: 78—Light chain full length sequence

DETAILED DESCRIPTION OF THE INVENTION

General Techniques and Selected Definitions

Unless specifically defined otherwise, all technical and scientific terms used herein shall be taken to have the same meaning as commonly understood by one of ordinary skill in the art (e.g., molecular biology, biochemistry, antibodies, antibody fragments such as single chain fragment variable and clinical studies).

The term "cell-penetrating" is used in the context of the present disclosure to refer to an anti-DNA binding protein such as an antigen binding fragment that is transported into the nucleus of living mammalian cells and binds DNA (e.g., single-stranded and/or double-stranded DNA). In an example, a cell-penetrating anti-DNA binding protein is transported into the nucleus of a cell without the aid of a carrier or conjugate.

The term "anti-DNA binding protein" is used in the context of the present disclosure to refer to proteins capable of binding DNA. Exemplary binding proteins include immunoglobulin, antibodies and antigenic binding fragments. Other examples of binding proteins are discussed below.

The term "immunoglobulin" will be understood to include any anti-DNA binding protein comprising an immunoglobulin domain. Exemplary immunoglobulins are antibodies. Additional proteins encompassed by the term "immunoglobulin" include domain antibodies, camelid antibodies and antibodies from cartilaginous fish (i.e., immunoglobulin new antigen receptors (IgNARs)). Generally, camelid antibodies and IgNARs comprise a $V_H$, however lack a $V_L$ and are often referred to as heavy chain immunoglobulins. Other "immunoglobulins" include T cell receptors.

The term "antibody" is used in the context of the present disclosure to refer to immunoglobulin molecules immunologically reactive with a particular antigen and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG as discussed in Pierce Catalogue and Handbook, 1994-1995 (Pierce Chemical Co., Rockford, Ill.); Kuby, J., Immunology, 3$^{rd}$ Ed., W.H. Freeman & Co., New York (1998). The term is also used to refer to recombinant single chain Fv fragments (scFv) as well as divalent (di-scFv) and trivalent (tri-scFV) forms thereof. The term antibody also includes bivalent or bispecific molecules, diabodies, triabodies, and tetrabodies. Examples of bivalent and bispecific molecules are described in Kostelny et al. (1992) J Immunol 148:1547; Pack and Pluckthun (1992) Biochemistry 31:1579; Hollinger et al., 1993, supra, Gruber et al. (1994) J. Immunol.:5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

An "antigen binding fragment" of an intact antibody comprises one or more variable regions of an intact antibody. Examples of antibody fragments include Fab, Fab', F(ab')2 and Fv fragments; diabodies; linear antibodies; single-chain antibody molecules and multispecific antibodies formed from antibody fragments. For example, the term antigen binding fragment may be used to refer to recombinant single chain Fv fragments (scFv) as well as divalent (di-scFv) and trivalent (tri-scFV) forms thereof. Such fragments can be produced via various methods known in the art. For example, di-scFv encompassed by the present disclosure can be produced and purified by the methods described in Example 1 below.

The terms "full-length antibody", "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that specifically binds to an antigen and, for example, includes amino acid sequences of CDRs; i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region typically has three CDR regions identified as CDR1, CDR2 and CDR3. In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system" or "Kabat".

Other conventions that include corrections or alternate numbering systems for variable domains include IMGT (Lefranc, et al. (2003), Dev Comp Immunol 27: 55-77), Chothia (Chothia C, Lesk A M (1987), J Mal Biol 196: 901-917; Chothia, et al. (1989), Nature 342: 877-883) and AHo (Honegger A, Plückthun A (2001) J Mol Biol 309: 657-670). For convenience, examples of binding proteins of the present disclosure may also be labelled according to IMGT. These examples are expressly indicated as such. For example, see SEQ ID NO: 9-16.

"Framework regions" (Syn. FR) are those variable domain residues other than the CDR residues.

The term "constant region" as used herein, refers to a portion of heavy chain or light chain of an antibody other than the variable region. In a heavy chain, the constant region generally comprises a plurality of constant domains and a hinge region, e.g., a IgG constant region comprises the following linked components, a constant heavy $C_H1$, a linker, a $C_H2$ and a $C_H3$. In a heavy chain, a constant region comprises a Fc. In a light chain, a constant region generally comprise one constant domain (a CL1).

The term "fragment crystalizable" or "Fc" or "Fc region" or "Fc portion" (which can be used interchangeably herein) refers to a region of an antibody comprising at least one constant domain and which is generally (though not necessarily) glycosylated and which is capable of binding to one or more Fc receptors and/or components of the complement cascade. The heavy chain constant region can be selected from any of the five isotypes: α, δ, ε, γ, or μ. Exemplary heavy chain constant regions are gamma 1 (IgG1), gamma 2 (IgG2) and gamma 3 (IgG3), or hybrids thereof.

A "constant domain" is a domain in an antibody the sequence of which is highly similar in antibodies/antibodies of the same type, e.g., IgG or IgM or IgE. A constant region of an antibody generally comprises a plurality of constant domains, e.g., the constant region of γ, α or δ heavy chain comprises two constant domains.

The term "naked" is used to refer to binding proteins of the present disclosure that are not conjugated to another compound, e.g., a toxic compound or radiolabel. For example, the term "naked" can be used to refer to binding proteins such as di-scFv that are not conjugated to another compound. Accordingly, in one example, the binding proteins of the present disclosure are "naked". Put another way, the binding proteins of the present disclosure can be unconjugated.

In contrast, the term "conjugated" is used in the context of the present disclosure to refer to binding proteins of the present disclosure that are conjugated to another compound, e.g., a toxic compound such as a cytotoxic agent or radiolabel. Accordingly, in one example, the binding proteins of the present disclosure are "conjugated".

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, Bi, P, Pb and radioactive isotopes of Lu), chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

Terms such as "host cell," "host cell line," and "host cell culture" are used interchangeably in the context of the present disclosure to refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

An "isolated nucleic acid" according to the present disclosure is a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill of those practicing in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the term "binds" in reference to the interaction of a binding protein and an antigen means that the interaction is dependent upon the presence of a particular structure (e.g., an antigenic determinant or epitope) on the antigen. For example, a binding protein recognizes and binds to a specific antigen structure rather than to antigens generally. For example, if a binding protein binds to epitope "A", the presence of a molecule containing epitope "A" (or free, unlabeled "A"), in a reaction containing labeled "A" and the binding protein, will reduce the amount of labeled "A" bound to the binding protein.

As used herein, the term "specifically binds" shall be taken to mean that the binding interaction between a binding protein and DNA is dependent on detection of the DNA by the binding protein. Accordingly, the binding protein preferentially binds or recognizes DNA even when present in a mixture of other molecules or organisms.

In one example, the binding protein reacts or associates more frequently, more rapidly, with greater duration and/or with greater affinity with DNA than it does with alternative antigens or cells. It is also understood by reading this definition that, for example, a binding protein specifically binds to DNA may or may not specifically bind to a second antigen. As such, "specific binding" does not necessarily require exclusive binding or non-detectable binding of another antigen. The term "specifically binds" can be used interchangeably with "selectively binds" herein. Generally, reference herein to binding means specific binding, and each term shall be understood to provide explicit support for the other term. Methods for determining specific binding will be apparent to the skilled person. For example, a binding protein of the disclosure is contacted with DNA or an alternative antigen. Binding of the binding protein to DNA or alternative antigen is then determined and a binding protein that binds as set out above to the DNA rather than the alternative antigen is considered to specifically bind to DNA.

Binding proteins according to the present disclosure and compositions comprising the same can be administered to a subject to treat various indications. Terms such as "subject", "patient" or "individual" are terms that can, in context, be used interchangeably in the present disclosure. In an example, the subject is a mammal. The mammal may be a companion animal such as a dog or cat, or a livestock animal such as a horse or cow. In one example, the subject is a human. For example, the subject can be an adult. In another example, the subject can be a child. In another example, the subject can be an adolescent.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease are mitigated or eliminated.

As used herein, the term "prevention" includes providing prophylaxis with respect to occurrence or recurrence of a disease in an individual. An individual may be predisposed to or at risk of developing the disease or disease relapse but has not yet been diagnosed with the disease or the relapse.

The term "treatment" is used in the context of the present specification to refer to the medical management of a patient with the intent to cure, ameliorate or stabilize a disease, pathological condition, or disorder. The term "treatment" includes active treatment, that is, treatment directed specifically toward the improvement of a disease, pathological condition, or disorder, and also includes causal treatment, that is, treatment directed toward removal of the cause of the associated disease, pathological condition, or disorder. In addition, the term "treatment" includes palliative treatment, that is, treatment designed for the relief of symptoms rather than the curing of the disease, pathological condition, or disorder; prophylactic treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is meant an amount necessary to effect treatment of a disease or condition described below. The effective amount may vary according to the disease or condition to be treated and also according to the weight, age, racial background, sex, health and/or physical condition and other factors relevant to the subject being treated. Typically, the effective amount will fall within a relatively broad range (e.g. a "dosage" range) that can be determined through routine trial and experimentation by a medical practitioner. The effective amount can be administered in a single dose or in a dose repeated once or several times over a treatment period.

A "therapeutically effective amount" is at least the minimum concentration required to effect a measurable improvement of a particular disorder (e.g. cancer). A therapeutically effective amount herein may vary according to factors such as the disease state, age, sex, and weight of the patient, and the ability of the binding protein to elicit a desired response in the individual. A therapeutically effective amount is also one in which any toxic or detrimental effects of the binding protein are outweighed by the therapeutically beneficial effects. In the case of cancer, the therapeutically effective amount of the binding protein may reduce the number of cancer cells; reduce the primary tumor size; inhibit (i.e., slow to some extent and, in some examples, stop) cancer cell infiltration into peripheral organs; inhibit (i.e., slow to some extent and, in some examples, stop) tumor metastasis; inhibit or delay, to some extent, tumor growth or tumor progression; and/or relieve to some extent one or more of the symptoms associated with the cancer. To the extent the binding protein may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

Deimmunized, Chimeric, Humanized, Synhumanized, Primatized and Human Antibodies or Antigen Binding Fragments Monoclonal antibodies are one exemplary form of binding protein contemplated by the present disclosure. The term "monoclonal antibody" or "MAb" refers to a homogeneous antibody population capable of binding to the same antigen(s), for example, to the same epitope within the antigen. This term is not intended to be limited as regards to the source of the antibody or the manner in which it is made.

In an example, binding proteins encompassed by the present disclosure may be "humanized". A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. In an example, the humanized antibody will also comprise at least a portion of an immunoglobulin constant region (Fc), typically that of a human immunoglobulin (Jones et al., Nature 321:522-525 (1986); Riechmann et al., Nature 332:323-329 (1988); and Presta, Curr. Op. Struct. Biol. 2:593-596 (1992)).

In an example, "human" binding proteins of the present disclosure can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies.

In another example, binding proteins encompassed by the present disclosure may be synhumanized. The term "synhumanized" refers to an antibody prepared by a method described in WO2007/019620. A synhumanized antibody includes a variable region of an antibody, wherein the variable region comprises FRs from a New World primate antibody variable region and CDRs from a non-New World primate antibody variable region.

In another example, a binding protein of the present disclosure may be primatized. A "primatized antibody" comprises variable region(s) from an antibody generated following immunization of a non-human primate (e.g., a cynomolgus macaque). In an example, the variable regions of the non-human primate antibody are linked to human constant regions to produce a primatized antibody. Exemplary methods for producing primatized antibodies are described in U.S. Pat. No. 6,113,898.

In one example, a binding protein of the disclosure is a chimeric antibody or fragment. The term "chimeric antibody" or "chimeric antigen binding fragment" refers to an antibody or fragment in which one or more of the variable domains is from a particular species (e.g., murine, such as mouse or rat) or belonging to a particular antibody class or subclass, while the remainder of the antibody or fragment is from another species (such as, for example, human or non-human primate) or belonging to another antibody class or subclass. In one example, a chimeric antibody comprising a $V_H$ and/or a $V_L$ from a non-human antibody (e.g., a murine antibody) and the remaining regions of the antibody are from a human antibody.

The present disclosure also contemplates a deimmunized antibody or antigen binding fragment thereof, e.g., as described in WO2000/34317 and WO2004/108158. De-immunized antibodies and fragments have one or more epitopes, e.g., B cell epitopes or T cell epitopes removed (i.e., mutated) to thereby reduce the likelihood that a subject will raise an immune response against the antibody or protein. For example, an antibody of the disclosure is analyzed to identify one or more B or T cell epitopes and one or more amino acid residues within the epitope is mutated to thereby reduce the immunogenicity of the antibody.

Antibody Fragments

Single-Domain Antibodies

In some examples, a binding protein of the disclosure is or comprises a single-domain antibody (which is used interchangeably with the term "domain antibody" or "dAb"). A single-domain antibody is a single polypeptide chain comprising all or a portion of the heavy chain variable domain of an antibody.

Single Chain Fv (scFv) Fragments

One of skill in the art will be aware that scFv's comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). Single-chain variable fragments lack the constant Fc region found in complete antibody molecules and therefore can have reduced immunogenicity. Exemplary linkers comprise in excess of 12 amino acid residues with $(Gly_4Ser)_3$ being one of the more favoured linkers for a scFv. Another example of a suitable linker is provided in SEQ ID NO: 31.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

In another example, the present disclosure encompasses a dimeric scFv (di-scFV), i.e., a protein comprising two scFv molecules linked by a non-covalent or covalent linkage, e.g., by a leucine zipper domain (e.g., derived from Fos or Jun) or trimeric scFV (tri-scFv). In another example, two scFv's are linked by a peptide linker of sufficient length to permit both scFv's to form and to bind to an antigen, e.g., as described in U.S. Published Application No. 20060263367.

Diabodies, Triabodies, Tetrabodies

In some examples, an antigen binding fragment of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$—X—$V_H$ or $V_H$—X—$V_L$, wherein X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fv's having different specificity).

Other Antibodies and Antibody Fragments

Other examples of binding proteins encompassed by the present disclosure include:

(i) "key and hole" bispecific proteins as described in U.S. Pat. No. 5,731,168;

(ii) heteroconjugate proteins, e.g., as described in U.S. Pat. No. 4,676,980;

(iii) heteroconjugate proteins produced using a chemical cross-linker, e.g., as described in U.S. Pat. No. 4,676,980; and (iv) $Fab_3$ (e.g., as described in EP19930302894).

Immunoglobulins and Immunoglobulin Fragments

An example of a binding protein of the present disclosure is a protein (e.g., an antibody mimetic) comprising a variable region of an immunoglobulin, such as a T cell receptor or a heavy chain immunoglobulin (e.g., an IgNAR, a camelid antibody).

V-Like Proteins

An example of a binding protein of the disclosure is a T-cell receptor. T cell receptors have two V-domains that combine into a structure similar to the Fv module of an antibody. Novotny et al., Proc Natl Acad Sci USA 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Affibodies

In a further example, a binding protein of the disclosure is an affibody. An affibody is a scaffold derived from the Z domain (antigen binding domain) of Protein A of *Staphylococcus aureus* which can be engineered to bind to antigen. The Z domain consists of a three-helical bundle of approximately 58 amino acids. Libraries have been generated by randomization of surface residues. For further details see EP1641818.

Avimers

In a further example, a binding protein of the disclosure is an Avimer. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see WO2002/088171.

Binding Proteins

In one example, anti-DNA binding proteins according to the present disclosure comprise a heavy chain variable region (V$_H$) having a CDR 1 as shown in SEQ ID NO: 1, a CDR2 as shown in SEQ ID NO: 2 or SEQ ID NO: 3 and a CDR3 as shown in SEQ ID NO: 4. For example, an anti-DNA binding protein can comprise a V$_H$ having a CDR1 as shown in SEQ ID NO: 1, a CDR2 as shown in SEQ ID NO: 2 and a CDR3 as shown in SEQ ID NO: 4. In another example, an anti-DNA binding protein can comprise a V$_H$ having a CDR1 as shown in SEQ ID NO: 1, a CDR2 as shown in SEQ ID NO: 3 and a CDR3 as shown in SEQ ID NO: 4.

In another example, the anti-DNA binding proteins comprise a light chain variable region (V$_L$) having a CDR1 as shown in SEQ ID NO: 5 or SEQ ID NO: 6, a CDR2 as shown in SEQ ID NO: 7 and a CDR3 as shown in SEQ ID NO: 8. For example, an anti-DNA binding protein can comprise a V$_L$ having a CDR1 as shown in SEQ ID NO: 5, a CDR2 as shown in SEQ ID NO: 7 and a CDR3 as shown in SEQ ID NO: 8. In another example, an anti-DNA binding protein can comprise a V$_L$ having a CDR1 as shown in SEQ ID NO: 6, a CDR2 as shown in SEQ ID NO: 7 and a CDR3 as shown in SEQ ID NO: 8.

In another example, the anti-DNA binding proteins comprise a V$_H$ having a CDR1 as shown in SEQ ID NO: 1, a CDR2 as shown in SEQ ID NO: 2 or SEQ ID NO: 3 and a CDR3 as shown in SEQ ID NO: 4 and a V$_L$ having a CDR1 as shown in SEQ ID NO: 5 or SEQ ID NO: 6, a CDR2 as shown in SEQ ID NO: 7 and a CDR3 as shown in SEQ ID NO: 8. For example, an anti-DNA binding protein can comprise a V$_H$ having a CDR1 as shown in SEQ ID NO: 1, a CDR2 as shown in SEQ ID NO: 2 and a CDR3 as shown in SEQ ID NO: 4 and a V$_L$ having a CDR1 as shown in SEQ ID NO: 5, a CDR2 as shown in SEQ ID NO: 7 and a CDR3 as shown in SEQ ID NO: 8. In another example, an anti-DNA binding protein can comprise a V$_H$ having a CDR1 as shown in SEQ ID NO: 1, a CDR2 as shown in SEQ ID NO: 2 and a CDR3 as shown in SEQ ID NO: 4 and a V$_L$ having a CDR1 as shown in SEQ ID NO: 6, a CDR2 as shown in SEQ ID NO: 7 and a CDR3 as shown in SEQ ID NO: 8. In another example, an anti-DNA binding protein can comprise a V$_H$ having a CDR1 as shown in SEQ ID NO: 1, a CDR2 as shown in SEQ ID NO: 3 and a CDR3 as shown in SEQ ID NO: 4 and a V$_L$ having a CDR1 as shown in SEQ ID NO: 5, a CDR2 as shown in SEQ ID NO: 7 and a CDR3 as shown in SEQ ID NO: 8. In another example, an anti-DNA binding protein can comprise a V$_H$ having a CDR1 as shown in SEQ ID NO: 1, a CDR2 as shown in SEQ ID NO: 3 and a CDR3 as shown in SEQ ID NO: 4 and a V$_L$ having a CDR1 as shown in SEQ ID NO: 6, a CDR2 as shown in SEQ ID NO: 7 and a CDR3 as shown in SEQ ID NO: 8.

Above exemplified binding proteins may also have CDRs assigned using the IMGT system. Accordingly, in another example, the anti-DNA binding protein comprises a V$_H$ having a CDR1 as shown in SEQ ID NO: 9, a CDR2 as shown in SEQ ID NO: 10 or SEQ ID NO: 11 and a CDR3 as shown in SEQ ID NO: 12. For example, an anti-DNA binding protein can comprise a V$_H$ having a CDR1 as shown in SEQ ID NO: 9, a CDR2 as shown in SEQ ID NO: 10 and a CDR3 as shown in SEQ ID NO: 12. In another example, an anti-DNA binding protein can comprise a V$_H$ having a CDR1 as shown in SEQ ID NO: 9, a CDR2 as shown in SEQ ID NO: 11 and a CDR3 as shown in SEQ ID NO: 12.

In another example, the anti-DNA binding protein comprises a V$_L$ having a CDR1 as shown in SEQ ID NO: 13 or SEQ ID NO: 14, a CDR2 as shown in SEQ ID NO: 15 and a CDR3 as shown in SEQ ID NO: 16. For example, an anti-DNA binding protein can comprise a V$_L$ having a CDR1 as shown in SEQ ID NO: 13, a CDR2 as shown in SEQ ID NO: 15 and a CDR3 as shown in SEQ ID NO: 16. In another example, an anti-DNA binding protein can comprise a V$_L$ having a CDR1 as shown in SEQ ID NO: 14, a CDR2 as shown in SEQ ID NO: 15 and a CDR3 as shown in SEQ ID NO: 16.

In another example, the anti-DNA binding proteins comprises a V$_H$ having a CDR1 as shown in SEQ ID NO: 9, a CDR2 as shown in SEQ ID NO: 10 or SEQ ID NO: 11 and a CDR3 as shown in SEQ ID NO: 12 and a V$_L$ having a CDR1 as shown in SEQ ID NO: 13 or SEQ ID NO: 14, a CDR2 as shown in SEQ ID NO: 15 and a CDR3 as shown in SEQ ID NO: 16. For example, an anti-DNA binding protein can comprise a V$_H$ having a CDR1 as shown in SEQ ID NO: 9, a CDR2 as shown in SEQ ID NO: 10 and a CDR3 as shown in SEQ ID NO: 12 and a V$_L$ having a CDR1 as shown in SEQ ID NO: 13, a CDR2 as shown in SEQ ID NO: 15 and a CDR3 as shown in SEQ ID NO: 16. In another example, an anti-DNA binding protein can comprise a V$_H$ having a CDR1 as shown in SEQ ID NO: 9, a CDR2 as shown in SEQ ID NO: 10 and a CDR3 as shown in SEQ ID NO: 12 and a V$_L$ having a CDR1 as shown in SEQ ID NO: 14, a CDR2 as shown in SEQ ID NO: 15 and a CDR3 as shown in SEQ ID NO: 16. In another example, an anti-DNA binding protein can comprise a V$_H$ having a CDR1 as shown in SEQ ID NO: 9, a CDR2 as shown in SEQ ID NO: 11 and a CDR3 as shown in SEQ ID NO: 12 and a V$_L$ having a CDR1 as shown in SEQ ID NO: 13, a CDR2 as shown in SEQ ID NO: 15 and a CDR3 as shown in SEQ ID NO: 16. In another example, an anti-DNA binding protein can comprise a V$_H$ having a CDR1 as shown in SEQ ID NO: 9, a CDR2 as shown in SEQ ID NO: 11 and a CDR3 as shown in SEQ ID NO: 12 and a V$_L$ having a CDR1 as shown in SEQ ID NO: 14, a CDR2 as shown in SEQ ID NO: 15 and a CDR3 as shown in SEQ ID NO: 16.

In another example, the anti-DNA binding proteins comprise a V$_H$ comprising a sequence at least 95% identical to the sequence as shown in any one of SEQ ID NOs: 17 to 23. For example, an anti-DNA binding protein can comprise a V$_H$ comprising a sequence at least 95% identical to the sequence as shown in SEQ ID NO: 18. In another example, an anti-DNA binding protein can comprise a V$_{11}$ comprising a sequence at least 95% identical to the sequence as shown in SEQ ID NO: 23. In another example, the anti-DNA binding proteins comprise a V$_L$ comprising a sequence at least 95% identical to the sequence as shown in any one of SEQ ID NOs: 24 to 29. For example, an anti-DNA binding protein can comprise a V$_L$ comprising a sequence at least 95% identical to the sequence as shown in SEQ ID NO: 25. In another example, an anti-DNA binding protein can comprise a V$_L$ comprising a sequence at least 95% identical to the sequence as shown in SEQ ID NO: 27. In another example, the anti-DNA binding proteins comprise a V$_H$ comprising a sequence at least 95% identical to the sequence as shown in any one of SEQ ID NOs: 17 to 23 and a V$_L$ comprising a sequence at least 95% identical to the sequence as shown in any one of SEQ ID NOs: 24 to 29. For example, an anti-DNA binding protein can comprise a V$_H$ comprising a sequence at least 95% identical to the sequence as shown in SEQ ID NO: 18 and a V$_L$ comprising a sequence at least 95% identical to the sequence as shown in SEQ ID NO: 25. In another example, an anti-DNA binding protein can comprise a V$_H$ comprising a sequence at least 95% identical to the sequence as shown in SEQ ID NO: 23 and a V$_L$ comprising a sequence at least 95% identical to the sequence as shown in SEQ ID NO: 27. In these examples, the V$_H$ and/or $V_L$ can be at least 96%, at least 97%, at least 98% or at least 99% identical to the recited SEQ ID NO.

In another example, the anti-DNA binding proteins comprise a $V_H$ comprising a sequence as shown in any one of SEQ ID NOs: 17 to 23. For example, an anti-DNA binding protein can comprise a $V_H$ comprising a sequence as shown in SEQ ID NO: 18. In another example, an anti-DNA binding protein can comprise a $V_H$ comprising a sequence as shown in SEQ ID NO: 23. In another example, the anti-DNA binding proteins comprise a $V_L$ comprising a sequence as shown in any one of SEQ ID NOs: 24 to 29. For example, an anti-DNA binding protein can comprise a $V_L$ comprising a sequence as shown in SEQ ID NO: 25. In another example, an anti-DNA binding protein can comprise a $V_L$ comprising a sequence as shown in SEQ ID NO: 27. In another example, the anti-DNA binding proteins comprise a $V_H$ comprising a sequence as shown in any one of SEQ ID NOs: 17 to 23 and a $V_L$ comprising a sequence as shown in any one of SEQ ID NOs: 24 to 29. For example, an anti-DNA binding protein can comprise a $V_H$ comprising a sequence as shown in SEQ ID NO: 18 and a $V_L$ comprising a sequence as shown in SEQ ID NO: 25. In another example, an anti-DNA binding protein can comprise a $V_H$ comprising a sequence as shown in SEQ ID NO: 23 and a $V_L$ comprising a sequence as shown in SEQ ID NO: 27.

In an example, the anti-DNA binding protein can be a cell penetrating anti-DNA Fv fragment having an antigen binding domain, wherein the antigen binding domain binds to or specifically binds to DNA. For example, the Fv can bind the same epitope as a binding protein having a $V_H$ comprising an amino acid sequence as shown in SEQ ID NO: 48 and a $V_L$ comprising an amino acid sequence as shown in SEQ ID NO: 49. In another example, the Fv can bind the same epitope as a di-scFv having an amino acid sequence as shown in SEQ ID NO: 50. In an example, the Fv comprises a $V_H$ having a CDR1 as shown in SEQ ID NO: 1, a CDR2 as shown in SEQ ID NO: 2 or SEQ ID NO: 3 and a CDR3 as shown in SEQ ID NO: 4. For example, an Fv can comprise a $V_H$ having a CDR1 as shown in SEQ ID NO: 1, a CDR2 as shown in SEQ ID NO: 2 and a CDR3 as shown in SEQ ID NO: 4. In another example, an Fv can comprise a $V_H$ having a CDR1 as shown in SEQ ID NO: 1, a CDR2 as shown in SEQ ID NO: 3 and a CDR3 as shown in SEQ ID NO: 4.

In another example, the Fv comprises a $V_L$ having a CDR1 as shown in SEQ ID NO: 5 or SEQ ID NO: 6, a CDR2 as shown in SEQ ID NO: 7 and a CDR3 as shown in SEQ ID NO: 8. For example, an Fv can comprise a $V_L$ having a CDR1 as shown in SEQ ID NO: 5, a CDR2 as shown in SEQ ID NO: 7 and a CDR3 as shown in SEQ ID NO: 8. In another example, an anti-DNA binding protein can comprise a $V_L$ having a CDR1 as shown in SEQ ID NO: 6, a CDR2 as shown in SEQ ID NO: 7 and a CDR3 as shown in SEQ ID NO: 8.

In another example, the Fv comprises a $V_H$ having a CDR1 as shown in SEQ ID NO: 1, a CDR2 as shown in SEQ ID NO: 2 or SEQ ID NO: 3 and a CDR3 as shown in SEQ ID NO: 4 and a $V_L$ having a CDR1 as shown in SEQ ID NO: 5 or SEQ ID NO: 6, a CDR2 as shown in SEQ ID NO: 7 and a CDR3 as shown in SEQ ID NO: 8. For example, an Fv can comprise a $V_H$ having a CDR1 as shown in SEQ ID NO: 1, a CDR2 as shown in SEQ ID NO: 2 and a CDR3 as shown in SEQ ID NO: 4 and a $V_L$ having a CDR1 as shown in SEQ ID NO: 5, a CDR2 as shown in SEQ ID NO: 7 and a CDR3 as shown in SEQ ID NO: 8. In another example, an Fv can comprise a $V_H$ having a CDR1 as shown in SEQ ID NO: 1, a CDR2 as shown in SEQ ID NO: 3 and a CDR3 as shown in SEQ ID NO: 4 and a $V_L$ having a CDR1 as shown in SEQ ID NO: 5, a CDR2 as shown in SEQ ID NO: 7 and a CDR3 as shown in SEQ ID NO: 8. In another example, an Fv can comprise a $V_H$ having a CDR1 as shown in SEQ ID NO: 1, a CDR2 as shown in SEQ ID NO: 2 and a CDR3 as shown in SEQ ID NO: 4 and a $V_L$ having a CDR1 as shown in SEQ ID NO: 6, a CDR2 as shown in SEQ ID NO: 7 and a CDR3 as shown in SEQ ID NO: 8. In another example, an Fv can comprise a $V_H$ having a CDR1 as shown in SEQ ID NO: 1, a CDR2 as shown in SEQ ID NO: 3 and a CDR3 as shown in SEQ ID NO: 4 and a $V_L$ having a CDR1 as shown in SEQ ID NO: 6, a CDR2 as shown in SEQ ID NO: 7 and a CDR3 as shown in SEQ ID NO: 8.

Above exemplified Fv may also have CDRs assigned using the IMGT system. Accordingly, in another example, the Fv comprises a $V_H$ having a CDR1 as shown in SEQ ID NO: 9, a CDR2 as shown in SEQ ID NO: 10 or SEQ ID NO: 11 and a CDR3 as shown in SEQ ID NO: 12. For example, an Fv can comprise a $V_H$ having a CDR1 as shown in SEQ ID NO: 9, a CDR2 as shown in SEQ ID NO: 10 and a CDR3 as shown in SEQ ID NO: 12. In another example, an Fv can comprise a $V_H$ having a CDR1 as shown in SEQ ID NO: 9, a CDR2 as shown in SEQ ID NO: 11 and a CDR3 as shown in SEQ ID NO: 12.

In another example, the Fv comprises a $V_L$ having a CDR1 as shown in SEQ ID NO: 13 or SEQ ID NO: 14, a CDR2 as shown in SEQ ID NO: 15 and a CDR3 as shown in SEQ ID NO: 16. For example, an Fv can comprise a $V_L$ having a CDR1 as shown in SEQ ID NO: 13, a CDR2 as shown in SEQ ID NO: 15 and a CDR3 as shown in SEQ ID NO: 16. In another example, an Fv can comprise a $V_L$ having a CDR1 as shown in SEQ ID NO: 14, a CDR2 as shown in SEQ ID NO: 15 and a CDR3 as shown in SEQ ID NO: 16.

In another example, the Fv comprises a $V_H$ having a CDR1 as shown in SEQ ID NO: 9, a CDR2 as shown in SEQ ID NO: 10 or SEQ ID NO: 11 and a CDR3 as shown in SEQ ID NO: 12 and a $V_L$ having a CDR1 as shown in SEQ ID NO: 13 or SEQ ID NO: 14, a CDR2 as shown in SEQ ID NO: 15 and a CDR3 as shown in SEQ ID NO: 16. For example, an Fv can comprise a $V_H$ having a CDR1 as shown in SEQ ID NO: 9, a CDR2 as shown in SEQ ID NO: 10 and a CDR3 as shown in SEQ ID NO: 12 and a $V_L$ having a CDR1 as shown in SEQ ID NO: 13, a CDR2 as shown in SEQ ID NO: 15 and a CDR3 as shown in SEQ ID NO: 16. In another example, an Fv can comprise a $V_H$ having a CDR1 as shown in SEQ ID NO: 9, a CDR2 as shown in SEQ ID NO: 10 and a CDR3 as shown in SEQ ID NO: 12 and a $V_L$ having a CDR1 as shown in SEQ ID NO: 14, a CDR2 as shown in SEQ ID NO: 15 and a CDR3 as shown in SEQ ID NO: 16. In another example, an Fv can comprise a $V_H$ having a CDR1 as shown in SEQ ID NO: 9, a CDR2 as shown in SEQ ID NO: 11 and a CDR3 as shown in SEQ ID NO: 12 and a $V_L$ having a CDR1 as shown in SEQ ID NO: 13, a CDR2 as shown in SEQ ID NO: 15 and a CDR3 as shown in SEQ ID NO: 16. In another example, an Fv can comprise a $V_H$ having a CDR1 as shown in SEQ ID NO: 9, a CDR2 as shown in SEQ ID NO: 11 and a CDR3 as shown in SEQ ID NO: 12 and a $V_L$ having a CDR1 as shown in SEQ ID NO: 14, a CDR2 as shown in SEQ ID NO: 15 and a CDR3 as shown in SEQ ID NO: 16.

In another example, the Fv comprises a $V_H$ comprising a sequence at least 95% identical to the sequence as shown in any one of SEQ ID NOs: 17 to 23. For example, an Fv can comprise a $V_H$ comprising a sequence at least 95% identical to the sequence as shown in SEQ ID NO: 18. In another example, an Fv can comprise a $V_H$ comprising a sequence at least 95% identical to the sequence as shown in SEQ ID NO:

21. In another example, an Fv can comprise a $V_H$ comprising a sequence at least 95% identical to the sequence as shown in SEQ ID NO: 23. In another example, the Fv comprises a $V_L$ comprising a sequence at least 95% identical to the sequence as shown in any one of SEQ ID NOs: 24 to 29. For example, an Fv can comprise a $V_L$ comprising a sequence at least 95% identical to the sequence as shown in SEQ ID NO: 25. In another example, an Fv can comprise a $V_L$ comprising a sequence at least 95% identical to the sequence as shown in SEQ ID NO: 27. In another example, the Fv comprises a $V_H$ comprising a sequence at least 95% identical to the sequence as shown in any one of SEQ ID NOs: 17 to 23 and a $V_L$ comprising a sequence at least 95% identical to the sequence as shown in any one of SEQ ID NOs: 24 to 29. For example, an Fv can comprise a $V_H$ comprising a sequence at least 95% identical to the sequence as shown in SEQ ID NO: 18 and a $V_L$ comprising a sequence at least 95% identical to the sequence as shown in SEQ ID NO: 25. In another example, an Fv can comprise a $V_H$ comprising a sequence at least 95% identical to the sequence as shown in SEQ ID NO: 21 and a $V_L$ comprising a sequence at least 95% identical to the sequence as shown in SEQ ID NO: 27. In another example, an Fv can comprise a $V_H$ comprising a sequence at least 95% identical to the sequence as shown in SEQ ID NO: 23 and a $V_L$ comprising a sequence at least 95% identical to the sequence as shown in SEQ ID NO: 27. In these examples, the $V_H$ and/or $V_L$ can be at least 96%, at least 97%, at least 98% or at least 99% identical to the recited SEQ ID NO. In these examples, the Fv can have an above referenced combination of CDRs. For example, an Fv can comprise a $V_H$ comprising a sequence at least 95% identical to the sequence as shown in SEQ ID NO: 21 and a $V_L$ comprising a sequence at least 95% identical to the sequence as shown in SEQ ID NO: 27, wherein the $V_H$ has a CDR1 as shown in SEQ ID NO: 1, a CDR2 as shown in SEQ ID NO: 3 and a CDR3 as shown in SEQ ID NO: 4 and the $V_L$ has a CDR1 as shown in SEQ ID NO: 6, a CDR2 as shown in SEQ ID NO: 7 and a CDR3 as shown in SEQ ID NO: 8.

In another example, the Fv comprises a $V_H$ comprising a sequence as shown in any one of SEQ ID NOs: 17 to 23. For example, an Fv can comprise a $V_H$ comprising a sequence as shown in SEQ ID NO: 18. In another example, an Fv can comprise a $V_H$ comprising a sequence as shown in SEQ ID NO: 21. In another example, an Fv can comprise a $V_H$ comprising a sequence as shown in SEQ ID NO: 23. In another example, the Fv comprises a $V_L$ comprising a sequence as shown in any one of SEQ ID NOs: 24 to 29. For example, an Fv can comprise a $V_L$ comprising a sequence as shown in SEQ ID NO: 25. In another example, an Fv can comprise a $V_L$ comprising a sequence as shown in SEQ ID NO: 27. In another example, the Fv comprises a $V_H$ comprising a sequence as shown in any one of SEQ ID NOs: 17 to 23 and a $V_L$ comprising a sequence as shown in any one of SEQ ID NOs: 24 to 29. For example, an Fv can comprise a $V_H$ comprising a sequence as shown in SEQ ID NO: 18 and a $V_L$ comprising a sequence as shown in SEQ ID NO: 25. In another example, an Fv can comprise a $V_H$ comprising a sequence as shown in SEQ ID NO: 21 and a $V_L$ comprising a sequence as shown in SEQ ID NO: 27. In another example, an Fv can comprise a $V_H$ comprising a sequence as shown in SEQ ID NO: 23 and a $V_L$ comprising a sequence as shown in SEQ ID NO: 27.

In another example, the Fv has improved manufacturability compared to a binding protein having a $V_H$ comprising an amino acid sequence as shown in SEQ ID NO: 48 and a $V_L$ comprising an amino acid sequence as shown in SEQ ID NO: 49. In another example, the Fv has improved manufacturability compared to a di-scFv having an amino acid sequence as shown in SEQ ID NO: 50.

Improved manufacturability encompasses post translational modifications or increased chemical stability relating to reduced numbers of deamidation sites, aspartate isomerization sites, oxidation sites such as methionine and tryptophan, free-cysteine thiol groups, N & O-glycosylation sites, the presence of C-terminal lysine and/or isoelectric point.

In an example, the Fv comprises less asparagine in the $V_H$ and/or $V_L$ compared with a binding protein having a $V_H$ comprising an amino acid sequence as shown in SEQ ID NO: 48 and a $V_L$ comprising an amino acid sequence as shown in SEQ ID NO: 49. In another example, the Fv comprises less asparagine in the $V_H$ and/or $V_L$ compared with a di-scFv having an amino acid sequence as shown in SEQ ID NO: 50.

In an example, the Fv comprises less methionine in the $V_H$ and/or $V_L$ compared with a binding protein having a $V_H$ comprising an amino acid sequence as shown in SEQ ID NO: 48 and a $V_L$ comprising an amino acid sequence as shown in SEQ ID NO: 49. In another example, the Fv comprises less methionine in the $V_H$ and/or $V_L$ compared with a di-scFv having an amino acid sequence as shown in SEQ ID NO: 50.

In an example, the Fv comprises less tryptophan in the $V_H$ and/or $V_L$ compared with a binding protein having a $V_H$ comprising an amino acid sequence as shown in SEQ ID NO: 48 and a $V_L$ comprising an amino acid sequence as shown in SEQ ID NO: 49. In another example, the Fv comprises less tryptophan in the $V_H$ and/or $V_L$ compared with a di-scFv having an amino acid sequence as shown in SEQ ID NO: 50.

In an example, the Fv comprises less aspartic acid in the $V_H$ and/or $V_L$ compared with a binding protein having a $V_H$ comprising an amino acid sequence as shown in SEQ ID NO: 48 and a $V_L$ comprising an amino acid sequence as shown in SEQ ID NO: 49. In another example, the Fv comprises less aspartic acid in the $V_H$ and/or $V_L$ compared with a di-scFv having an amino acid sequence as shown in SEQ ID NO: 50.

In an example, the physical stability of the Fv is greater than a binding protein having a $V_H$ comprising an amino acid sequence as shown in SEQ ID NO: 48 and a $V_L$ comprising an amino acid sequence as shown in SEQ ID NO: 49. In another example, the physical stability of the Fv is greater than a di-scFv having an amino acid sequence as shown in SEQ ID NO: 50.

Physical stability can include propensity for aggregation in solution. The term "aggregation" is used in the context of the present disclosure to refer to protein self-association, which can occur in multiple environments, from cell culture and fermentation, to isolation, purification and formulation processes. For example, the term "aggregation" can be used when describing the formation of inclusions; the accumulation of protein in "insoluble" fractions following cell fractionation; the appearance of turbidity, protein precipitation or formation of particles in samples; or the formation of small soluble oligomers amongst others.

Accordingly, in the above referenced examples, the physical stability of a Fv can be based on its physical stability in solution, wherein precipitation of the Fv from solution indicates that the Fv has become unstable. To assess physical stability, solutions comprising a Fv according to the present disclosure or either a binding protein having a $V_H$ comprising an amino acid sequence as shown in SEQ ID NO: 48 and a $V_L$ comprising an amino acid sequence as shown in SEQ ID NO: 49 or a di-scFv comprising an amino acid sequence as shown in SEQ ID NO: 50 can be incubated at 4° C. and assessed visually for precipitation at two weeks, four weeks, 12 weeks, six months and 12 months.

In an example, the physical stability of an Fv according to the present disclosure is greater than a binding protein having a $V_H$ comprising an amino acid sequence as shown in SEQ ID NO: 48 and a $V_L$ comprising an amino acid sequence as shown in SEQ ID NO: 49 or a di-scFv comprising an amino acid sequence as shown in SEQ ID NO: 50 when the Fv remains in solution at 4° C. for at least four weeks. In an example, the physical stability of an Fv according to the present disclosure is greater than a binding protein having a $V_H$ comprising an amino acid sequence as shown in SEQ ID NO: 48 and a $V_L$ comprising an amino acid sequence as shown in SEQ ID NO: 49 or a di-scFv comprising an amino acid sequence as shown in SEQ ID NO: 50 when the Fv remains in solution at 4° C. for at least six months.

In another example, the Fv has reduced immunogenicity in a human subject compared to a binding protein having a $V_H$ comprising an amino acid sequence as shown in SEQ ID NO: 48 and a $V_L$ comprising an amino acid sequence as shown in SEQ ID NO: 49. For example, an Fv can have reduced immunogenicity compared to a binding protein having a $V_H$ comprising an amino acid sequence as shown in SEQ ID NO: 48 and a $V_L$ comprising an amino acid sequence as shown in SEQ ID NO: 49 when immunogenicity is measure via enzyme-linked immunosorbent assay (ELISA). In another example, an Fv can have reduced immunogenicity compared to a binding protein having a $V_H$ comprising an amino acid sequence as shown in SEQ ID NO: 48 and a $V_L$ comprising an amino acid sequence as shown in SEQ ID NO: 49 when immunogenicity is measure via Surface Plasmon Resonance.

In another example, the capacity of the Fv to penetrate cells is greater than a binding protein having a $V_H$ comprising an amino acid sequence as shown in SEQ ID NO: 48 and a $V_L$ comprising an amino acid sequence as shown in SEQ ID NO: 49. In another example, the capacity of the Fv to penetrate cells is greater than a di-scFv having an amino acid sequence as shown in SEQ ID NO: 50. In another example, the capacity of the Fv to penetrate cell nuclei is greater than a binding protein having a $V_H$ comprising an amino acid sequence as shown in SEQ ID NO: 48 and a $V_L$ comprising an amino acid sequence as shown in SEQ ID NO: 49. In another example, the capacity of the Fv to penetrate cell nuclei is greater than a di-scFv having an amino acid sequence as shown in SEQ ID NO: 50. For example, the di-scFv can comprise an amino acid sequence as shown in SEQ ID NO: 36. In another example, the di-scFv can comprise an amino acid sequence as shown in SEQ ID NO: 41. In another example, the di-scFv can comprise an amino acid sequence as shown in SEQ ID NO: 43. In the above referenced examples, the capacity of a binding protein to penetrate cells or cell nuclei can be measured using a colorimetric assay. For example, cells can be treated with control media, a binding protein according to the present disclosure or either a binding protein having a $V_H$ comprising an amino acid sequence as shown in SEQ ID NO: 48 and a $V_L$ comprising an amino acid sequence as shown in SEQ ID NO: 49 or a di-scFv having an amino acid sequence as shown in SEQ ID NO: 50 for one hour. Cells are then washed, fixed, blocked with 1% BSA-TBST, and then probed with protein L for one hour. Cells are then washed and incubated with an anti-protein L primary antibody for one hour. After another round of washing, cells are incubated with an alkaline phosphatase-conjugated secondary antibody for one hour. Finally, cells are washed and signal is developed by addition of NBT/BCIP. Signal development is stopped by removal of NBT/BCIP and washing once distinct nuclear stain is identifiable in any of the samples. Nuclear and or cellular staining is then measured using Image J.

In an example, an Fv providing nuclear staining having reciprocal intensity of at least 190 absorbance units (au) has greater capacity to penetrate cell nuclei. In an example, an Fv providing nuclear staining having reciprocal intensity of at least 200 au has greater capacity to penetrate cell nuclei. In an example, an Fv providing nuclear staining having reciprocal intensity of at least 210 au has greater capacity to penetrate cell nuclei. In an example, an Fv providing nuclear staining having reciprocal intensity of at least 220 au has greater capacity to penetrate cell nuclei. In another example, the capacity of an Fv to penetrate cell nuclei can be assessed by measuring florescence in individual cells. In an example, an Fv providing nuclear staining having reciprocal intensity of at least 190 au in at least 20 cells has greater capacity to penetrate cell nuclei. In another example, an Fv providing nuclear staining having reciprocal intensity of at least 190 au in at least 30 cells has greater capacity to penetrate cell nuclei. In another example, an Fv providing nuclear staining having reciprocal intensity of at least 190 au in at least 40 cells has greater capacity to penetrate cell nuclei. In another example, an Fv providing nuclear staining having reciprocal intensity of at least 200 au in at least 20 cells has greater capacity to penetrate cell nuclei. In another example, an Fv providing nuclear staining having reciprocal intensity of at least 200 au in at least 30 cells has greater capacity to penetrate cell nuclei. In another example, an Fv providing nuclear staining having reciprocal intensity of at least 200 au in at least 50 cells has greater capacity to penetrate cell nuclei. In another example, an Fv providing nuclear staining having reciprocal intensity of at least 200 au in at least 70 cells has greater capacity to penetrate cell nuclei. In another example, an Fv providing nuclear staining having reciprocal intensity of at least 200 au in at least 80 cells has greater capacity to penetrate cell nuclei.

In another example, the Fv has higher specificity for DNA than a binding protein having a $V_H$ comprising an amino acid sequence as shown in SEQ ID NO: 48 and a $V_L$ comprising an amino acid sequence as shown in SEQ ID NO: 49. In another example, the Fv has higher specificity for DNA than a di-scFv having an amino acid sequence as shown in SEQ ID NO: 50.

In another example, the Fv has lower cross-reactivity (i.e. the ability of an Fv to react with similar antigenic sites on different proteins) compared to a binding protein having a Vu comprising an amino acid sequence as shown in SEQ ID NO: 48 and a $V_L$ comprising an amino acid sequence as shown in SEQ ID NO: 49. In another example, the Fv has lower cross-reactivity with other targets compared to a di-scFv having an amino acid sequence as shown in SEQ ID NO: 50. In this example, cross-reactivity of an Fv can be measured using various methods. In an example, cross-reactivity is assessed via ELISA.

In another example, the Fv has higher binding affinity for DNA than a binding protein having a $V_H$ comprising an amino acid sequence as shown in SEQ ID NO: 48 and a $V_L$ comprising an amino acid sequence as shown in SEQ ID NO: 49. In another example, the Fv has higher binding affinity for DNA than a di-scFv having an amino acid sequence as shown in SEQ ID NO: 50.

In the above referenced examples, the affinity of an Fv for DNA can be measured using various methods. In an example, the dissociation constant ($K_D$) or association constant ($K_A$) or equilibrium constant ($K_D$) of a binding protein for DNA is determined. These constants for a binding protein are, in one example, measured by a radiolabeled or fluorescently-labelled DNA-binding assay. This assay equilibrates the binding protein with a minimal concentration of labelled DNA (or a soluble form thereof, e.g., comprising an extracellular region of DNA fused to an Fc region) in the presence of a titration series of unlabelled DNA. Following washing to remove unbound DNA, the amount of label is determined.

Affinity measurements can be determined by standard methodology for antibody reactions, for example, immunoassays, surface plasmon resonance (SPR) (Rich and Myszka Curr. Opin. Biotechnol 11:54, 2000; Englebienne Analyst. 123: 1599, 1998), isothermal titration calorimetry (ITC) or other kinetic interaction assays known in the art.

In one example, the constants are measured by using surface plasmon resonance assays, e.g., using BIAcore surface plasmon resonance (BIAcore, Inc., Piscataway, N.J.) with immobilized DNA. Exemplary SPR methods are described in U.S. Pat. No. 7,229,619.

In some embodiments, the binding affinity for DNA of the Fv is between about 5 nM and about 100 pM, 10 pM, 1 pM, 100 fM, 10 fM, or 1 fM.

In an example, Fv encompassed by the present disclosure have a binding affinity for DNA comparable to about 5 nM or less, or about 4.9 nM, or about 4.8 nM, or about 4.7 nM, or about 4.6 nM, or about 4.7 nM, or about 4.6 nM, or about 4.5 nM, or about 4.4 nM, or about 4.3 nM, or about 4.2 nM, or about 4.1 nM, or about 4.0 nM, or about 3.9 nM, or about 3.8 nM, or about 3.7 nM, or about 3.6 nM, or about 3.5 nM, or about 3.4 nM, or about 3.3 nM, or about 3.2 nM, or about 3.1 nM, or about 3.0 nM.

In other examples, subject Fv can have a binding affinity for DNA comparable to about 100 pM, or about 150 pM, or about 200 pM, or about 250 pM, or about 300 pM, or about 350 pM, or about 400 pM, or about 450 pM, or about 466 pM as measured by surface plasmon resonance (e.g. using a BIAcore 3000 instrument).

In the other examples, the affinity of a binding protein for DNA can be measured using Isothermal Titration Microcalorimetry.

In an example, the Fv comprises a linker. Various suitable linkers and methods for their design have been described previously (e.g. U.S. Pat. No. 4,946,778; WO 1994/012520; and U.S. Pat. No. 4,704,692). In an example, the Fv comprises a glycine-serine (GS) linker. For example, the GS linker can comprise (GGGGS)₃ (SEQ ID NO: 67). In an example, the Fv comprises a linker having the sequence shown in SEQ ID NO: 30. In another example, the Fv comprises a linker having the sequence shown in SEQ ID NO: 31. In another example, the Fv comprises linkers having the sequences shown in SEQ ID NO: 30 and SEQ ID NO: 31.

In an example, the $V_H$ and $V_L$ of the Fv can be in a single polypeptide chain. In another example, the Fv lacks an Fc region. For example, the Fv can be a single chain Fv fragment (scFv), a dimeric scFv (di-scFv), a trimeric scFv (tri-scFv). In an example, the Fv is an scFv. In another example, the Fv is a di-scFv. In another example, the Fv is a tri-scFv.

In another example, the scFv, di-scFv or tri-scFv can be linked to a constant region of an antibody, Fc or a heavy chain constant domain $C_H2$ and/or $C_H3$.

In an example, the present disclosure encompasses a cell penetrating di-scFv having an antigen binding domain, wherein the antigen binding domain binds to or specifically binds to DNA.

In an example, a di-scFv according to the present disclosure comprises an amino acid sequence at least 95% identical to the sequence as shown in any one of SEQ ID NOs: 32 to 47. In an example, the di-scFv comprises an amino acid sequence at least 95% identical to the sequence shown in SEQ ID NO: 32. In an example, the di-scFv comprises an amino acid sequence at least 95% identical to the sequence shown in SEQ ID NO: 33. In an example, the di-scFv comprises an amino acid sequence at least 95% identical to the sequence shown in SEQ ID NO: 34. In an example, the di-scFv comprises an amino acid sequence at least 95% identical to the sequence shown in SEQ ID NO: 35. In an example, the di-scFv comprises an amino acid sequence at least 95% identical to the sequence shown in SEQ ID NO: 36. In an example, the di-scFv comprises an amino acid sequence at least 95% identical to the sequence shown in SEQ ID NO: 37. In an example, the di-scFv comprises an amino acid sequence at least 95% identical to the sequence shown in SEQ ID NO: 38. In an example, the di-scFv comprises an amino acid sequence at least 95% identical to the sequence shown in SEQ ID NO: 39. In an example, the di-scFv comprises an amino acid sequence at least 95% identical to the sequence shown in SEQ ID NO: 40. In an example, the di-scFv comprises an amino acid sequence at least 95% identical to the sequence shown in SEQ ID NO: 41. In an example, the di-scFv comprises an amino acid sequence at least 95% identical to the sequence shown in SEQ ID NO: 42. In an example, the di-scFv comprises an amino acid sequence at least 95% identical to the sequence shown in SEQ ID NO: 43. In an example, the di-scFv comprises an amino acid sequence at least 95% identical to the sequence shown in SEQ ID NO: 44. In an example, the di-scFv comprises an amino acid sequence at least 95% identical to the sequence shown in SEQ ID NO: 45. In an example, the di-scFv comprises an amino acid sequence at least 95% identical to the sequence shown in SEQ ID NO: 46. In an example, the di-scFv comprises an amino acid sequence at least 95% identical to the sequence shown in SEQ ID NO: 47. For example, the di-scFv comprises an amino acid sequence at least 95% identical to the amino acid sequence shown in any one of SEQ ID NOs: 32, 36, 41 or 43. In these examples, amino acid sequences can be at least 96%, at least 97%, at least 98% or at least 99% identical to the recited SEQ ID NO.

In an example, a di-scFv according to the present disclosure comprises an amino acid sequence as shown in any one of SEQ ID NOs: 32 to 47. In an example, the di-scFv comprises an amino acid sequence as shown in SEQ ID NO: 32. In an example, the di-scFv comprises an amino acid sequence as shown in SEQ ID NO: 33. In an example, the di-scFv comprises an amino acid sequence as shown in SEQ ID NO: 34. In an example, the di-scFv comprises an amino acid sequence as shown in SEQ ID NO: 35. In an example, the di-scFv comprises an amino acid sequence as shown in SEQ ID NO: 36. In an example, the di-scFv comprises an amino acid sequence as shown in SEQ ID NO: 37. In an example, the di-scFv comprises an amino acid sequence as shown in SEQ ID NO: 38. In an example, the di-scFv comprises an amino acid sequence as shown in SEQ ID NO: 39. In an example, the di-scFv comprises an amino acid sequence as shown in SEQ ID NO: 40. In an example, the di-scFv comprises an amino acid sequence as shown in SEQ ID NO: 41. In an example, the di-scFv comprises an amino acid sequence as shown in SEQ ID NO: 42. In an example, the di-scFv comprises an amino acid sequence as shown in SEQ ID NO: 43. In an example, the di-scFv comprises an amino acid sequence as shown in SEQ ID NO: 44. In an example, the di-scFv comprises an amino acid sequence as shown in SEQ ID NO: 45. In an example, the di-scFv comprises an amino acid sequence as shown in SEQ ID NO: 46. In an example, the di-scFv comprises an amino acid sequence as shown in SEQ ID NO: 47. For example, the di-scFv can comprise an amino acid sequence as shown in any one of SEQ ID NOs: 32, 36, 41 and 43.

In another example, the $V_H$ and $V_L$ of the binding protein are in a separate polypeptide chain. For example, the binding protein can be a diabody, triabody, tetrabody, Fab, F(ab')$_2$. In another example, the binding protein can be an Fv which comprises a $V_H$ and $V_L$ in separate polypeptide chains. In these examples, the binding proteins may be linked to a constant region of an antibody, Fc or a heavy chain constant domain $C_H2$ and/or $C_H3$. In another example, the binding protein can be an intact antibody. Accordingly, in an example, the present disclosure encompasses an antibody having an antigen binding domain, wherein the antigen binding domain binds to or specifically binds to DNA. For example, the antibody can bind the same epitope as a binding protein having a $V_H$ comprising an amino acid sequence as shown in SEQ ID NO: 48 and a $V_L$ comprising an amino acid sequence as shown in SEQ ID NO: 49. In another example, the antibody can bind the same epitope as a di-scFv having an amino acid sequence as shown in SEQ ID NO: 50. In an example, the antibody comprises a $V_H$ having a CDR1 as shown in SEQ ID NO: 1, a CDR2 as shown in SEQ ID NO: 2 or SEQ ID NO: 3 and a CDR3 as shown in SEQ ID NO: 4. For example, an antibody can comprise a $V_H$ having a CDR1 as shown in SEQ ID NO: 1, a CDR2 as shown in SEQ ID NO: 2 and a CDR3 as shown in SEQ ID NO: 4. In another example, an antibody can comprise a $V_H$ having a CDR1 as shown in SEQ ID NO: 1, a CDR2 as shown in SEQ ID NO: 3 and a CDR3 as shown in SEQ ID NO: 4.

In another example, the antibody comprises a $V_L$ having a CDR1 as shown in SEQ ID NO: 5 or SEQ ID NO: 6, a CDR2 as shown in SEQ ID NO: 7 and a CDR3 as shown in SEQ ID NO: 8. For example, an antibody can comprise a $V_L$ having a CDR1 as shown in SEQ ID NO: 5, a CDR2 as shown in SEQ ID NO: 7 and a CDR3 as shown in SEQ ID NO: 8. In another example, an anti-DNA binding protein can comprise a $V_L$ having a CDR1 as shown in SEQ ID NO: 6, a CDR2 as shown in SEQ ID NO: 7 and a CDR3 as shown in SEQ ID NO: 8.

In another example, the antibody comprises a $V_H$ having a CDR1 as shown in SEQ ID NO: 1, a CDR2 as shown in SEQ ID NO: 2 or SEQ ID NO: 3 and a CDR3 as shown in SEQ ID NO: 4 and a $V_L$ having a CDR1 as shown in SEQ ID NO: 5 or SEQ ID NO: 6, a CDR2 as shown in SEQ ID NO: 7 and a CDR3 as shown in SEQ ID NO: 8. For example, an antibody can comprise a $V_H$ having a CDR1 as shown in SEQ ID NO: 1, a CDR2 as shown in SEQ ID NO: 2 and a CDR3 as shown in SEQ ID NO: 4 and a $V_L$ having a CDR1 as shown in SEQ ID NO: 5, a CDR2 as shown in SEQ ID NO: 7 and a CDR3 as shown in SEQ ID NO: 8. In another example, an antibody can comprise a $V_H$ having a CDR1 as shown in SEQ ID NO: 1, a CDR2 as shown in SEQ ID NO: 2 and a CDR3 as shown in SEQ ID NO: 4 and a $V_L$ having a CDR1 as shown in SEQ ID NO: 6, a CDR2 as shown in SEQ ID NO: 7 and a CDR3 as shown in SEQ ID NO: 8. In another example, an antibody can comprise a $V_H$ having a CDR1 as shown in SEQ ID NO: 1, a CDR2 as shown in SEQ ID NO: 3 and a CDR3 as shown in SEQ ID NO: 4 and a $V_L$ having a CDR1 as shown in SEQ ID NO: 5, a CDR2 as shown in SEQ ID NO: 7 and a CDR3 as shown in SEQ ID NO: 8. In another example, an antibody can comprise a $V_H$ having a CDR1 as shown in SEQ ID NO: 1, a CDR2 as shown in SEQ ID NO: 3 and a CDR3 as shown in SEQ ID NO: 4 and a $V_L$ having a CDR1 as shown in SEQ ID NO: 6, a CDR2 as shown in SEQ ID NO: 7 and a CDR3 as shown in SEQ ID NO: 8.

Above exemplified antibodies may also have CDRs assigned using the IMGT system. Accordingly, in another example, the antibody comprises a $V_H$ having a CDR1 as shown in SEQ ID NO: 9, a CDR2 as shown in SEQ ID NO: 10 or SEQ ID NO: 11 and a CDR3 as shown in SEQ ID NO: 12. For example, an antibody can comprise a $V_H$ having a CDR1 as shown in SEQ ID NO: 9, a CDR2 as shown in SEQ ID NO: 10 and a CDR3 as shown in SEQ ID NO: 12. In another example, an antibody can comprise a $V_H$ having a CDR1 as shown in SEQ ID NO: 9, a CDR2 as shown in SEQ ID NO: 11 and a CDR3 as shown in SEQ ID NO: 12.

In another example, the antibody comprises a $V_L$ having a CDR1 as shown in SEQ ID NO: 13 or SEQ ID NO: 14, a CDR2 as shown in SEQ ID NO: 15 and a CDR3 as shown in SEQ ID NO: 16. For example, an antibody can comprise a $V_L$ having a CDR1 as shown in SEQ ID NO: 13, a CDR2 as shown in SEQ ID NO: 15 and a CDR3 as shown in SEQ ID NO: 16. In another example, an antibody can comprise a $V_L$ having a CDR1 as shown in SEQ ID NO: 14, a CDR2 as shown in SEQ ID NO: 15 and a CDR3 as shown in SEQ ID NO: 16.

In another example, the antibody comprises a $V_H$ having a CDR1 as shown in SEQ ID NO: 9, a CDR2 as shown in SEQ ID NO: 10 or SEQ ID NO: 11 and a CDR3 as shown in SEQ ID NO: 12 and a $V_L$ having a CDR1 as shown in SEQ ID NO: 13 or SEQ ID NO: 14, a CDR2 as shown in SEQ ID NO: 15 and a CDR3 as shown in SEQ ID NO: 16. For example, an antibody can comprise a $V_H$ having a CDR1 as shown in SEQ ID NO: 9, a CDR2 as shown in SEQ ID NO: 10 and a CDR3 as shown in SEQ ID NO: 12 and a $V_L$ having a CDR1 as shown in SEQ ID NO: 13, a CDR2 as shown in SEQ ID NO: 15 and a CDR3 as shown in SEQ ID NO: 16. In another example, an antibody can comprise a $V_H$ having a CDR1 as shown in SEQ ID NO: 9, a CDR2 as shown in SEQ ID NO: 10 and a CDR3 as shown in SEQ ID NO: 12 and a $V_L$ having a CDR1 as shown in SEQ ID NO: 14, a CDR2 as shown in SEQ ID NO: 15 and a CDR3 as shown in SEQ ID NO: 16. In another example, an antibody can comprise a $V_H$ having a CDR1 as shown in SEQ ID NO: 9, a CDR2 as shown in SEQ ID NO: 11 and a CDR3 as shown in SEQ ID NO: 12 and a $V_L$ having a CDR1 as shown in SEQ ID NO: 13, a CDR2 as shown in SEQ ID NO: 15 and a CDR3 as shown in SEQ ID NO: 16. In another example, an antibody can comprise a $V_H$ having a CDR1 as shown in SEQ ID NO: 9, a CDR2 as shown in SEQ ID NO: 11 and a CDR3 as shown in SEQ ID NO: 12 and a $V_L$ having a CDR1 as shown in SEQ ID NO: 14, a CDR2 as shown in SEQ ID NO: 15 and a CDR3 as shown in SEQ ID NO: 16.

In another example, the antibody comprises a $V_H$ comprising a sequence at least 95% identical to the sequence as shown in any one of SEQ ID NOs: 17 to 23. For example, an antibody can comprise a $V_H$ comprising a sequence at least 95% identical to the sequence as shown in SEQ ID NO: 18. In another example, an antibody can comprise a $V_H$ comprising a sequence at least 95% identical to the sequence as shown in SEQ ID NO: 21. In another example, an antibody can comprise a $V_H$ comprising a sequence at least 95% identical to the sequence as shown in SEQ ID NO: 23.

In another example, the antibody comprises a $V_L$ comprising a sequence at least 95% identical to the sequence as shown in any one of SEQ ID NOs: 24 to 29. For example, an antibody can comprise a $V_L$ comprising a sequence at least 95% identical to the sequence as shown in SEQ ID NO: 25. In another example, an antibody can comprise a $V_L$ comprising a sequence at least 95% identical to the sequence as shown in SEQ ID NO: 27. In another example, the antibody comprises a $V_H$ comprising a sequence at least 95% identical to the sequence as shown in any one of SEQ ID NOs: 17 to 23 and a $V_L$ comprising a sequence at least 95% identical to the sequence as shown in any one of SEQ ID NOs: 24 to 29. For example, an antibody can comprise a $V_H$ comprising a sequence at least 95% identical to the sequence as shown in SEQ ID NO: 18 and a $V_L$ comprising a sequence at least 95% identical to the sequence as shown in SEQ ID NO: 25. In another example, an antibody can comprise a $V_H$ comprising a sequence at least 95% identical to the sequence as shown in SEQ ID NO: 21 and a $V_L$ comprising a sequence at least 95% identical to the sequence as shown in SEQ ID NO: 27. In another example, an antibody can comprise a $V_H$ comprising a sequence at least 95% identical to the sequence as shown in SEQ ID NO: 23 and a $V_L$ comprising a sequence at least 95% identical to the sequence as shown in SEQ ID NO: 27. In these examples, the $V_H$ and/or $V_L$ can be at least 96%, at least 97%, at least 98% or at least 99% identical to the recited SEQ ID NO. In these examples, the antibody can have an above referenced combination of CDRs. For example, an antibody can comprise a $V_H$ comprising a sequence at least 95% identical to the sequence as shown in SEQ ID NO: 21 and a $V_L$ comprising a sequence at least 95% identical to the sequence as shown in SEQ ID NO: 27, wherein the $V_H$ has a CDR1 as shown in SEQ ID NO: 1, a CDR2 as shown in SEQ ID NO: 3 and a CDR3 as shown in SEQ ID NO: 4 and the $V_L$ has a CDR1 as shown in SEQ ID NO: 6, a CDR2 as shown in SEQ ID NO: 7 and a CDR3 as shown in SEQ ID NO: 8.

In another example, the antibody comprises a $V_H$ comprising a sequence as shown in any one of SEQ ID NOs: 17 to 23. For example, an antibody can comprise a $V_H$ comprising a sequence as shown in SEQ ID NO: 18. In another example, an antibody can comprise a $V_H$ comprising a sequence as shown in SEQ ID NO: 21. In another example, an antibody can comprise a $V_H$ comprising a sequence as shown in SEQ ID NO: 23. In another example, the antibody comprises a $V_L$ comprising a sequence as shown in any one of SEQ ID NOs: 24 to 29. For example, an antibody can comprise a $V_L$ comprising a sequence as shown in SEQ ID NO: 25. In another example, an antibody can comprise a $V_L$ comprising a sequence as shown in SEQ ID NO: 27. In another example, the antibody comprises a $V_H$ comprising a sequence as shown in any one of SEQ ID NOs: 17 to 23 and a $V_L$ comprising a sequence as shown in any one of SEQ ID NOs: 24 to 29. For example, an antibody can comprise a $V_H$ comprising a sequence as shown in SEQ ID NO: 18 and a $V_L$ comprising a sequence as shown in SEQ ID NO: 25. In another example, an antibody can comprise a $V_H$ comprising a sequence as shown in SEQ ID NO: 21 and a $V_L$ comprising a sequence as shown in SEQ ID NO: 27. In another example, an antibody can comprise a $V_H$ comprising a sequence as shown in SEQ ID NO: 23 and a $V_L$ comprising a sequence as shown in SEQ ID NO: 27.

In another example, an above referenced antibody can comprise a constant heavy region 1 comprising a sequence as shown in SEQ ID NO: 69. In another example, an above referenced antibody can comprise a constant heavy region 3 comprising a sequence as shown in SEQ ID NO: 72. In another example, an above referenced antibody can comprise a hinge region comprising a sequence as shown in SEQ ID NO: 70. In these examples, the antibody can comprise a $V_L$ comprising the amino acid sequence shown in SEQ ID NO: 27. For example, the antibody can comprise the amino acid sequence shown in SEQ ID NO: 78.

In another example, an above referenced antibody can comprise a constant heavy region 1 comprising a sequence as shown in SEQ ID NO: 69, a constant heavy region 3 comprising a sequence as shown in SEQ ID NO: 72, a hinge region comprising a sequence as shown in SEQ ID NO: 70 and a constant heavy region 2 comprising a sequence as shown in any one of SEQ ID NOs: 71, 74, 76. In this example, the antibody can comprise a $V_L$ comprising the amino acid sequence shown in SEQ ID NO: 27. For example, the antibody can comprise the amino acid sequence shown in SEQ ID NO: 78.

In another example, the antibody has an amino acid sequence shown in SEQ ID NO: 68. In another example, the antibody has an amino acid sequence shown in SEQ ID NO: 73. In another example, the antibody has an amino acid sequence shown in SEQ ID NO: 75. In another example, the antibody has an amino acid sequence shown in any one of SEQ ID NOs: 68, 73 or 75.

As known in the art, antibodies can come in different isotypes such as IgA, IgD, IgE, IgG, and IgM. In an example, antibodies encompassed by the present disclosure are IgG. In another example, antibodies encompassed by the present disclosure are IgM.

In an example, the physical stability of an antibody according to the present disclosure is greater than an Fv such as a scFv or a di-scFv having corresponding $V_H$ and $V_L$ sequences. In an example, the physical stability of an antibody according to the present disclosure is greater than a di-scFv comprising an amino acid sequence as shown in SEQ ID NO: 50 when the antibody remains in solution at 4° C. for at least four weeks. In an example, the physical stability of an antibody according to the present disclosure is greater than a di-scFv comprising an amino acid sequence as shown in SEQ ID NO: 50 when the antibody remains in solution at 4° C. for at least six months.

In another example, the antibody has reduced immunogenicity in a human subject compared to a binding protein having a $V_H$ comprising an amino acid sequence as shown in SEQ ID NO: 48 and a $V_L$ comprising an amino acid sequence as shown in SEQ ID NO: 49. For example, an antibody can have reduced immunogenicity compared to a binding protein having a $V_H$ comprising an amino acid sequence as shown in SEQ ID NO: 48 and a $V_L$ comprising an amino acid sequence as shown in SEQ ID NO: 49 when immunogenicity is measure via enzyme-linked immunosorbent assay (ELISA). In another example, an antibody can have reduced immunogenicity compared to a binding protein having a $V_H$ comprising an amino acid sequence as shown in SEQ ID NO: 48 and a $V_L$ comprising an amino acid sequence as shown in SEQ ID NO: 49 when immunogenicity is measure via Surface Plasmon Resonance.

In another example, the antibody has reduced immunogenicity in a human subject compared to a di-scFv comprising an amino acid sequence as shown in SEQ ID NO: 50. For example, an antibody can have reduced immunogenicity compared to a di-scFv comprising an amino acid sequence as shown in SEQ ID NO: 50 when immunogenicity is measure via enzyme-linked immunosorbent assay (ELISA). In another example, an antibody can have reduced immunogenicity compared to a di-scFv comprising an amino acid sequence as shown in SEQ ID NO: 50 when immunogenicity is measure via Surface Plasmon Resonance.

In an example, the antibody has a modified Fc region. For example, the antibody Fc region can comprise an amino acid sequence as shown in SEQ ID NO: 71. In another example, the antibody Fc region comprises an amino acid sequence as shown in SEQ ID NO: 74. In another example, the antibody comprises an Fc region comprising an amino acid sequence as shown in SEQ ID NO: 76. In another example, the antibody comprises an Fc region comprising an amino acid sequence as shown in any one of SEQ ID NOs: 71, 74 or 76. In another example, the antibody comprises an Fc region comprising an amino acid sequence as shown in SEQ ID NO: 77 with three amino acid substitutions. In this example, the two of the amino acid substations are between amino acid 1 and 10 of SEQ ID NO: 77. In another example, the two of the amino acid substations are between amino acid 5 and 10 of SEQ ID NO: 77. In another example, the two amino acid substitutions are at positions 7 and 8 of SEQ ID NO: 77. In these examples, the third amino acid substitution is between amino acid 65 and 75 of SEQ ID NO: 77. In another example, the third amino acid substitution is between amino acid 68 and 72 of SEQ ID NO: 77. In another example, the third amino acid substitution is between amino acid 65 and 75 of SEQ ID NO: 77. In an example, the antibody comprises an Fc region comprising an amino acid sequence as shown in SEQ ID NO: 77 with a L7A mutation. In another example, the antibody comprises an Fc region comprising an amino acid sequence as shown in SEQ ID NO: 77 with a L8A mutation. In another example, the antibody comprises an Fc region comprising an amino acid sequence as shown in SEQ ID NO: 77 with a N70D mutation. In another example, the antibody comprises an Fc region comprising an amino acid sequence as shown in SEQ ID NO: 77 with L7A and L8A mutations. In another example, the antibody comprises an Fc region comprising an amino acid sequence as shown in SEQ ID NO: 77 with L7A and N70D mutations. In another example, the antibody comprises an Fc region comprising an amino acid sequence as shown in SEQ ID NO: 77 with L8A and N70D mutations. In another example, the antibody comprises an Fc region comprising an amino acid sequence as shown in SEQ ID NO: 77 with L7A, L8A and N70D mutations.

Although variation in the disclosed sequences including heavy and light chain polypeptide sequences, and CDRs thereof, is generally provided above with at least 95% sequence identity to the reference sequence, variants with less identity are also expressly disclosed. Thus, in some examples, a DNA binding protein includes a polypeptide at least 70%, at least 75%, at least 80%, at least 85%, at least 90%, at least 91%, at least 92%, at least 93%, or at least 94% identical to the amino acid sequence of the polypeptide of any of SEQ ID NOS: 32-47. In some embodiments, a DNA binding protein includes a variable heavy chain and/or light chain having at least 70%, at least 75%, at least 80%, at least 85%, at least 90%, at least 91%, at least 92%, at least 93%, or at least 94% identical to the amino acid sequence of the heavy and/or light chain of any of SEQ ID NOS: 32-47 (e.g., any of SEQ ID NO:17-29). In some embodiments, a DNA binding protein includes one or more CDRs having least 70%, at least 75%, at least 80%, at least 85%, at least 90%, at least 91%, at least 92%, at least 93%, or at least 94% identical to the amino acid sequence of the CDRs of any of SEQ ID NOS: 32-47 (e.g., any of SEQ ID NO: 1-16).

Binding Protein Production
Recombinant Expression

In one example, a binding protein as described herein is a peptide or polypeptide (e.g., is an antibody or antigen binding fragment thereof). In one example, the binding protein is recombinant.

In the case of a recombinant peptide or polypeptide, nucleic acid encoding same can be cloned into expression vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce immunoglobulin or antibody protein.

Suitable molecular cloning techniques are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art. See U.S. Pat. No. 4,816,567 or 5,530,101.

Following isolation, the nucleic acid is inserted operably linked to a promoter in an expression construct or expression vector for further cloning (amplification of the DNA) or for expression in a cell-free system or in cells. Thus, another example of the disclosure provides an expression construct that comprises an isolated nucleic acid of the disclosure and one or more additional nucleotide sequences. Suitably, the expression construct is in the form of, or comprises genetic components of, a plasmid, bacteriophage, a cosmid, a yeast or bacterial artificial chromosome as are understood in the art. Expression constructs may be suitable for maintenance and propagation of the isolated nucleic acid in bacteria or other host cells, for manipulation by recombinant DNA technology and/or for expression of the nucleic acid or a binding protein of the disclosure.

Many vectors for expression in cells are available. The vector components generally include, but are not limited to, one or more of the following: a signal sequence, a sequence encoding the binding protein (e.g., derived from the information provided herein), an enhancer element, a promoter, and a transcription termination sequence. Exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin or antibody promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the binding protein (e.g., antibody or antigen binding fragment) may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

The skilled artisan will understand from the foregoing description that the present disclosure also provides an isolated nucleic acid encoding a binding protein (e.g., a peptide or polypeptide binding protein or an antibody or antigen binding fragment thereof) of the present disclosure.

The present disclosure also provides an expression construct comprising an isolated nucleic acid of the disclosure operably linked to a promoter. In one example, the expression construct is an expression vector.

In one example, the expression construct of the disclosure comprises a nucleic acid encoding a polypeptide (e.g., comprising a $V_H$) operably linked to a promoter and a nucleic acid encoding another polypeptide (e.g., comprising a $V_L$) operably linked to a promoter.

The disclosure also provides a host cell comprising an expression construct according to the present disclosure.

The present disclosure also provides an isolated cell expressing a binding protein of the disclosure or a recombinant cell genetically-modified to express the binding protein.

Isolation of Proteins

Methods for purifying binding proteins according to the present disclosure are known in the art and/or described herein. An example is provided in Example 1 below.

Where a peptide or polypeptide is secreted into the medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The binding protein prepared from cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

Conjugates

In one example, a binding protein of the present disclosure is conjugated to another compound. The binding protein can be directly or indirectly bound to the compound (e.g., can comprise a linker in the case of indirect binding). Examples of compounds include, a radioisotope (e.g., iodine-131, yttrium-90 or indium-111), a detectable label (e.g., a fluorophore or a fluorescent nanocrystal or quantum dot), a therapeutic compound (e.g., a chemotherapeutic or an anti-inflammatory), a colloid (e.g., gold), a toxin (e.g., ricin or tetanus toxoid), a nucleic acid, a peptide (e.g., a serum albumin binding peptide), a protein (e.g., a protein comprising an antigen binding domain of an antibody or serum albumin), an agent that increases the half-life of the compound in a subject (e.g., polyethylene glycol or other water soluble polymer having this activity) and mixtures thereof.

Methods for attaching a drug or other small molecule pharmaceutical to an antibody are well known and can include use of bifunctional chemical linkers such as N-succinimidyl (4-iodoacetyl)-aminobenzoate; sulfosuccinimidyl (4-iodoacetyl)-aminobenzoate; 4-succinimidyl-oxycarbonyl-(2-pyridyldithio) toluene; sulfosuccinimidyl-6-[α-methyl-∀-(pyridyldithiol)-toluamido]hexanoate; N-succinimidyl-3-(-2-pyridyldithio)-proprionate; succinimidyl-6-[3 (-(-2-pyridyldithio)-proprionamido]hexanoate; sulfosuccinimidyl-6-[3 (-(-2-pyridyldithio)-propionamido] hexanoate; 3-(2-pyridyldithio)-propionyl hydrazide, Ellman's reagent, dichlorotriazinic acid, S-(2-thiopyridyl)-L-cysteine, and the like. Further bifunctional linking molecules are discussed in, for example, U.S. Pat. Nos. 5,349,066, 5,618,528, 4,569,789, 4,952,394, and 5,137,877.

The linker can cleavable or noncleavable. Highly stable linkers can reduce the amount of payload that falls off in circulation, thus improving the safety profile, and ensuring that more of the payload arrives at the target cell. Linkers can be based on chemical motifs including disulfides, hydrazones or peptides (cleavable), or thioethers (noncleavable) and control the distribution and delivery of the active agent to the target cell. Cleavable and noncleavable types of linkers have been proven to be safe in preclinical and clinical trials (see, e.g., Brentuximab vedotin which includes an enzyme-sensitive linker cleavable by cathepsin; and Trastuzumab emtansine, which includes a stable, non-cleavable linker). In particular embodiments, the linker is a peptide linker cleavable by Edman degredation (Bąchor, et al., *Molecular diversity*, 17 (3): 605-11 (2013)).

A non-cleavable linker can keep the active agent within the cell or the target microenvironment. As a result, the entire antibody, linker and active agent enter the targeted cell where the antibody is degraded to the level of an amino acid. The resulting complex between the amino acid of the antibody, the linker and the active agent becomes the active drug. In contrast, cleavable linkers are catalyzed by enzymes in the target cell or microenvironment where it releases the active agent. Once cleaved, the payload can escape from the targeted cell and attack neighboring cells (also referred to as "bystander killing"). In the case of the disclosed binding proteins, cleavage of the linker can lead to two active agents, the antibody itself and its payload, which can have different mechanisms of action in the target cell or microenivornment.

In some embodiments, there is one or more additional molecules, between the active agent and the cleavage site.

Other considerations include site-specific conjugation (TDCs) (Axup, *Proceedings of the National Academy of Sciences*, 109 (40): 16101-6 (2012) and conjugation techniques such as those described in Lyon, et al., *Bioconjugate Chem.*, 32 (10): 1059-1062 (2014), and Kolodych, et al., *Bioconjugate Chem.*, 26 (2): 197-200 (2015) which can improve stability and therapeutic index, and α emitting immunoconjugates (Wulbrand, et at, Multhoff, Gabriele, ed., *PLoS ONE*. 8 (5): e64730 (2013)).

In an example, the binding protein is conjugated to nanoparticles or microparticles (for example as reviewed in Kogan et al., *Nanomedicine* (Loud). 2: 287-306, 2007). The nanoparticles may be metallic nanoparticles. The particles can be polymeric particles, liposomes, micelles, microbubbles, and other carriers and delivery vehicles known in the art.

If the delivery vehicle is a polymeric particle, the binding protein can be coupled directly to the particle or to an adaptor element such as a fatty acid which is incorporated into the polymer. Ligands may be attached to the surface of polymeric particles via a functional chemical group (carboxylic acids, aldehydes, amines, sulfhydryls and hydroxyls) present on the surface of the particle and present on the ligand to be attached. Functionality may be introduced post-particle preparation, by crosslinking of particles and ligands with homo- or heterobifunctional crosslinkers. This procedure may use a suitable chemistry and a class of crosslinkers (CDT, EDAC, glutaraldehydes, etc. as discussed in more detail below) or any other crosslinker that couples ligands to the particle surface via chemical modification of the particle surface after preparation.

Binding proteins may also be attached to polymeric particles indirectly though adaptor elements which interact with the polymeric particle. Adaptor elements may be attached to polymeric particles in at least two ways. The first is during the preparation of the micro- and nanoparticles, for example, by incorporation of stabilizers with functional chemical groups during emulsion preparation of microparticles. For example, adaptor elements, such as fatty acids, hydrophobic or amphiphilic peptides and polypeptides can be inserted into the particles during emulsion preparation. In a second embodiment, adaptor elements may be amphiphilic molecules such as fatty acids or lipids which may be passively adsorbed and adhered to the particle surface, thereby introducing functional end groups for tethering to binding proteins. Adaptor elements may associate with micro- and nanoparticles through a variety of interactions including, but not limited to, hydrophobic interactions, electrostatic interactions and covalent coupling.

Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for particles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof.

Some exemplary compounds that can be conjugated to a binding protein of the present disclosure are listed in Table 1.

TABLE 1

Compounds useful in conjugation.

| Group | Detail |
|---|---|
| Radioisotopes (either directly or indirectly) | $^{123}$I, $^{125}$I, $^{130}$I, $^{131}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Gu, $^{68}$Gu, $^{67}$Cu, $^{75}$Br, $^{76}$Br, $^{77}$Br, $^{99m}$Tc, $^{11}$C, $^{13}$N, $^{15}$O,$^{18}$I, $^{188}$Rc, $^{203}$Pb, $^{64}$Cu, $^{105}$Rh, $^{198}$Au, $^{199}$Ag or $^{177}$Lu |
| Half-life extenders | Polyethylene glycol<br>Glycerol<br>Glucose |
| Fluorescent probes | Phycoerythrin (PE)<br>Allophycocyanin (APC)<br>Alexa Fluor 488<br>Cy5.5 |
| Biologics | fluorescent proteins such as Renilla luciferase, GFP<br>immune modulators or proteins, such as cytokines, e.g., an interferon<br>toxins<br>an immunoglobulin or antibody or antibody variable region<br>half-life extenders such as albumin or antibody variable regions or peptides that bind to albumin |
| Chemo-therapeutics | Taxol<br>5-FU<br>Doxorubicin<br>Idarubicin |

In one example, a binding protein of the disclosure is conjugated to a chemotherapy agent.

In one example, a binding protein of the disclosure is conjugated to a maytansinoid, e.g., DM1 or DM4.

In another example, a binding protein of the disclosure is conjugated to an auristatin, e.g., MMAE or MMAD.

In another example, a binding protein of the disclosure is conjugated to and enzyme, e.g., MTM1, GAA or AGL.

In another example, a binding protein of the disclosure is conjugated to MBNL.

In another example, a binding protein of the disclosure is conjugated to a heat shock protein (HSP). In various examples, a binding protein of the disclosure is conjugated to a HSP from family HSP33, HSP70, HSP90, HSP100, small HSP (sHSP) or a combination thereof. For example, a binding protein of the disclosure can be conjugated to HSP72. Accordingly, in an example, the present disclosure encompasses an Fv conjugated to a HSP from HSP70 family. In another example, the present disclosure encompasses an Fv conjugated to HSP72.

In another example, a binding protein of the disclosure is conjugated to a PARP inhibitor disclosed herein. For example, a binding protein of the disclosure can be conjugated to olaparib.

In one aspect of the above examples, binding protein conjugates can be used to deliver conjugated payloads to a cell. Exemplary cells include cardiac cells such as cardiomyocytes, lung cells such as alveolar cells and neural cells such as neurons. Other exemplary cells include cancerous cells or virally infected cells.

In some embodiments, one or more the foregoing compounds are expressly excluded from being conjugated to the disclosed binding proteins. For example, the binding protein can be naked.

Compositions

Suitably, in compositions or methods for administration of a binding protein according to the present disclosure to a subject, the binding protein is combined with a pharmaceutically acceptable carrier as is understood in the art. In one example, the present disclosure provides a composition (e.g., a pharmaceutical composition) comprising a binding protein of the disclosure combined with a pharmaceutically acceptable carrier. In another example, the disclosure provides a kit comprising a pharmaceutically acceptable carrier suitable for combining or mixing with a binding protein prior to administration to the subject. In this example, the kit may further comprise instructions for use.

In general terms, "carrier" is used to refer to a solid or liquid filler, binder, diluent, encapsulating substance, emulsifier, wetting agent, solvent, suspending agent, coating or lubricant that may be safely administered to a subject, e.g., a human subject. Depending upon the particular route of administration, a variety of acceptable carriers, known in the art may be used, as for example described in Remington's Pharmaceutical Sciences (Mack Publishing Co. N.J. USA, 1991).

For example, suitable carriers may be selected from a group including sugars (e.g. sucrose, maltose, trehalose, glucose), starches, cellulose and its derivatives, malt, gelatine, talc, calcium sulfate, oils inclusive of vegetable oils, synthetic oils and synthetic mono- or di-glycerides, lower alcohols, polyols, alginic acid, phosphate buffered solutions, lubricants such as sodium or magnesium stearate, isotonic saline and pyrogen-free water. In an example, the carrier is not $H_2O$.

In an example, the carrier is compatible with, or suitable for, parenteral administration. Parenteral administration includes any route of administration that is not through the alimentary canal. Examples of parenteral administration include injection, infusion and the like. Examples of administration by injection include intravenous, intra-arterial, intramuscular and subcutaneous injection. In another example, compositions can be delivered via a depot or slow-release formulation which may be delivered intradermally, intramuscularly or subcutaneously.

In some embodiments, the binding protein is encapsulated or incorporated in nanoparticle, microparticle, or other delivery vehicle such as, but not limited to, those discussed above.

In some embodiments, a DNA binding protein is utilized detecting site or sites of cancer, tissue damage, injury, infection, or ischemia. The method typically including administering to a subject in need thereof an effective amount an agent that is detectable using diagnostic imaging or nuclear medicine techniques, and detecting the agent. In such methods, the agent is typically conjugated to the DNA binding protein or encapsulated in a delivery vehicle conjugated with the DNA binding protein. The diagnostic imaging or nuclear medicine technique can be, for example, PET-CT, bone scan, MRI, CT, echocardiography, ultrasound, and x-ray.

In an example, binding proteins and compositions comprising the same can be used in the manufacture of a medicament for the treatment of a condition. In another example, the present disclosure relates to a binding protein or compositions comprising the same for use in the treatment of a condition. Examples of conditions to be treated are discussed below.

The methods and uses typically include administering a subject in need there of an effective amount of a binding protein. In some embodiments, the subject has cancer or virally infected or transformed cells. In some embodiments, the subject has a disease or disorder characterized by exogenous or extracellular DNA, including but not limited to, ischemia, tissue damage, injury, or an infection. The methods and uses can include a combination therapy with a second, third, or more additional active agents. For example, the disclosed binding proteins can be used in combination with standard chemotherapy, radiation therapy, and other anti-cancer treatments. Radiation therapy (a.k.a. radiotherapy) is the medical use of ionizing radiation as part of cancer treatment to control malignant cells.

Combination Therapy

Data compiled by the present inventors indicates that the disclosed binding proteins work with poly (ADP-ribose) polymerase (PARP) inhibitors to kill cancer cells. For example, more than additive cell death was observed in HDR-deficient cancer cells treated with di-scFv and PARP inhibitor.

Accordingly, in another example, the present disclosure encompasses a method of treating cancer in a subject in need thereof, the method comprising administering to the subject a binding protein disclosed herein and a PARP inhibitor. In another example, the present disclosure relates to a therapeutic combination comprising a binding protein disclosed herein and a PARP inhibitor, the combination being provided for simultaneous or sequential administration. In another example, the present disclosure relates to a therapeutic combination comprising a binding protein disclosed herein and a PARP inhibitor for use in treating cancer.

In an example, the PARP inhibitor is selected from the group consisting of olaparib, niraparib, veliparib, rucaparib, talazoparib and BGB-290. For example, the PARP inhibitor can be olaparib.

Examples of binding proteins suitable for administration with a PARP inhibitor are provided above. In one example, the binding protein comprises a $V_H$ having a CDR1 as shown in SEQ ID NO: 1, a CDR2 as shown in SEQ ID NO: 2 and a CDR3 as shown in SEQ ID NO: 4 and a $V_L$ having a CDR1 as shown in SEQ ID NO: 5, a CDR2 as shown in SEQ ID NO: 7 and a CDR3 as shown in SEQ ID NO: 8. In another example, the binding protein comprises a $V_H$ having a CDR1 as shown in SEQ ID NO: 1, a CDR2 as shown in SEQ ID NO: 2 and a CDR3 as shown in SEQ ID NO: 4 and a $V_L$ having a CDR1 as shown in SEQ ID NO: 6, a CDR2 as shown in SEQ ID NO: 7 and a CDR3 as shown in SEQ ID NO: 8. In another example, the binding protein comprises a $V_H$ having a CDR1 as shown in SEQ ID NO: 1, a CDR2 as shown in SEQ ID NO: 3 and a CDR3 as shown in SEQ ID NO: 4 and a $V_L$ having a CDR1 as shown in SEQ ID NO: 5, a CDR2 as shown in SEQ ID NO: 7 and a CDR3 as shown in SEQ ID NO: 8. In another example, the binding protein comprises a $V_H$ having a CDR1 as shown in SEQ ID NO: 1, a CDR2 as shown in SEQ ID NO: 3 and a CDR3 as shown in SEQ ID NO: 4 and a $V_L$ having a CDR1 as shown in SEQ ID NO: 6, a CDR2 as shown in SEQ ID NO: 7 and a CDR3 as shown in SEQ ID NO: 8. In these examples, the binding protein can be an Fv. In an example, the binding protein can be a di-scFv.

Subjects having one or more of the conditions discussed below may be treated by administering a binding protein disclosed herein and a PARP inhibitor. In an example, the subject has pancreatic cancer. In another example, the subject has colon cancer. In an example, the subject has a cancer that is substantially BRCA2 deficient.

In another example, an above referenced combination therapy can be used to treat subjects with cancer resistant to PARP inhibitor therapy.

In an example, the binding protein and PARP inhibitor are administered as a single composition.

In another example, the binding protein and PARP inhibitor are administered as separate compositions. For example, the binding protein and PARP inhibitor can be administered simultaneously. In another example, binding protein and PARP inhibitor can be administered sequentially. In this example, administration of the binding protein and PARP inhibitor is carried out over a defined time period (usually minutes, hours or days). In an example, the period between sequential administration can be several days, provided that there is still sufficient levels of the first therapeutic to provide or add to the therapeutic benefit of the second therapeutic when it is administered. In one example, administration of a binding protein is followed by sequential administration of a PARP inhibitor. In another example, administration of a PARP inhibitor is followed by sequential administration of a binding protein.

Therapeutic combinations according to the present disclosure can be administered via various routes. Exemplary routes of administration include intravenous administration as a bolus or by continuous infusion over a period of time, intramuscular, intraperitoneal, intracerobrospinal, intrathecal, oral routes.

In an example, the binding protein and PARP inhibitor are administered via the same route. For example, both the binding protein and PARP inhibitor can be administered intravenously via continuous infusion. In another example, the binding protein and PARP inhibitor are administered via different routes. For example, the binding protein can administered intravenously via continuous infusion and the PARP inhibitor can be administered orally.

In some examples, administration of a binding protein or Fv fragment defined herein and a PARP inhibitor achieves a result greater than when the binding protein or Fv fragment and the PARP inhibitor are administered alone or in isolation. For example, the result achieved by the combination can be more than additive of the results achieved by the individual components alone.

In an example, administration of the combination of a binding protein or Fv fragment defined herein and a PARP inhibitor is effective to reduce cancer cell proliferation or viability in a subject with cancer to a greater degree than administering to the subject the same amounts of the individual components alone. For example, the reduction in cancer cell proliferation or viability in the subject with cancer can be more than the additive of the results achieved by the individual components alone. In some examples, in subjects with cancer, the combination is effective to reduce tumour burden, reduce tumour progression, or a combination thereof, which may also be more than additive of the results achieved by the individual components alone.

Conditions to be Treated

In an example, binding proteins according to the present disclosure can be administered to a subject to treat various conditions.

In some examples of the disclosure, a method described herein is for the treatment of a cancer. The term "cancer" refers to or describes the physiological condition in mammals that is typically characterized by unregulated cell growth/proliferation. Examples of cancer include but are not limited to, carcinoma, lymphoma, blastoma, sarcoma, and leukemia or lymphoid malignancies. More particular examples of such cancers include, but are not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In another example, the term "cancer" encompasses triple negative breast cancer. Accordingly, in an example, the present disclosure relates to a method of treating breast, ovarian, colon, prostate, lung, brain, skin, liver, stomach, pancreatic or blood based cancer. In another example, the present disclosure relates to treating glioblastoma. In this example, glioblastoma may be treated by administering a binding protein disclosed herein such as a di-scFv having SEQ ID NO: 41 or an antibody having the heavy and light chain variable regions defined in SEQ ID NO: 41.

In other examples, a method described herein is used to treat cancers that are linked to mutations in BRCA1, BRCA2, PALB2, OR RAD51B, RAD51C, RAD51D or related genes. In other examples, a method described herein is used to treat cancers that are linked to mutations in genes associated with DNA mismatch repair, such as MSH2, MLH1, PMS2, and related genes. In other examples, a method described herein is used to treat cancers with silenced DNA repair genes, such as BRCA1, MLH1, OR RAD51B, RAD51C, OR RAD51D.

In another example, a method described herein is used to kill cells with impaired DNA repair processes. For example, cells with impaired DNA repair may aberrantly express a gene involved in DNA repair, DNA synthesis, or homologous recombination. Exemplary genes include XRCC1, ADPRT (PARP-1), ADPRTL2, (PARP-2), POLYMERASE BETA, CTPS, MLH1, MSH2, FANCD2, PMS2, p53, p21, PTEN, RPA, RPA1, RPA2, RPA3, XPD, ERCC1, XPF, MMS19, RAD51, RAD51B, RAD51C, RAD51D, DMC1, XRCCR, XRCC3, BRCA1, BRCA2, PALB2, RAD52, RAD54, RAD50, MREU, NB51, WRN, BLM, KU70, KU80, ATM, ATR CPIK1, CHK2, FANCA, FANCB, FANCC, FANCD1, FANCD2, FANCE, FANCF, FANCG, FANCC, FANCD1, FANCD2, FANCE, FANCF, FANCG, RAD1, and RADS. In an example, a method described herein can be used to kill HDR deficient cells. In another example, a method described herein is used to kill cells with a mutant tumor suppressor gene. For example, cells can have one or more mutations in BRCA1 or BRCA2. For example, cells can be BRCA2 deficient colon cancer cells.

In an example, a method described herein is for the treatment of a cancer that is substantially HDR deficient. In an example, a method described herein is for the treatment of a cancer that is substantially BRCA2 deficient. For example, a BRCA2 deficient colon cancer may be treated. In another example, a method described herein is for the treatment of a cancer that is substantially PTEN deficient. For example, a PTEN deficient brain cancer may be treated. In another example, a method described herein is for the treatment of a cancer that is resistant to PARP inhibition.

In other examples of the disclosure, a method described herein is used to treat virally transformed cells, such as cells infected with an oncovirus. The term "oncovirus" is used in the context of the present disclosure to refer to viruses that are able to replicate in and reduce growth of tumour cells. In an example, the oncovirus virus is able to naturally replicate in and reduce growth of tumour cells. Examples of such viruses include Newcastle disease virus, vesicular stomatitis, myxoma, reovirus, sindbis, measles and coxsackievirus. In another example, the oncovirus virus is engineered to replicate in and reduce growth of tumour cells. Exemplary viruses suitable for such engineering include adenovirus, herpes simplex virus (HSV), lentivirus, vaccina and vesicular stomatitis virus (VSV).

Other exemplary oncoviruses include Human papillomaviruses (HPV), Hepatitis B (HBV), Hepatitis C (HCV), Human T-lymphotropic virus (HTLV), Kaposi's sarcoma-associated herpesvirus (HHV-8), Merkel cell polyomavirus, Epstein-Barr virus (EBV), Human immunodeficiency virus (HIV), and Human cytomegalovirus (CMV).

In other examples of the disclosure, a method described herein is used to kill cells transformed with a latent virus. Exemplary latent viruses include CMV, EBV, Herpes simplex virus (type 1 and 2), and Varicella zoster virus.

In other examples of the disclosure, a method described herein is used to treat active viral infections due to viruses that give rise to cancer, immunodeficiency, hepatitis, encephalitis, pneumonitis or respiratory illness. Exemplary viruses include above referenced oncovirus, parvovirus, poxvirus, herpes virus.

In other examples of the disclosure, a method described herein is used to treat Colorado Tick Fever (caused by Coltivirus, RNA virus), West Nile Fever (encephalitis, caused by a flavivirus that primarily occurs in the Middle East and Africa), Yellow Fever, Rabies (caused by a number of different strains of neurotropic viruses of the family Rhabdoviridae), viral hepatitis, gastroenteritis (viral)-acute viral gastroenteritis caused by Norwalk and Norwalk-like viruses, rotaviruses, caliciviruses, and astroviruses, poliomyelitis, influenza (flu), caused by orthomyxoviruses that can undergo frequent antigenic variation, measles (rubeola), paramyxoviridae, mumps, respiratory syndromes including viral pneumonia and acute respiratory syndromes including croup caused by a variety of viruses collectively referred to as acute respiratory viruses, and respiratory illness caused by the respiratory syncytial virus.

In other examples of the disclosure, a method described herein is used to treat a nucleotide repeat disorder or an exon splicing disorder. In other examples of the disclosure, a method described herein is used to treat a disorder associated with aberrant microsatellite expansion, such as myotonic dystrophy. For example, the methods of the present disclosure may be used to treat Myotonic dystrophy. Examples of Myotonic dystrophy type 1 (DM1; trinucleotide $(CTG)_n$ expansion of n=50 to >3000 in the 3'-untranslated region of the Dystrophia myotonica-protein kinase (DMPK) gene) and type 2 (DM2; tetranucleotide $(CCTG)_n$ expansion of n=75 to about 11,000 in the first intron of zinc finger protein 9 (ZNF9) gene. In other examples of the disclosure, a method described herein is used to treat neurofibramotosis. In other examples of the disclosure, a method described herein is used to treat Huntington's Disease. In other examples of the disclosure, a method described herein is used to treat myotubular myopathy. In other examples of the disclosure, a method described herein is used to treat a glycogen storage disorder. In other examples of the disclosure, a method described herein is used to treat Pompe Disease. In other examples of the disclosure, a method described herein is used to treat Forbes-Cori Disease. In other examples of the disclosure, a method described herein is used to treat Lafora Disease.

In other examples of the disclosure, a method described herein is used to increase Muscleblind-like (MBNL) activity in a cell in vitro or in a subject by administering a binding protein according to the present disclosure conjugated to an MBNL polypeptide. In other examples of the disclosure, a method described herein is used for enzyme or protein replacement therapy.

In other examples of the disclosure, a method described herein is used to increase HSP activity in a cell in vitro or in a subject by administering a binding protein according to the present disclosure conjugated to a HSP from HSP70 family. In other examples of the disclosure, a method described herein is used to increase HSP72 activity in a cell in vitro or in a subject by administering a binding protein according to the present disclosure conjugated to an HSP72 polypeptide.

EXAMPLES

Example 1—Expression and Purification of di-scFV Variants

Single gene GS vectors (using Lonza's GS Xceed™ Gene Expression System) were established, sequenced, linearized and used to generate a stable pool for each variant. Following cryopreservation the propagated stable pools were expanded to 200 mL culture volume each and subjected to an abridged fed batch overgrow with a single bolus feed on day 4 and harvested on day 8. Supernatant titre was determined by Protein L Octet. Clarified supernatant for ion exchange purification was obtained by centrifugation followed by filter sterilisation using a 0.22 µm filter. An ion exchange purification method was developed using the dimer version of the murine antibody as a reference.

Clarified supernatant was purified using a pre-packed 5 mL HiTrap Capto S column (GE Healthcare, 17-544122) on an AKTA purifier (run at 5 mL/min). The column was equilibrated with 50 mM Sodium Phosphate pH 6 before and after sample loading and the product was eluted with a linear gradient from 0-1 M NaCl. Quantification of bound and unbound material by Protein L Octet showed that approximately 57% of material remained in the unbound fraction. Repeating the chromatography using the unbound fraction again resulted in approximately 64% of the starting material remaining in the unbound fraction.

Purification of the remaining supernatants was performed using two sequential steps of ion exchange chromatography with a linear elution gradient from 0-1 M NaCl. Following purification, the products were quantified and concentrated to approximately 1 mg/mL by ultrafiltration using Amicon Ultra-15 filters (Millipore, UFC903024).

Duplicate samples were analysed by SE-HPLC on an Agilent 1200 series HPLC system, using a Zorbax GF-250 9.4 mm ID×25 cm column (Agilent) and by SDS-PAGE analysis. Yields and titres of expression cultures are summarised in Table 1. SDS-PAGE analysis of variants is shown in FIGS. 1 and 2.

TABLE 1

Yields and titres of expression cultures.

| Product | Estimated Titre (mg/L) | Final concentration (mg/mL) | Volume (mL) | Final Yeild (mg) | Monomer (%) |
|---|---|---|---|---|---|
| var_2 | 393.4 | 1.079 | 3.2 | 3.5 | 84.08 |
| var_3 | 436.8 | 1.156 | 1.5 | 1.7 | 80.61 |
| var_4 | 445.0 | 1.090 | 2.5 | 2.7 | 84.26 |
| var_6 | 275.7 | 1.214 | 1.6 | 1.9 | 93.02 |
| var_7 | 288.4 | 0.829 | 1.5 | 1.2 | 79.16 |
| var_8 | 373.7 | 1.024 | 2.0 | 2.0 | 81.71 |
| var_10 | 325.2 | 0.767 | 5.6 | 4.3 | 85.17 |
| var_11 | 349.7 | 1.181 | 6.2 | 7.3 | 81.86 |
| var_12 | 396.1 | 1.169 | 4.0 | 4.7 | 80.86 |
| var_13 | 459.1 | 0.803 | 5.0 | 4.0 | 86.13 |
| var_14 | 527.5 | 0.799 | 4.0 | 3.2 | 82.72 |
| var_15 | 584.2 | 1.003 | 3.2 | 3.2 | 86.34 |
| var_16 | 391.9 | 0.842 | 5.6 | 4.7 | 85.53 |
| var_17 | 315.6 | 1.106 | 1.8 | 2.0 | 85.79 |
| var_18 | 460.3 | 1.118 | 4.5 | 5.0 | 85.37 |
| var_19 | 318.9 | 0.401 | 3.1 | 1.2 | 84.47 |
| tri_L1H2 | 251.4 | 1.091 | 3.2 | 3.5 | 95.47 |
| Di_scFv_B72.3 | 55.7 | | 0.0 | 0.0 | |
| di_scFv_D31N | 270.7 | 1.027 | 6.6 | 6.8 | 95.36 |
| tri_scFv_D31N | 40.2 | 0.658 | 2.5 | 1.6 | 93.34 |

Example 2—Nuclear Penetration of Variants

Alkaline Phosphatase-Based Survey of Nuclear Penetration

DLD1 colon cancer cells were treated with control media or each of the indicated variants for one hour. Cells were then washed, fixed, blocked with 1% BSA-TBST, and then probed with protein L for one hour. Cells were then washed and incubated with an anti-protein L primary antibody for one hour. After another round of washing cells were incubated with an alkaline phosphatase-conjugated secondary antibody for one hour. Finally, cells were washed and signal was developed by addition of NBT/BCIP. Representative images are shown in FIG. 3. Dark stain indicates location of the variants.

Raw integrated density values reflecting nuclear alkaline phosphatase staining in the DLD1 cells from the experiment in FIG. 3 were obtained by analysis using ImageJ. Boxplots of distributions of values are presented for each variant in FIG. 4.

Histogram plots of cell counts versus nuclear staining intensity (represented as reciprocal intensity in arbitrary units) are shown in FIG. 5. Most of the variants, other than variants 12 and 14, showed improved nuclear penetration relative to the yeast prototype, which is demonstrated by right shift of histogram peak. In addition, the narrowing of distributions observed in the histograms for most of the humanized variants shows improved uniformity of nuclear penetration relative to the yeast prototype. Variants 13 and 15 in particular showed notable right shift and narrowing of distributions relative to the yeast prototype.

Immunofluorescence-Based Survey of Nuclear Penetration

DLD1 colon cancer cells were treated with control media or each of the indicated variants for one hour. Cells were then washed, fixed, blocked with 1% BSA-TBST, and then probed with protein L for one hour. Cells were then washed and incubated with an anti-protein L primary antibody for one hour. After another round of washing cells were incubated with an Alexa488-conjugated secondary antibody for one hour. Finally, cells were washed and signal was visualized by fluorescence microscopy. Representative images are shown in FIG. 6. Green signal indicates location of the variants.

Raw integrated density values reflecting Alexa488 fluorescence signal in the DLD1 cells from the experiment in FIG. 6 were obtained by analysis using ImageJ. Boxplots of distributions of values are presented for each variant in FIG. 7.

Example 2—Accumulation of DNA Damage

A matched pair of PTEN-proficient and deficient U251 human glioma cells were treated with control media or media containing Variant 10, 11, 13, 15, or 16 for twenty-four hours. Cells were then washed, fixed, blocked, and then probed with an anti-phospho-53BP1 antibody overnight. Cells were then washed and incubated with an AlexaFluor555-conjugated secondary antibody. Finally, cells were washed, counterstained with DAPI, and visualized under a fluorescence microscope. Images were saved and evaluated by CellProfiler to determine mean number of phospho-53BP1 foci per cell. The new variants increased the number of foci in the PTEN-deficient cells, but not the PTEN-proficient cells. Representative images are shown in FIG. 8, Panel A, and quantitative analysis by CellProfiler is shown in FIG. 8, Panel B.

Cell viability of PTEN-deficient U87 human glioma cells was also assessed following treatment with control media or media containing Variants 10, 13, 15, or 16. Cell viability was determined 7 days after treatment using Trypan blue exclusion assay and by direct visualization of cell morphology by light microscopy. All variants caused reductions in cell viability relative to control treated cells (FIG. 9).

Next, a matched pair of BRCA2-proficient and deficient DLD1 colon cancer cells was treated with control media or media containing Variants 10, 13, 15, or 16. Cell viability was determined 7 days later by Trypan blue exclusion assay and by direct visualization of cell morphology by light microscopy. The variants were not toxic to the BRCA2-proficient cells, but the BRCA2-deficient cells were killed by the variants. These data indicate that variants are able to selectively kill cancer cells with impaired DNA repair. Moreover, these data indicate that that the variants will be able to discriminate between cancerous cells with impaired DNA repair and healthy cells to selectively kill cancer cells. Representative light microscope images shown the changes in morphology in the BRCA2-deficient cancer cells treated with the variants are shown in FIG. 10, Panel A. Quantitative analysis of the cell survival by Trypan blue exclusion assay is shown in FIG. 10, Panel B.

Example 3—Di-scFv Co-Administration with PARP Inhibition in HDR Deficient Cancer Cells DLD-1 and MCF-7 cells were treated with control or di-scFv (SEQ ID NO: 41), and nuclear penetration was evaluated by protein L immunostain of fixed cells. The di-scFv successfully penetrated DLD-1 and MCF-7 cell nuclei (FIGS. 11 and 12).

Homology-directed repair (HDR) deficient BRCA2-DLD1 cells and PTEN-U251 cells were treated with control, 5 nM olaparib, 10 μM di-scFv, or 10 μM di-scFv+5 nM olaparib. Surviving fraction was determined by colony formation assay. Surprisingly, more than additive cell death was observed in HDR-deficient cancer cells treated with di-scFv and the PARP inhibitor (FIG. 13).

It was then determined whether the combination of di-scFv and olaparib is simply universally cytotoxic, regardless of DNA repair status. To evaluate this possibility, HDR-proficient DLD1 cells were treated with the above regimen to confirm selectivity of combination therapy to HDR-deficient malignant cells. No effect on cell death was observed for the di-scFv alone or in combination with PARP inhibitor. These findings demonstrate that HDR-proficient cells remain resistant to the effects of both the di-scFv and olaparib, even when used in combination.

Example 4—Effect of Di-scFv (SEQ ID NO: 41) on Primary Human Glioblastoma (GBM) Cells Primary human glioblastoma (GBM) cancer cells extracted from primary human GBM tumours from patients were treated with control or di-scFv (SEQ ID NO: 41), and percentage of live cells was evaluated by trypan blue staining. Five of the seven glioblastoma tumour explants treated with di-scFv (SEQ ID NO: 41) showed significant cancer cell death (FIG. 14).

GBM cancer stem cells extracted from primary human GBM tumours from patients and grown as spheres were treated with control or di-scFv (SEQ ID NO: 41), and the effect of dose and incubation time on reduction of sphere volume was evaluated by confocal micrographs of DX1-rhodamine cellular penetration into GBM cells. Tumour spheres are recognised as a useful tool for pre-clinical studies as they retain tumour heterogeneity and more closely represent the original patient tumour. Treatment of human GBM cancer stem cells (CSCs) grown as tumour spheres with di-scFv (SEQ ID NO: 41) demonstrated cellular penetration in GBM spheres and reduced sphere volume in dose-dependent and time-dependant manner (FIG. 15).

Example 5—Evaluation of the Effect of Di-scFv (SEQ ID NO: 41) on Human GBM Cells in an Orthotopic Mouse Model An orthotopic mouse model of GBM was generated by intracranial injection of GBM cells extracted from human GBM tumours. Once the tumours developed in the brain, mice were treated by tail vein injection of control or di-scFv variant 13 (SEQ ID NO: 41), and effect of di-scFv on reduction of tumour volume was evaluated by extraction of tumours. Evaluation of brain sections showed that the glioblastoma tumours in mice treated with di-scFv were more than 40% smaller than the comparable tumours in control mice (FIG. 16A). TUNEL staining also demonstrated increased incidence of apoptosis in di-scFv-treated tumours (FIG. 16B). The observed reduction in tumour size and increased TUNEL staining in the di-scFv-treated GBM tumours suggested that di-scFv variant 13 (SEQ ID NO: 41) successfully crossed the blood brain barrier to localize in and impact GBM tumour growth. To confirm this, tumours and normal brain were probed for di-scFv by protein L immunostaining. As shown in FIG. 16C, the di-scFv was detected in the nuclei of GBM tumour cells, but was not evident in surrounding adjacent normal brain cells.

Additionally, a group of 7 mice was evaluated for the survival benefit and mice treated with di-scFv showed a median survival of 87 days, more than 20% longer than controls (median 72 days). Mean survival data reflected these trends (83 days±3.2 days for di-scFv treated mice, 71 days±1.2 days for controls) (FIG. 16E). Statistical analysis indicated a significant difference between the two groups, with P value=0.004. No toxicity or weight loss associated with di-scFv treatments was observed (FIG. 16D).

Example 6—The Effect of PAT-DX1 on Foci Accumulation

A matched pair of BRCA2-proficient and deficient DLD1 colon cancer cells and PTEN-proficient and deficient U251 human glioma cells were treated with control media or media containing 10 μM di-scFv variant 13 (SEQ ID NO: 41), 5 nM olaparib, or combination treatment. Phospho-53BP1 antibody staining was evaluated by Cell Profiler to determine mean number of phospho-53BP1 foci per cell. di-scFv variant 13 (SEQ ID NO: 41) treatment alone and in combination with olaparib increased the number of phospho-53BP1 foci in both the BRCA2-deficient DLD1 and the PTEN-deficient U251 cells, but not in proficient cells (FIG. 17).

It will be appreciated by persons skilled in the art that numerous variations and/or modifications may be made to the disclosure as shown in the specific embodiments without departing from the spirit or scope of the disclosure as broadly described. The present embodiments are, therefore, to be considered in all respects as illustrative and not restrictive.

All publications discussed above are incorporated herein in their entirety. Any discussion of documents, acts, materials, devices, articles or the like which has been included in the present specification is solely for the purpose of providing a context for the present disclosure. It is not to be taken as an admission that any or all of these matters form part of the prior art base or were common general knowledge in the field relevant to the present disclosure as it existed before the priority date of each claim of this application.

REFERENCES

Adams et al. (1993) Cancer Res. 53:4026
Ausubel et al., (editors), Current Protocols in Molecular Biology, Greene Pub.
Associates and Wiley-Interscience (1988, including all updates until present)
Axup, Proceedings of the National Academy of Sciences, 109 (40): 16101-6 (2012
AHo (Honegger A, Plückthun A (2001) J Mol Biol 309: 657-670
Bachor, et al., Molecular diversity, 17 (3): 605-11 (2013)
Chothia (Chothia C, Lesk A M (1987), J Mal Biol 196: 901-917
Chothia, et al. (1989), Nature 342: 877-883
Gruber et al. (1994) J. Immunol.:5368
Ed Harlow and David Lane (editors) Antibodies: A Laboratory Manual, Cold Spring Harbor Laboratory, (1988)
Hollinger et al., 1993, supra
Hu et al. (1996) Cancer Res. 56:3055
Jones et al., Nature 321:522-525 (1986)
Kogan et al., Nanomedicine (Lond). 2: 287-306, 2007
Kolodych, et al., Bioconjugate Chem., 26 (2): 197-200 (2015)
Kostelny et al. (1992) J Immunol 148:1547
Kuby, J., Immunology, 3$^{rd}$ Ed., W.H. Freeman & Co., New York (1998)
Lefranc, et al. (2003), Dev Comp Immunol 27: 55-77
Lyon, et al., Bioconjugate Chem., 32 (10): 1059-1062 (2014)
McCartney, et al. (1995) Protein Eng. 8:301
Novotny et al., Proc Natl Acad Sci USA 88: 8646-8650, 1991
Pack and Pluckthun (1992) Biochemistry 31:1579
Pierce Catalogue and Handbook, 1994-1995 (Pierce Chemical Co., Rockford, Ill.)
Presta, Curr. Op. Struct. Biol. 2:593-596 (1992)
Remington's Pharmaceutical Sciences (Mack Publishing Co. N.J. USA, 1991)
Rich and Myszka Curr. Opin. Biotechnol 11:54, 2000; Englebienne Analyst. 123: 1599, 1998

Riechmann et al., Nature 332:323-329 (1988)

Sambrook et al., Molecular Cloning: A Laboratory Manual, Cold Spring Harbor Laboratory Press (1989)

Wulbrand, et al., Multhoff, Gabriele, ed., *PLoS ONE.* 8 (5): e64730 (2013)

Zhu et al. (1997) Protein Sci 6:781

The invention claimed is:

1. A cell penetrating anti-DNA binding protein having an antigen binding domain, wherein the antigen binding domain binds to DNA and comprises:
a heavy chain variable region ($V_H$) having a complementarity determining region (CDR) 1 as shown in SEQ ID NO: 1, a CDR2 as shown in SEQ ID NO: 3 and a CDR3 as shown in SEQ ID NO: 4; and
a light chain variable region ($V_L$) having a CDR1 as shown in SEQ ID NO: 6, a CDR2 as shown in SEQ ID NO: 7 and a CDR3 as shown in SEQ ID NO: 8.

2. The binding protein of claim 1 comprising:
(i) a $V_H$ comprising a sequence at least 95% identical to the sequence as shown in any one of SEQ ID NOs: 21 to 23;
(ii) a $V_L$ comprising a sequence at least 95% identical to the sequence as shown in any one of SEQ ID NOs: 27 to 29; or
(iii) a $V_H$ comprising a sequence at least 95% identical to the sequence as shown in any one of SEQ ID NOs: 21 to 23 and a $V_L$ comprising a sequence at least 95% identical to the sequence as shown in any one of SEQ ID NOs: 27 to 29.

3. The binding protein according to claim 1, wherein the $V_H$ and a $V_L$ are separated by a linker which comprises the sequence shown in SEQ ID NO: 30.

4. The binding protein of claim 1, wherein, the $V_H$ and $V_L$ are in a single polypeptide chain.

5. The binding protein of claim 4, which is:
(i) a single chain Fv fragment (scFv);
(ii) a dimeric scFv (di-scFv);
(iii) a trimeric scFv (tri-scFv); or
(iv) any one of (i), (ii) or (iii) linked to a constant region of an antibody, Fc or a heavy chain constant domain $C_H2$ and/or $C_H3$.

6. The binding protein of claim 4, which is a scFv.

7. The binding protein of claim 4, which is a di-scFv.

8. The binding protein according to claim 1, wherein the $V_H$ and $V_L$ are in a separate polypeptide chain.

9. The binding protein of claim 8, which is:
(i) a diabody;
(ii) a triabody;
(iii) a tetrabody;
(iv) a Fab;
(v) a F(ab')$_2$;
(vi) a Fv; or
(vii) one of (i) to (vi) linked to a constant region of an antibody, Fc or a heavy chain constant domain $C_H2$ and/or $C_H3$; or,
(viii) an antibody.

10. The binding protein according to claim 1, which comprises an amino acid sequence as shown in any one of SEQ ID NOs: 41-47.

11. The binding protein of claim 1, which is conjugated to another compound.

12. The binding protein of claim 1, wherein the VH comprises a sequence at least 99% identical to the sequence as shown in SEQ ID NO: 21 and the VL comprises a sequence at least 99% identical to the sequence as shown in SEQ ID NO: 27.

13. The binding protein of claim 1, wherein the VH comprises the sequence shown in SEQ ID NO: 21 and the VL comprises the sequence shown in SEQ ID NO: 27.

14. A nucleic acid encoding a binding protein defined by claim 1.

15. An expression construct or recombinant cell comprising a nucleic acid defined by claim 14.

16. A method of treating cancer in a subject, the method comprising administering to the subject and effective amount of a binding protein defined claim 1.

17. A method of treating cancer in a subject in need thereof, the method comprising administering to the subject a binding protein or Fv fragment defined by claim 1 and a PARP inhibitor.

18. The method of claim 17, wherein the PARP inhibitor is olaparib.

19. The method of claim 17, wherein the cancer is substantially HDR deficient, substantially BRCA2 deficient, substantially PTEN deficient or resistant to PARP inhibition.

20. The method of claim 17, wherein the cancer is colon cancer, brain cancer, prostate, ovarian, breast, endometrial, melanoma, or pancreatic cancer, a triple negative breast cancer or glioblastoma.

* * * * *